United States Patent
Liu et al.

(10) Patent No.: US 12,049,517 B2
(45) Date of Patent: Jul. 30, 2024

(54) BISPECIFIC ANTIBODIES AND USES THEREOF

(71) Applicant: AB STUDIO INC., Hayward, CA (US)

(72) Inventors: Yue Liu, Foster City, CA (US);
Wenyan Cai, Fremont, CA (US);
Jiadong Shi, Fremont, CA (US)

(73) Assignee: Ab Studio Inc., Hayward, CA (US)

( * ) Notice: Subject to any disclaimer, the term of this patent is extended or adjusted under 35 U.S.C. 154(b) by 157 days.

(21) Appl. No.: 16/635,878

(22) PCT Filed: Aug. 1, 2018

(86) PCT No.: PCT/US2018/044778
§ 371 (c)(1),
(2) Date: Jan. 31, 2020

(87) PCT Pub. No.: WO2019/028125
PCT Pub. Date: Feb. 7, 2019

(65) Prior Publication Data
US 2021/0206882 A1    Jul. 8, 2021

Related U.S. Application Data

(60) Provisional application No. 62/654,112, filed on Apr. 6, 2018, provisional application No. 62/539,970, filed on Aug. 1, 2017.

(51) Int. Cl.
| | |
|---|---|
| *C07K 16/46* | (2006.01) |
| *A61P 35/00* | (2006.01) |
| *C07K 16/28* | (2006.01) |
| *A61K 39/00* | (2006.01) |

(52) U.S. Cl.
CPC ............ *C07K 16/468* (2013.01); *A61P 35/00* (2018.01); *C07K 16/2809* (2013.01); *C07K 16/2827* (2013.01); *C07K 16/2896* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 4,522,811 | A | 6/1985 | Eppstein et al. |
| 4,603,112 | A | 7/1986 | Paoletti et al. |
| 4,676,980 | A | 6/1987 | Segal et al. |
| 4,769,330 | A | 9/1988 | Paoletti et al. |
| 4,777,127 | A | 10/1988 | Suni et al. |
| 5,017,487 | A | 5/1991 | Stunnenberg et al. |
| 2006/0159673 | A1 | 7/2006 | Kojima |
| 2008/0095766 | A1* | 4/2008 | Koenig ............... A61P 43/00 424/133.1 |
| 2010/0331527 | A1 | 12/2010 | Davis et al. |
| 2013/0273050 | A1 | 10/2013 | Lutterbuese |
| 2014/0348839 | A1 | 11/2014 | Chowdhury et al. |
| 2015/0203580 | A1 | 7/2015 | Papadopoulos et al. |
| 2015/0259408 | A1 | 9/2015 | Tam et al. |
| 2016/0229924 | A1 | 8/2016 | Bernett et al. |
| 2016/0287732 | A1 | 10/2016 | Boerman et al. |
| 2016/0319036 | A1 | 11/2016 | Bruenker et al. |
| 2016/0368988 | A1 | 12/2016 | Bakker et al. |
| 2017/0029529 | A1 | 2/2017 | Croasdale et al. |
| 2017/0058023 | A1 | 3/2017 | Liu et al. |
| 2017/0320947 | A1* | 11/2017 | Moore ............... C07K 16/1027 |

FOREIGN PATENT DOCUMENTS

| | | |
|---|---|---|
| CN | 103987405 | 8/2014 |
| CN | 104379169 | 2/2015 |
| EP | 0345242 | 12/1989 |
| EP | 1876236 | 1/2008 |
| EP | 2009101 | 12/2008 |
| EP | 2295468 | 3/2011 |
| EP | 3243840 | 11/2017 |
| GB | 2200651 | 6/1991 |
| JP | 2017507650 | 3/2017 |
| WO | WO 89/01973 | 3/1989 |
| WO | WO 91/02805 | 3/1991 |
| WO | WO 96/27011 | 9/1996 |
| WO | WO 2004/032832 | 4/2004 |
| WO | WO 2004/106381 | 12/2004 |
| WO | WO 2008/077546 | 7/2008 |
| WO | WO 2013/126746 | 8/2013 |
| WO | WO 2013/163427 | 10/2013 |
| WO | WO 2013/170168 | 11/2013 |
| WO | WO 2014/189973 | 11/2014 |
| WO | WO 2015/143079 | 9/2015 |
| WO | WO 2016/077505 | 5/2016 |
| WO | WO 2016/086189 | 6/2016 |
| WO | WO 2016/110267 | 7/2016 |
| WO | WO 2016/110576 | 7/2016 |

(Continued)

OTHER PUBLICATIONS

EP Extended European Search Report in European Appln No. 18840836.3, dated Jun. 15, 2021, 17 pages.
PCT International Written Opinion in Appln. No. PCT/US20/15311, dated Apr. 23, 2020, 3 pages.
Barthelemy et al., "Comprehensive analysis of the factors contributing to the stability and solubility of autonomous human VH domains," Journal of Biological Chemistry, 2008, 283:3639-3654.
Beiboer et al., "Guided selection of a pan carcinoma specific antibody reveals similar binding characteristics yet structural divergence between the original murine antibody and its human equivalent," Journal of Molecular Biology, 2000, 296:833-849.

(Continued)

*Primary Examiner* — Meera Natarajan
*Assistant Examiner* — Cheom-Gil Cheong
(74) *Attorney, Agent, or Firm* — Fish & Richardson P.C.

(57) ABSTRACT

This disclosure relates to bispecific antibodies or antigen-binding fragments thereof, wherein the bispecific antibodies or antigen-binding fragments thereof specifically bind to two different antigens with different binding affinities.

19 Claims, 33 Drawing Sheets

Specification includes a Sequence Listing.

(56) References Cited

FOREIGN PATENT DOCUMENTS

| WO | WO 2016/111751 | 7/2016 |
|---|---|---|
| WO | WO 2017/010874 | 1/2017 |
| WO | WO 2017/055547 | 4/2017 |
| WO | WO 2017/106462 | 6/2017 |

OTHER PUBLICATIONS

Cai et al., "Biological acivity validation of a computationally designed Rituximab/CD3 T cell engager targeting CD20+ cancers with multiple mechanisms of action," Antibody Therapeutics, 2021, 4:4:228-241.

Choi et al., "Predicting antibody complementarity determining region structures without classification," Molecular BioSystems, 2011, 7:3327-334.

De Genst et al.,"Antibody repertoire development in camelids," Developmental and Comparative Immunology, 2006, 30:187-98.

Griffiths et al., "Human anti-self antibodies with high specificity from phage display libraries.," The EMBO Journal, 1993, 12:725-734.

Klinnka et al., "Human anti-CD30 recombinant antibodies by guided phage antibody selection using cell panning," British Journal of Cancer, 2000, 83:252-260.

Malia et al., "Epitope mapping and structural basis for the recognition of phosphorylated tau by the anti-tau antibody AT8," Proteins, 2016; 84:427-434.

Ward et al., "Binding activities of a repertoire of single immunoglobulin variable domains secreted from *Escherichia coli*," Nature, 1989, 341:544-546.

EP Extended European Search Report in European Appln No. 18840836.3, dated Mar. 3, 2021.

PCT International Search Report and Written Opinion in International Appln. No. PCT/US2020/047605, dated, Feb. 19, 2021, 16 pages.

Smith et al., "A novel, native-format bispecific antibody triggering T-cell killing of B-cells is robustly active in mouse tumor models and cynomolgus monkeys," Scientific Reports, Dec. 2015, 5:17943.

Yue, "Development of novel therapeutic antibodies via computational design," Jul. 2018, 31 pages.

Abhinandan, et al. "Analysis and improvements to Kabat and structurally correct numbering of antibody variable domains," Molecular Immunology, 2008, 45(14):3832-3839.

Brennan et al., "Preparation of bispecific antibodies by chemical recombination of monoclonal immunoglobulin G1 fragments," Science, 1985, 229:81-83.

Chothia et al., "Conformations of immunoglobulin hypervariable regions," Nature, 1989, 342(6252):877-83.

Cohen, "Naked DNA points way to vaccines," Science, 1993, 259(5102):1691-1692.

Fisher-Hoch et al., "Protection of rhesus monkeys from fatal Lassa fever by vaccination with a recombinant vaccinia virus containing the Lassa virus glycoprotein gene," Proc. Natl. Acad. Sci. USA, 1989, 86(1):317-321.

Flexner et al., "Attenuation and immunogenicity in primates of vaccinia virus recombinants expressing human interleukin-2," Vaccine, 1990,8(1):17-21.

Flexner et al., "Vaccinia virus expression vectors," Ann. N.Y. Acad Sci., 1989, 569:86-103.

Guzman et al., "Efficient and selective adenovirus-mediated gene transfer into vascular neointima," Circulation, 1993, 88:2838-2848.

Guzman et al., "Efficient gene transfer into myocardium by direct injection of adenovirus vectors," Cir. Res., 1993, 73:1202-1207.

International Preliminary Report on Patentability in Appln. No. PCT/US2018/044778, dated Feb. 4, 2020, 16 pages.

International Search Report and Written Opinion in International Appln. No. PCT/US2018/0447788, dated Jan. 10, 2019, 19 pages.

Irani, et al. "Molecular properties of human IgG subclasses and their implications for designing therapeutic monoclonal antibodies against infectious diseases." Molecular immunology, 2015, 67(2):71-182.

Jones et al., "Replacing the complementarity-determining regions in a human antibody with those from a mouse," Nature, 1986, 321:522-525.

Jones et al., "The INNs and outs of antibody nonproprietary names," Mabs, 2016, 8(1):1-9.

Kass-Eisler et al., "Quantitative determination of adenovirus-mediated gene delivery to rat cardiac myocytes in vitro and in vivo," Proc. Natl. Acad. Sci. USA, 1993, 90(24):11498-11502.

Kohler et al., "Continuous cultures of fused cells secreting antibody of predefined specificity," Nature, 1975, 256(5517):495-497.

Kolls et al., "Prolonged and effective blockade of tumor necrosis factor activity through adenovirus-mediated gene transfer," Proc. Natl. Acad. Sci. USA, 1994, 91:215-219.

Kozbor et al., "The production of monoclonal antibodies from human lymphocytes," Immunol. Today, 1983, 4(3):72.

Li et al., "Construction and characterization of a humanized anti-human CD3 monoclonal antibody 12F6 with effective immunoregulation functions," Immunology, 2005, 116(4):487-498.

Martin et al., "Molecular modeling of antibody combining sites," Methods Enzymol., 1991, 203:121-53.

Martin, "Protein sequence and structure analysis of antibody variable domains," Antibody engineering, Springer Berlin Heidelberg, 2001, 422-439.

Morea et al., "Antibody structure, prediction and redesign," Biophys Chem., 1997, 68(1-3):9-16.

Morea et al., "Conformations of the third hypervariable region in the VH domain of immunoglobulins," J Mol Biol., 1998, 275(2):269-94.

Ponomarenko and Bourne, "Antibody-protein interactions: benchmark datasets and prediction tools evaluation," BMC Structural Biology, 2007, 7:64.

Ridgway et al., "'Knobs-into-holes' engineering of antibody CH3 domains for heavy chain heterodimerization." Protein Engineering, 1996, 9(7):617-621.

Ridgway et al., "Identification of a human anti-CD55 single-chain Fv by subtractive panning of a phage library using tumor and nontumor cell lines," Cancer Res., 1999, 59 (11):2718-2723.

Riechmann et al., "Reshaping human antibodies for therapy," Nature, 1988, 332(6162):323-327.

Rosenfeld et al., "Adenovirus-mediated transfer of a recombinant alpha 1-antitrypsin gene to the lung epithelium in vivo," Science, 1991, 252(5004):431-434.

Silva et al. "The S228P mutation prevents in vivo and in vitro IgG4 Fab-arm exchange as demonstrated using a combination of novel quantitative immunoassays and physiological matrix preparation." Journal of Biological Chemistry 290.9 (2015): 5462-5469.

Ulmer et al., "Heterologous protection against influenza by injection of DNA encoding a viral protein," Science, 1993, 259(5102):1745-1749.

Verhoeyen et al., "Reshaping human antibodies: grafting an antilysozyme activity," Science, 1988, 239(4847):1534-1536.

Vidarsson, et al, "IgG subclasses and allotypes: from structure to effector functions." Frontiers in immunology, 2014, 5.

Wu et al., "An analysis of the sequences of the variable regions of Bence Jones proteins and myeloma light chains and their implications for antibody complementarity," J. Exp. Med., 1970, 132(2):211-250.

International Preliminary Report on Patentability in Appl. No. PCT/US2020/015311, dated Aug. 12, 2021, 5 pages.

GenBank Accession No. AAV65828.1, "anti-human CD3 12F6 immunoglobulin heavy chain variable region precursor, partial [Mus musculus]," Jun. 7, 2004, 2 pages.

Xiong et al., "Study on the biological activity of anti-CD3/anti-CD20 dia body," Chin J Microbiol Immunol, Nov. 2001, 21(6):627-631 (with English abstract).

CN Office Action in Chinese Appln. No. 201880062833.7, dated Mar. 1, 2023, 20 pages (with English translation).

EP Office Action in European Appln. No. 18840836.3, dated Mar. 14, 2023, 7 pages.

JP Japanese Office Action in Japanese Appln. No. 2020-529100, dated Mar. 1, 2023, 11 pages.

(56) References Cited

OTHER PUBLICATIONS

Macor et al., "Bispecific antibodies targeting tumor-associated antigens and neutralizing complement regulators increase the efficacy of antibody-based immunotherapy in mice," Leukemia, Feb. 2015, 29(2):406-14.
Zhang et al., "Relationship between Bcl-2, p53 and CD55 expression and outcome of rituximab in treatment of DLBCL patients," Chinese Journal of Clinicians, 4(12), Jan. 2010, pages (English translation).
Extended Search Report in European Appln No. 22160823.5, dated Sep. 30, 2022, 16 pages.
CN Office Action in Chinese Appln. No. 201880062833.7, mailed on Nov. 1, 2023, 16 pages (with English translation).
EP Office Action in European Appln. No. 22160823.5, mailed on Jan. 25, 2024, 5 pages.

* cited by examiner

| | | | | | | |
|---|---|---|---|---|---|---|
| Majority | QSALTQPASVSGSPGQSITISCTGTSSDVGGYNYVSWYQQHPGKAPKLMIYDVSKRPSGV | | | | | |
| | 10 | 20 | 30 | 40 | 50 | 60 |
| Common LC for BsAb v2 | QSALTQPASVSGSPGQSITISCTGTSSDVGGYNYVSWYQQHPGKAPKLMIYDVSKRPSGV | | | | | 60 |
| Common LC for BsAb v1 | QSALTQPASVSGSPGQSITISCTGTSSDVGGYNYVSWYQQHPGKAPKLMIYDVSKRPSGV | | | | | 60 |

| | | | | | | |
|---|---|---|---|---|---|---|
| Majority | SNRFSGSKSGNTASLTISGLQAEDEADYYCSSYTSXSTRIFGGGTKVTVLRTVAAPSVFI | | | | | |
| | 70 | 80 | 90 | 100 | 110 | 120 |
| Common LC for BsAb v2 | SNRFSGSKSGNTASLTISGLQAEDEADYYCSSYTSSSTRIFGGGTKVTVLRTVAAPSVFI | | | | | 120 |
| Common LC for BsAb v1 | SNRFSGSKSGNTASLTISGLQAEDEADYYCSSYTSASTRIFGGGTKVTVLRTVAAPSVFI | | | | | 120 |

| | | | | | | |
|---|---|---|---|---|---|---|
| Majority | FPPSDEQLKSGTASVVCLLNNFYPREAKVQWKVDNALQSGNSQESVTEQDSKDSTYSLSS | | | | | |
| | 130 | 140 | 150 | 160 | 170 | 180 |
| Common LC for BsAb v2 | FPPSDEQLKSGTASVVCLLNNFYPREAKVQWKVDNALQSGNSQESVTEQDSKDSTYSLSS | | | | | 180 |
| Common LC for BsAb v1 | FPPSDEQLKSGTASVVCLLNNFYPREAKVQWKVDNALQSGNSQESVTEQDSKDSTYSLSS | | | | | 180 |

| | | | |
|---|---|---|---|
| Majority | TLTLSKADYEKHKVYACEVTHQGLSSPVTKSFNRGEC | | |
| | 190 | 200 | 210 |
| Common LC for BsAb v2 | TLTLSKADYEKHKVYACEVTHQGLSSPVTKSFNRGEC | | 217 |
| Common LC for BsAb v1 | TLTLSKADYEKHKVYACEVTHQGLSSPVTKSFNRGEC | | 217 |

FIG. 24

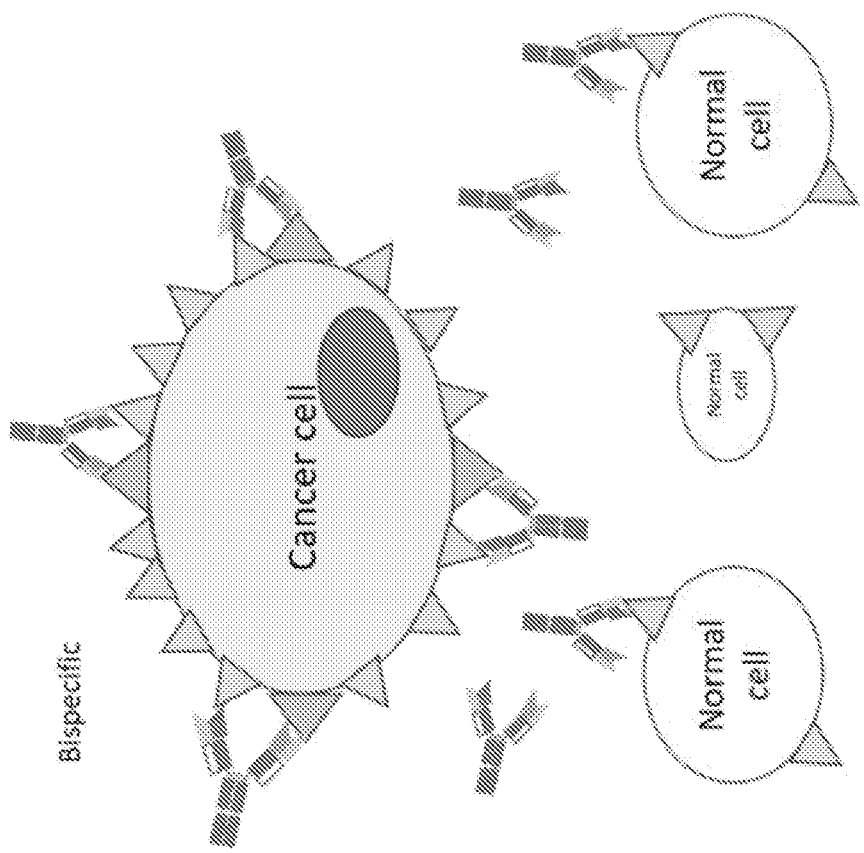
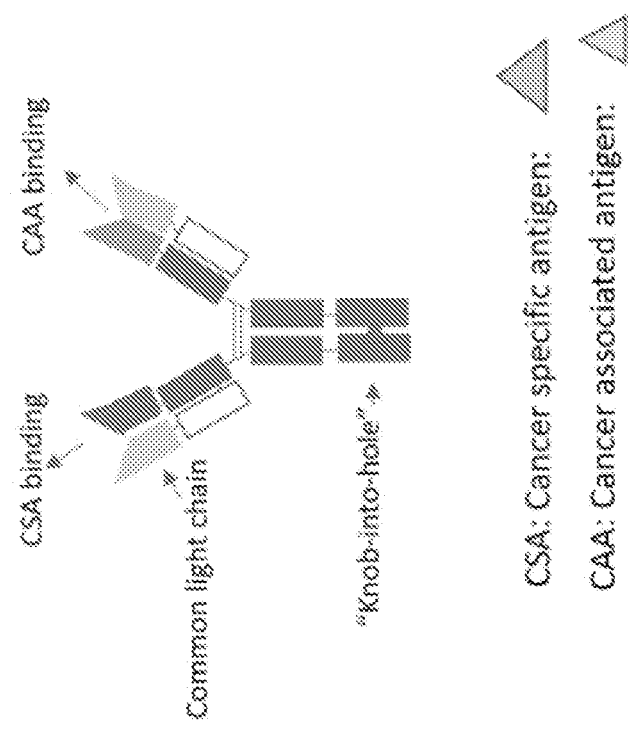
FIG. 29

SEQUENCE LISTING

<160> NUMBER OF SEQ ID NOS: 69

<210> SEQ ID NO 1
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Arg Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala
        115                 120

<210> SEQ ID NO 2
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Gln Glu Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Glu Gly Leu Glu Trp Ile
        35                  40                  45

Gly Tyr Ile Asn Pro Ser Ser Gly Tyr Thr Lys Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Trp Gln Asp Tyr Asp Val Tyr Phe Asp Tyr Trp Gly Glu Gly
            100                 105                 110

Thr Thr Leu Thr Val Ser Ser
        115

<210> SEQ ID NO 3
<211> LENGTH: 107
<212> TYPE: PRT
<213> ORGANISM: Artificial Sequence
<220> FEATURE:
<223> OTHER INFORMATION: Description of Artificial Sequence: Synthetic

```
                                     -continued
       polypeptide

<400> SEQUENCE: 3

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg
            100                 105

<210> SEQ ID NO 4
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Val Gln Leu Leu Glu Ser Gly Gly Gly Leu Val Glu Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Glu
            100                 105                 110

Gly Thr Leu Val Thr Val Ser Ser
        115                 120

<210> SEQ ID NO 5
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Lys Leu Gln Glu Ser Gly Gly Gly Leu Val Lys Pro Gly Gly
1               5                   10                  15

Ser Leu Lys Leu Ser Cys Ala Ala Ser Gly Phe Thr Phe Ser Gly Tyr
            20                  25                  30

Gly Met Ser Trp Ile Arg Gln Thr Pro Gly Lys Arg Leu Glu Trp Val
        35                  40                  45
```

Ala Thr Ile Asn Ser Gly Gly Ser Tyr Thr Tyr Tyr Ser Asp Ser Val
                50                  55                  60

Lys Gly Arg Phe Thr Ile Ser Arg Asp Asn Val Lys Asn Thr Leu Tyr
 65                  70                  75                  80

Leu Gln Met Ser Ser Leu Lys Ser Glu Asp Thr Ala Met Tyr Tyr Cys
                    85                  90                  95

Ala Arg Arg Asn Gly Thr Leu Tyr Tyr Tyr Leu Met Asp Tyr Trp Gly
                100                 105                 110

Arg Gly Thr Leu Val Thr Val Ser Ser
                115                 120

<210> SEQ ID NO 6
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Ser Ala Leu Thr Gln Pro Ala Ser Val Ser Gly Ser Pro Gly Gln
 1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
                35                  40                  45

Met Ile Tyr Asp Val Ser Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ala
                    85                  90                  95

Ser Thr Arg Ile Phe Gly Gly Gly Thr Lys Val Thr Val Leu Arg
                100                 105                 110

<210> SEQ ID NO 7
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Ser Ala Leu Thr Gln Pro Ala Ser Val Ser Gly Ser Pro Gly Gln
 1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
                35                  40                  45

Met Ile Tyr Asp Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                    85                  90                  95

Ser Thr Arg Ile Phe Gly Gly Gly Thr Lys Val Thr Val Leu Arg
                100                 105                 110

<210> SEQ ID NO 8
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala
        115                 120

<210> SEQ ID NO 9
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg
            100                 105

<210> SEQ ID NO 10
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Ser Ser Gly Tyr Thr Lys Tyr Asn Gln Lys Phe
    50                  55                  60

Lys Asp Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Trp Gln Asp Tyr Asp Val Tyr Phe Asp Tyr Trp Gly Gln Gly
            100                 105                 110

Thr Thr Leu Thr Val Ser Ser
            115
```

<210> SEQ ID NO 11
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Pro Thr
            85                  90                  95

Phe Gly Gly Gly Thr Lys Leu Glu Thr Lys Arg
            100                 105
```

<210> SEQ ID NO 12
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60
```

-continued

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ile Lys Leu Gly Thr Val Thr Val Asp Tyr Trp Gly Gln
            100                 105                 110

Gly Thr Leu Val Thr Val Ser Ser
            115                 120
```

<210> SEQ ID NO 13
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Arg Val Phe Gly Thr Gly Thr Lys Val Thr Val Leu
            100                 105                 110
```

<210> SEQ ID NO 14
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Gln Val Lys Leu Gln Glu Ser Gly Gly Gly Leu Val Gln Pro Gly Gly
 1               5                  10                  15

Ser Leu Lys Leu Ser Cys Ala Ala Ser Gly Phe Thr Phe Ser Gly Tyr
                20                  25                  30

Gly Met Ser Trp Ile Arg Gln Thr Pro Asp Lys Arg Leu Glu Trp Val
            35                  40                  45

Ala Thr Ile Asn Ser Gly Gly Ser Tyr Thr Tyr Tyr Ser Asp Ser Val
 50                  55                  60

Lys Gly Arg Phe Thr Ile Ser Arg Asp Asn Val Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ala Arg Arg Asn Gly Thr Leu Tyr Tyr Tyr Leu Met Asp Tyr Trp Gly
            100                 105                 110

Arg Gly Thr Leu Val Thr Val Ser Ser
            115                 120
```

```
<210> SEQ ID NO 15
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Ser Val Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Phe
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Val
65                  70                  75                  80

Gln Ala Glu Asp Glu Ala Asp Tyr Tyr Cys Ser Ser Tyr Thr Ser Ala
                85                  90                  95

Ser Thr Val Ile Phe Gly Gly Gly Thr Lys Leu Thr Val Leu
            100                 105                 110

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Tyr Asn Met His
1               5

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Ile Tyr Pro Gly Asn Gly Asp Thr Ser Tyr Asn Gln Lys Phe Lys
1               5                   10                  15

Gly

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Thr Tyr Tyr Gly Gly Asp Trp Tyr Phe Asn Val
1               5                   10

<210> SEQ ID NO 19
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Tyr Thr Phe Thr Ser Tyr
1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Tyr Pro Gly Asn Gly Asp
1               5

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Thr Tyr Tyr Gly Gly Asp Trp Tyr Phe Asn Val
1               5                   10

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Tyr Thr Met His
1               5

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Tyr Ile Asn Pro Ser Ser Gly Tyr Thr Lys Tyr Asn Gln Lys Phe Lys
1               5                   10                  15

Asp

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24
```

```
Trp Gln Asp Tyr Asp Val Tyr Phe Asp Tyr
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Tyr Thr Phe Thr Ser Tyr
1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asn Pro Ser Ser Gly Tyr
1               5

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Trp Gln Asp Tyr Asp Val Tyr Phe Asp Tyr
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Ala Ser Ser Ser Val Ser Tyr Ile His
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Thr Ser Asn Leu Ala Ser
1               5

<210> SEQ ID NO 30
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 30

Gln Gln Trp Thr Ser Asn Pro Pro Thr
1               5

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Ala Ser Ser Ser Val Ser Tyr Ile His
1               5                   10

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ala Thr Ser Asn Leu Ala Ser
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Gln Trp Thr Ser Asn Pro Pro Thr
1               5

<210> SEQ ID NO 34
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Arg Ser Glu Asp Ser Ala Val Tyr Tyr Cys
                85                  90                  95
```

Ala Arg Ser Thr Tyr Tyr Gly Gly Asp Trp Tyr Phe Asn Val Trp Gly
                100                 105                 110

Ala Gly Thr Thr Val Thr Val Ser Ala Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 35
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 35

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Arg Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Thr Ser Lys Leu Thr Val
                405                 410                 415
```

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 36
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Arg Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly

```
                305                 310                 315                 320
Lys Glu Tyr Lys Cys Lys Val Ser Asn Lys Ala Leu Pro Ala Pro Ile
                    325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Tyr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
        450

<210> SEQ ID NO 37
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Val Gln Leu Gln Glu Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
                20                  25                  30

Thr Met His Trp Val Lys Gln Arg Pro Gly Glu Gly Leu Glu Trp Ile
            35                  40                  45

Gly Tyr Ile Asn Pro Ser Ser Gly Tyr Thr Lys Tyr Asn Gln Lys Phe
        50                  55                  60

Lys Asp Lys Ala Thr Leu Thr Ala Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Trp Gln Asp Tyr Asp Val Tyr Phe Asp Tyr Trp Gly Glu Gly
                100                 105                 110

Thr Thr Leu Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205
```

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Glu Glu Met Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys

<210> SEQ ID NO 38
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Val Gln Leu Gln Glu Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Glu Gly Leu Glu Trp Ile
        35                  40                  45

Gly Tyr Ile Asn Pro Ser Ser Gly Tyr Thr Lys Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Glu Leu Ser Ser Leu Thr Ser Glu Asp Ser Ala Val Tyr Tyr Cys
            85                  90                  95

Ala Arg Trp Gln Asp Tyr Asp Val Tyr Phe Asp Tyr Trp Gly Glu Gly
        100                 105                 110

```
Thr Thr Leu Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Tyr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 39
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Val Gln Leu Gln Glu Ser Gly Ala Glu Leu Ala Arg Pro Gly Ala
1               5                   10                  15
```

```
Ser Val Lys Met Ser Cys Lys Ala Ser Gly Tyr Thr Phe Thr Ser Tyr
             20                  25                  30
Thr Met His Trp Val Lys Gln Arg Pro Gly Glu Gly Leu Glu Trp Ile
             35                  40                  45
Gly Tyr Ile Asn Pro Ser Ser Gly Tyr Thr Lys Tyr Asn Gln Lys Phe
             50                  55                  60
Lys Asp Lys Ala Thr Leu Thr Ala Asp Lys Ser Ser Thr Ala Tyr
 65                  70                  75                  80
Met Glu Leu Ser Ser Leu Thr Ser Glu Asp Ser Ala Val Tyr Tyr Cys
             85                  90                  95
Ala Arg Trp Gln Asp Tyr Asp Val Tyr Phe Asp Tyr Trp Gly Glu Gly
            100                 105                 110
Thr Thr Leu Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
            130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
            195                 200                 205
Ser Asn Thr Lys Val Asp Lys Lys Val Glu Pro Lys Ser Cys Asp Lys
210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
            355                 360                 365
Cys Leu Val Lys Gly Phe Tyr Pro Ser Asp Ile Ala Val Glu Trp Glu
            370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
```

Lys

<210> SEQ ID NO 40
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ser Tyr Ile Met Met
1               5

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ser Ile Tyr Pro Ser Gly Gly Ile Thr Phe Tyr Ala Asp Thr Val Lys
1               5                   10                  15
Gly

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ile Lys Leu Gly Thr Val Thr Thr Val Asp Tyr
1               5                   10

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Phe Thr Phe Ser Ser Tyr
1               5

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Tyr Pro Ser Gly Gly Ile
1               5

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ile Lys Leu Gly Thr Val Thr Thr Val Asp Tyr
1               5                   10

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Tyr Gly Met Ser
1               5

```
<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Thr Ile Asn Ser Gly Gly Ser Tyr Thr Tyr Tyr Ser Asp Ser Val Lys
1               5                   10                  15

Gly

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Arg Asn Gly Thr Leu Tyr Tyr Tyr Leu Met Asp Tyr
1               5                   10

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Phe Thr Phe Ser Gly Tyr
1               5

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asn Ser Gly Gly Ser Tyr
1               5

<210> SEQ ID NO 52
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Asn Gly Thr Leu Tyr Tyr Tyr Leu Met Asp Tyr
1               5                   10

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 53

Thr Gly Thr Ser Ser Asp Val Gly Gly Tyr Asn Tyr Val Ser
1               5                   10

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asp Val Ser Lys Arg Pro Ser
1               5

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Ser Tyr Thr Ser Ala Ser Thr Arg Ile
1               5                   10

<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Thr Gly Thr Ser Ser Asp Val Gly Gly Tyr Asn Tyr Val Ser
1               5                   10

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asp Val Ser Lys Arg Pro Ser
1               5

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ser Ser Tyr Thr Ser Ala Ser Thr Arg Ile
1               5                   10

<210> SEQ ID NO 59
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Thr Gly Thr Ser Ser Asp Val Gly Gly Tyr Asn Tyr Val Ser
1               5                   10

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asp Val Ser Asn Arg Pro Ser
1               5

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ser Ser Tyr Thr Ser Ser Ser Thr Arg Ile
1               5                   10

<210> SEQ ID NO 62
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Thr Gly Thr Ser Ser Asp Val Gly Gly Tyr Asn Tyr Val Ser
1               5                   10

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asp Val Ser Asn Arg Pro Ser
1               5

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ser Ser Tyr Thr Ser Ser Ser Thr Arg Ile
```

<210> SEQ ID NO 65
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 65

```
Glu Val Gln Leu Leu Glu Ser Gly Gly Gly Leu Val Glu Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Glu
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350
```

```
Thr Leu Pro Pro Ser Arg Glu Glu Met Thr Lys Asn Gln Val Ser Leu
            355                 360                 365

Tyr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 66
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Val Lys Leu Gln Glu Ser Gly Gly Gly Leu Val Lys Pro Gly Gly
1               5                   10                  15

Ser Leu Lys Leu Ser Cys Ala Ala Ser Gly Phe Thr Phe Ser Gly Tyr
            20                  25                  30

Gly Met Ser Trp Ile Arg Gln Thr Pro Gly Lys Arg Leu Glu Trp Val
        35                  40                  45

Ala Thr Ile Asn Ser Gly Gly Ser Tyr Thr Tyr Tyr Ser Asp Ser Val
    50                  55                  60

Lys Gly Arg Phe Thr Ile Ser Arg Asp Asn Val Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Arg Asn Gly Thr Leu Tyr Tyr Tyr Leu Met Asp Tyr Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255
```

```
Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Thr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 67
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ala
                85                  90                  95

Ser Thr Arg Ile Phe Gly Gly Gly Thr Lys Val Thr Val Leu Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
```

```
145                 150                 155                 160
Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 68
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Ile Phe Gly Gly Gly Thr Lys Val Thr Val Leu Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 69
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: X
<222> LOCATION: (55)..(55)
<223> OTHER INFORMATION: X can be either N or K
```

```
<220> FEATURE:
<221> NAME/KEY: X
<222> LOCATION: (96)..(96)
<223> OTHER INFORMATION: X can be either S or A

<400> SEQUENCE: 69

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Xaa Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Xaa
                85                  90                  95

Ser Thr Arg Ile Phe Gly Gly Gly Thr Lys Val Thr Val Leu Arg Thr
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

BISPECIFIC ANTIBODIES AND USES THEREOF

CLAIM OF PRIORITY

This application is a National Stage Application under 35 U.S.C. § 371 and claims the benefit of International Application No. PCT/US2018/044778, filed on Aug. 1, 2018, which claims the benefit of U.S. Provisional Application Ser. No. 62/539,970, filed on Aug. 1, 2017 and U.S. Provisional Application Ser. No. 62/654,112, filed on Apr. 6, 2018. The entire contents of the foregoing are incorporated herein by reference.

TECHNICAL FIELD

This disclosure relates to bispecific antibodies or antigen-binding fragments thereof.

BACKGROUND

A bispecific antibody is an artificial protein that can simultaneously bind to two different types of antigens or two different epitopes. This dual specificity opens up a wide range of applications, including redirecting T cells to tumor cells, blocking two different signaling pathways simultaneously, dual targeting of different disease mediators, and delivering payloads to targeted sites. The approval of catumaxomab (anti-EpCAM and anti-CD3) and blinatumomab (anti-CD19 and anti-CD3) has become a major milestone in the development of bispecific antibodies.

As bispecific antibodies have various applications, there is a need to continue to develop various therapeutics based on bispecific antibodies.

SUMMARY

This disclosure relates to imbalanced bispecific antibodies or antigen-binding fragments, wherein the bispecific antibodies or antigen-binding fragments specifically bind to two different antigens with different binding affinities.

In some aspects, the disclosure relates to a bispecific antibody or antigen-binding fragment including a first heavy chain variable region, a second heavy chain variable region, a first light chain variable region, and a second light chain variable region, wherein the first heavy chain variable region and the first light chain variable region associate with each other, forming a first antigen binding region that specifically binds to a first antigen with a binding affinity greater than $10^7$ $M^{-1}$, $10^8$ $M^{-1}$, $10^9$ $M^{-1}$, $10^{10}$ $M^{-1}$, $10^{11}$ $M^{-1}$, or $10^{12}$ $M^{-1}$, and the second heavy chain variable region and the second light chain variable region associate with each other, forming a second antigen binding region that specifically binds to a second antigen with a binding affinity less than $10^9$ $M^{-1}$, $10^8$ $M^{-1}$, $10^7$ $M^{-1}$, $10^6$ $M^{-1}$, $10^5$ $M^{-1}$, or $10^4$ $M^{-1}$.

In some embodiments, the second antigen binding region specifically binds to the second antigen with a binding affinity greater than $10^7$ $M^{-1}$, $10^6$ $M^{-1}$, $10^5$ $M^{-1}$, or $10^4$ $M^{-1}$.

In some embodiments, the binding affinity of the first antigen binding region when it binds to the first antigen is at least 100, 1000, or 10000 times greater than the binding affinity of the second antigen binding region when it binds to the second antigen.

In some embodiments, the first light chain variable region and the second light chain variable region are at least 90%, 95%, 99%, or 100% identical.

In some aspects, the disclosure relates to a bispecific antibody or antigen-binding fragment including a first arm comprising a first heavy chain variable region, and a first light chain variable region; and a second arm comprising a second heavy chain variable region, and a second light chain variable region, wherein the first arm specifically binds to a first antigen with a binding affinity greater than $10^7$ $M^{-1}$, $10^8$ $M^{-1}$, $10^9$ $M^{-1}$, $10^{10}$ $M^{-1}$, $10^{11}$ $M^{-1}$, $10^{12}$ $M^{-1}$, and the second arm specifically binds to a second antigen with a binding affinity less than $10^9$ $M^{-1}$, $10^8$ $M^{-1}$, $10^7$ $M^{-1}$, $10^6$ $M^{-1}$, $10^5$ $M^{-1}$, or $10^4$ $M^{-1}$.

In some embodiments, the second arm specifically binds to the second antigen with a binding affinity greater than $10^7$ $M^{-1}$, $10^6$ $M^{-1}$, $10^5$ $M^{-1}$, or $10^4$ $M^{-1}$.

In some embodiments, the binding affinity of the first arm when it binds to the first antigen is at least 100, 1000, or 10000 times greater than the binding affinity of the second arm when it binds to the second antigen.

In some embodiments, the first light chain variable region and the second light chain variable region are at least 90%, 95%, 99%, or 100% identical.

In some aspects, the disclosure relates to a bispecific antibody or antigen-binding fragment including a first heavy chain comprising a first heavy chain variable region, a second heavy chain comprising a second heavy chain variable region, a first light chain comprising a first light chain variable region, and a second light chain comprising a second light chain variable region, wherein the first heavy chain variable region and the first light chain variable region associate with each other, forming a first antigen binding region that specifically binds to a first antigen with a binding affinity greater than $10^7$ $M^{-1}$, $10^8$ $M^{-1}$, $10^9$ $M^{-1}$, $10^{10}$ $M^{-1}$, $10^{11}$ $M^{-1}$, $10^{12}$ $M^{-1}$, and the second heavy chain variable region and the second light chain variable region associate with each other, forming a second antigen binding region that specifically binds to a second antigen with a binding affinity less than $10^9$ $M^{-1}$, $10^8$ $M^{-1}$, $10^7$ $M^{-1}$, $10^6$ $M^{-1}$, $10^5$ $M^{-1}$, or $10^4$ $M^{-1}$.

In some embodiments, the second antigen binding region specifically binds to the second antigen with a binding affinity greater than $10^7$ $M^{-1}$, $10^6$ $M^{-1}$, $10^5$ $M^{-1}$, or $10^4$ $M^{-1}$.

In some embodiments, the binding affinity of the first antigen binding region when it binds to the first antigen is at least 100, 1000, or 10000 times greater than the binding affinity of the second antigen binding region when it binds to the second antigen.

In some embodiments, the first light chain and the second light chain are at least 90%, 95%, 99%, or 100% identical.

In some embodiments, the first heavy chain and the second chain associate with each other by the knobs into holes approach.

In some embodiments, the first antigen is a cancer specific antigen, and the second antigen is CD3.

In some embodiments, the first antigen is CD20, and the second antigen is CD3.

In some embodiments, the first heavy chain variable region comprises a sequence that is at least 80%, 85%, 90%, or 95% identical to SEQ ID NO: 1, the second heavy chain variable region comprises a sequence that is at least 80%, 85%, 90%, or 95% identical to SEQ ID NO: 2, and the first and the second light chain variable regions comprise a sequence that is at least 80%, 85%, 90%, or 95% identical to SEQ ID NO: 3.

In some embodiments, the first antigen is a cancer specific antigen, and the second antigen is a cancer-associated antigen.

In some embodiments, the first antigen is PD-L1, and the second antigen is CD55.

In some embodiments, the first heavy chain variable region comprises a sequence that is at least 80%, 85%, 90%, or 95% identical to SEQ ID NO: 4, the second heavy chain variable region comprises a sequence that is at least 80%, 85%, 90%, or 95% identical to SEQ ID NO: 5, and the first and the second light chain variable regions comprise a sequence that is at least 80%, 85%, 90%, or 95% identical to SEQ ID NO: 6 or SEQ ID NO: 7.

In some aspects, the disclosure relates to a method of making bispecific antibody or antigen-binding fragment, the method including selecting a first antigen and a second antigen, and identifying a first antibody or antigen-binding fragment that binds to the first antigen and a second antibody or antigen-binding fragment that binds to the second antigen, wherein the first antibody or antigen-binding fragment comprises a first heavy chain variable region (VHa) and a first light chain variable region (VLa), and the second antibody or antigen-binding fragment comprises a second heavy chain variable region (VHb) and a second light chain variable region (VLb); determining the amino acid sequence of VHa, VLa, VHb, and VLb; aligning the amino acid sequences of VLa and VLb and determining that the sequence homology between VLa and VLb is greater than 80%; designing a common light chain variable region (VLc), wherein the VLc, when it associates with VHa, maintains the affinity to the first antigen; redesigning the VHa and VHb sequences, thereby obtaining VHa' and VHb' to increase the difference of biochemical or biophysical characteristics between a first protein comprising two polypeptides each comprising VHa' and two polypeptides each comprising VLc, and a second protein comprising two polypeptides each comprising VHb' and two polypeptides each comprising VLc; and producing a bispecific antibody or antigen-binding fragment that has two light chain variable regions and two heavy chain variable regions, wherein the two light variable regions each comprises VLc, and the two heavy chain variable regions comprise VHa' and VHb' respectively.

In some embodiments, in step (d), the binding affinity of the VLc-VHb to the second antigen can decrease.

In some embodiments, the method further includes developing a buffer system to purify the bispecific antibody or antigen-binding fragment.

In some aspects, the disclosure relates to a method of making bispecific antibody or antigen-binding fragment, the method including selecting a first antigen and a second antigen, and identifying a first antibody or antigen-binding fragment that binds to the first antigen and a second antibody or antigen-binding fragment that binds to the second antigen, wherein the first antibody or antigen-binding fragment comprises a first heavy chain variable region (VHa) and a first light chain variable region (VLa), and the second antibody or antigen-binding fragment comprises a second heavy chain variable region (VHb) and a second light chain variable region (VLb); determining the amino acid sequence of VHa, VLa, and VLb; aligning the amino acid sequences of VLa and VLb and determining the sequence homology between VLa and VLb is less than 80%; replacing all light chain variable regions in a phage display antibody library with the VLa, and panning against the second antigen to obtain a third heavy chain variable region (VHc); redesigning the VHa and VHc sequences, thereby obtaining VHa' and VHc' to increase the difference of biochemical or biophysical characteristics between a first protein comprising two polypeptides each comprising VHa' and two polypeptides each comprising VLa, and a second protein comprising two polypeptides each comprising VHc' and two polypeptides each comprising VLa; and producing a bispecific antibody or antigen-binding fragment that has two light chain variable regions and two heavy chain variable regions, wherein the two light variable regions each comprises VLa, and the two heavy chain variable regions comprise VHa' and VHc' respectively.

In some embodiments, the method further includes developing a buffer system to purify the bispecific antibody or antigen-binding fragment.

In some aspects, the disclosure relates to a method of making bispecific antibody or antigen-binding fragment, the method including selecting a first antigen and a second antigen, and identifying a first antibody or antigen-binding fragment that binds to the first antigen and a second antibody or antigen-binding fragment that binds to the second antigen, wherein the first antibody or antigen-binding fragment comprises a first heavy chain variable region (VHa) and a first light chain variable region (VLa), and the second antibody or antigen-binding fragment comprises a second heavy chain variable region (VHb) and a second light chain variable region (VLb); determining the amino acid sequence of VHa, VLa, VHb, and VLb; aligning the amino acid sequences of VLa and VLb and determining the sequence homology between VLa and VLb is less than 80%; replacing all light chain variable regions in a phage display antibody library with a plurality of light chain variable regions, wherein the light chain variables regions are at least 80%, 85%, 90%, 95%, or 99% identical to VLa or VLb; panning against the second antigen; selecting a common light chain variable region (VLc), and a third heavy chain variable region (VHc), wherein VHa-VLc binds to the first antigen with a desired affinity and VHc-VLc binds to the second antigen with a desired affinity; redesigning the VHa and VHc sequences, thereby obtaining VHa' and VHc' to increase the difference of biochemical or biophysical characteristics between a first protein comprising two polypeptides each comprising VHa' and two polypeptides each comprising VLc, and a second protein comprising two polypeptides each comprising VHc' and two polypeptides each comprising VLc; and producing a bispecific antibody or antigen-binding fragment that has two light chain variable regions and two heavy chain variable regions, wherein the two light variable regions each comprises VLc, and the two heavy chain variable regions comprise VHa' and VHc' respectively.

In some embodiments, in step (d), the plurality of light chain variable regions are produced by error-prone PCR.

In some embodiments, the method further includes developing a buffer system to purify the bispecific antibody or antigen-binding fragment.

In one aspect, the disclosure provides methods of making bispecific antibody or antigen-binding fragment thereof. The methods involve one or more of the following steps:
(a) selecting a first antigen and a second antigen, and identifying a first antibody or antigen-binding fragment thereof that binds to the first antigen and a second antibody or antigen-binding fragment thereof that binds to the second antigen. In some embodiments, the first antibody or antigen-binding fragment thereof comprises a first heavy chain variable region (VHa) and a first light chain variable region (VLa), and the second antibody or antigen-binding fragment thereof comprises a second heavy chain variable region (VHb) and a second light chain variable region (VLb);

(b) determining the amino acid sequence of VHa, VLa, VHb, and VLb;
(c) aligning the amino acid sequences of VLa and VLb and determining the sequence homology between VLa and VLb is less than 80%;
(d) replacing all light chain variable regions in a phage display antibody library with a plurality of light chain variable regions. In some embodiments, the light chain variables regions are at least 80%, 85%, 90%, 95%, or 99% identical to VLa or VLb;
(e) panning against the second antigen;
(f) selecting a common light chain variable region (VLc), and a third heavy chain variable region (VHc). In some embodiments, VHc-VLc binds to the second antigen with a desired affinity;
(g) determining the homology between VLa and VLc is greater than 80%;
(h) designing a common light chain variable region (VLd). In some embodiments, the VLd, when it associates with VHa, maintains the affinity to the first antigen and when it associates with VHc, has desired affinity to the second antigen;
(i) optionally, redesigning the VHa and VHc sequences, thereby obtaining VHa' and VHc' to increase the difference of biochemical or biophysical characteristics between a first protein comprising two polypeptides each comprising VHa' and two polypeptides each comprising VLd, and a second protein comprising two polypeptides each comprising VHc' and two polypeptides each comprising VLd; and
(j) optionally producing a bispecific antibody or antigen-binding fragment thereof that has two light chain variable regions and two heavy chain variable regions. In some embodiments, the two light variable regions each comprises VLd, and the two heavy chain variable regions comprise VHa' and VHc' respectively.

In one aspect, the disclosure provides methods of making bispecific antibody or antigen-binding fragment thereof. The methods involve one or more of the following steps:
(a) selecting a first antigen and a second antigen, and identifying a first antibody or antigen-binding fragment thereof that binds to the first antigen and a second antibody or antigen-binding fragment thereof that binds to the second antigen. In some embodiments, the first antibody or antigen-binding fragment thereof comprises a first heavy chain variable region (VHa) and a first light chain variable region (VLa), and the second antibody or antigen-binding fragment thereof comprises a second heavy chain variable region (VHb) and a second light chain variable region (VLb);
(b) determining the amino acid sequence of VHa, VLa, VHb, and VLb;
(c) aligning the amino acid sequences of VLa and VLb and determining that the sequence homology between VLa and VLb is greater than 80%;
(d) designing a common light chain variable region (VLc). In some embodiments, the VLc, when it associates with VHa, maintains the affinity to the first antigen; and
(e) optionally, producing a bispecific antibody or antigen-binding fragment thereof that has two light chain variable regions and two heavy chain variable regions. In some embodiments, the two light variable regions each comprises VLc, and the two heavy chain variable regions comprise VHa and VHb respectively.

In one aspect, the disclosure also provides methods of making bispecific antibody or antigen-binding fragment thereof. The methods involve one or more of the following steps:
(a) selecting a first antigen and a second antigen, and identifying a first antibody or antigen-binding fragment thereof that binds to the first antigen and a second antibody or antigen-binding fragment thereof that binds to the second antigen. In some embodiments, the first antibody or antigen-binding fragment thereof comprises a first heavy chain variable region (VHa) and a first light chain variable region (VLa), and the second antibody or antigen-binding fragment thereof comprises a second heavy chain variable region (VHb) and a second light chain variable region (VLb);
(b) determining the amino acid sequence of VHa, VLa, and VLb;
(c) aligning the amino acid sequences of VLa and VLb and determining the sequence homology between VLa and VLb is less than 80%;
(d) replacing all light chain variable regions in a phage display antibody library with the VLa, and panning against the second antigen to obtain a third heavy chain variable region (VHc); and
(e) optionally, producing a bispecific antibody or antigen-binding fragment thereof that has two light chain variable regions and two heavy chain variable regions. In some embodiments, the two light variable regions each comprises VLa, and the two heavy chain variable regions comprise VHa and VHc respectively.

In one aspect, the disclosure further provides methods of making bispecific antibody or antigen-binding fragment thereof. The methods involve one or more of the following steps:
(a) selecting a first antigen and a second antigen, and identifying a first antibody or antigen-binding fragment thereof that binds to the first antigen and a second antibody or antigen-binding fragment thereof that binds to the second antigen. In some embodiments, the first antibody or antigen-binding fragment thereof comprises a first heavy chain variable region (VHa) and a first light chain variable region (VLa), and the second antibody or antigen-binding fragment thereof comprises a second heavy chain variable region (VHb) and a second light chain variable region (VLb);
(b) determining the amino acid sequence of VHa, VLa, VHb, and/or VLb;
(c) aligning the amino acid sequences of VLa and VLb and determining the sequence homology between VLa and VLb is less than 80%;
(d) replacing all light chain variable regions in a phage display antibody library with a plurality of light chain variable regions. In some embodiments, the light chain variables regions are at least 80%, 85%, 90%, 95%, or 99% identical to VLa or VLb;
(e) panning against the first and/or the second antigen;
(f) selecting a common light chain variable region (VLc), and a third heavy chain variable region (VHc). In some embodiments, VHa-VLc binds to the first antigen with a desired affinity and VHc-VLc binds to the second antigen with a desired affinity; and
(g) optionally, producing a bispecific antibody or antigen-binding fragment thereof that has two light chain variable regions and two heavy chain variable regions. In some embodiments, the two light variable regions each comprises VLc, and the two heavy chain variable regions comprise VHa and VHc respectively.

In another aspect, the disclosure provides an antibody or antigen-binding fragment thereof that binds to CD3 comprising: a heavy chain variable region (VH) comprising complementarity determining regions (CDRs) 1, 2, and 3, wherein the VH CDR1 region comprises an amino acid sequence that is at least 80% identical to a selected VH CDR1 amino acid sequence, the VH CDR2 region comprises an amino acid sequence that is at least 80% identical to a selected VH CDR2 amino acid sequence, and the VH CDR3 region comprises an amino acid sequence that is at least 80% identical to a selected VH CDR3 amino acid sequence; and a light chain variable region (VL) comprising CDRs 1, 2, and 3, wherein the VL CDR1 region comprises an amino acid sequence that is at least 80% identical to a selected VL CDR1 amino acid sequence, the VL CDR2 region comprises an amino acid sequence that is at least 80% identical to a selected VL CDR2 amino acid sequence, and the VL CDR3 region comprises an amino acid sequence that is at least 80% identical to a selected VL CDR3 amino acid sequence, wherein the selected VH CDRs 1, 2, and 3 amino acid sequences and the selected VL CDRs, 1, 2, and 3 amino acid sequences are one of the following: the selected VH CDRs 1, 2, 3 amino acid sequences are set forth in SEQ ID NOs: 22-24, respectively, and the selected VL CDRs 1, 2, 3 amino acid sequences are set forth in SEQ ID NOs: 28-30, respectively.

In some embodiments, the VH comprises CDRs 1, 2, 3 with the amino acid sequences set forth in SEQ ID NOs: 22, 23, 24 respectively, and the VL comprises CDRs 1, 2, 3 with the amino acid sequences set forth in SEQ ID NOs: 28, 29, 30, respectively.

In some embodiments, the antibody or antigen-binding fragment specifically binds to human CD3.

In some embodiments, the antibody or antigen-binding fragment is a bispecific antibody.

In another aspect, the present disclosure also provides an antibody or antigen-binding fragment thereof that binds to PD-L1 comprising: a heavy chain variable region (VH) comprising complementarity determining regions (CDRs) 1, 2, and 3, wherein the VH CDR1 region comprises an amino acid sequence that is at least 80% identical to a selected VH CDR1 amino acid sequence, the VH CDR2 region comprises an amino acid sequence that is at least 80% identical to a selected VH CDR2 amino acid sequence, and the VH CDR3 region comprises an amino acid sequence that is at least 80% identical to a selected VH CDR3 amino acid sequence; and a light chain variable region (VL) comprising CDRs 1, 2, and 3, wherein the VL CDR1 region comprises an amino acid sequence that is at least 80% identical to a selected VL CDR1 amino acid sequence, the VL CDR2 region comprises an amino acid sequence that is at least 80% identical to a selected VL CDR2 amino acid sequence, and the VL CDR3 region comprises an amino acid sequence that is at least 80% identical to a selected VL CDR3 amino acid sequence, wherein the selected VH CDRs 1, 2, and 3 amino acid sequences and the selected VL CDRs, 1, 2, and 3 amino acid sequences are one of the following:
(1) the selected VH CDRs 1, 2, 3 amino acid sequences are set forth in SEQ ID NOs: 41-43, respectively, and the selected VL CDRs 1, 2, 3 amino acid sequences are set forth in SEQ ID NOs: 53-55, respectively;
(2) the selected VH CDRs 1, 2, 3 amino acid sequences are set forth in SEQ ID NOs: 41-43, respectively, and the selected VL CDRs 1, 2, 3 amino acid sequences are set forth in SEQ ID NOs: 59-61, respectively;

In some embodiments, the VH comprises CDRs 1, 2, 3 with the amino acid sequences set forth in SEQ ID NOs: 41-43 respectively, and the VL comprises CDRs 1, 2, 3 with the amino acid sequences set forth in SEQ ID NOs: 59-61, respectively.

In some embodiments, the antibody or antigen-binding fragment specifically binds to human CD3. In some embodiments, the antibody or antigen-binding fragment is a bispecific antibody.

In another aspect, the disclosure provides an antibody or antigen-binding fragment thereof that binds to CD55 comprising:
a heavy chain variable region (VH) comprising complementarity determining regions (CDRs) 1, 2, and 3, wherein the VH CDR1 region comprises an amino acid sequence that is at least 80% identical to a selected VH CDR1 amino acid sequence, the VH CDR2 region comprises an amino acid sequence that is at least 80% identical to a selected VH CDR2 amino acid sequence, and the VH CDR3 region comprises an amino acid sequence that is at least 80% identical to a selected VH CDR3 amino acid sequence; and a light chain variable region (VL) comprising CDRs 1, 2, and 3, wherein the VL CDR1 region comprises an amino acid sequence that is at least 80% identical to a selected VL CDR1 amino acid sequence, the VL CDR2 region comprises an amino acid sequence that is at least 80% identical to a selected VL CDR2 amino acid sequence, and the VL CDR3 region comprises an amino acid sequence that is at least 80% identical to a selected VL CDR3 amino acid sequence, wherein the selected VH CDRs 1, 2, and 3 amino acid sequences and the selected VL CDRs, 1, 2, and 3 amino acid sequences are one of the following:
(1) the selected VH CDRs 1, 2, 3 amino acid sequences are set forth in SEQ ID NOs: 47-49, respectively, and the selected VL CDRs 1, 2, 3 amino acid sequences are set forth in SEQ ID NOs: 53-55, respectively;
(2) the selected VH CDRs 1, 2, 3 amino acid sequences are set forth in SEQ ID NOs: 47-49, respectively, and the selected VL CDRs 1, 2, 3 amino acid sequences are set forth in SEQ ID NOs: 59-61, respectively.

In some embodiments, the VH comprises CDRs 1, 2, 3 with the amino acid sequences set forth in SEQ ID NOs: 47-49 respectively, and the VL comprises CDRs 1, 2, 3 with the amino acid sequences set forth in SEQ ID NOs: 59-61, respectively.

In some embodiments, the antibody or antigen-binding fragment specifically binds to human CD3.

In some embodiments, the antibody or antigen-binding fragment is a bispecific antibody.

In one aspect, the disclosure provides a nucleic acid comprising a polynucleotide encoding a polypeptide comprising: an immunoglobulin light chain or a fragment thereof comprising a VL comprising CDRs 1, 2, and 3 comprising the amino acid sequences set forth in SEQ ID NOs: 53-55, respectively. In some embodiments, the VL, when paired with a VH comprising the amino acid sequence set forth in SEQ ID NO: 4 binds to PD-L1, and/or when paired with a VH comprising the amino acid sequence set forth in SEQ ID NO: 5 binds to CD55.

In one aspect, the disclosure provides a nucleic acid comprising a polynucleotide encoding a polypeptide comprising: an immunoglobulin light chain or a fragment thereof comprising a VL comprising CDRs 1, 2, and 3 comprising the amino acid sequences set forth in SEQ ID NOs: 59-61, respectively. In some embodiments, the VL, when paired with a VH comprising the amino acid sequence set forth in SEQ ID NO: 4 binds to PD-L1, and/or when paired with a VH comprising the amino acid sequence set forth in SEQ ID NO: 5 binds to CD55.

In some embodiments, the nucleic acid encodes a bispecific antibody. In some embodiments, the nucleic acid is cDNA.

In one aspect, the disclosure provides a vector comprising one or more of the nucleic acids described herein.

In one aspect, the disclosure provides a cell comprising the vector described herein. In some embodiments, the cell is a CHO cell.

In one aspect, the disclosure provides a cell comprising one or more of the nucleic acids described herein.

In one aspect, the disclosure provides a bispecific antibody or antigen-binding fragment thereof that binds to CD20 and CD3 comprising a first polypeptide comprising a first heavy chain variable region (VH) comprising an amino acid sequence that is at least 90%, 95%, 96%, 97%, 98%, or 99% identical to SEQ ID NO: 1; a second polypeptide comprising a second heavy chain variable region (VH) comprising an amino acid sequence that is at least 90%, 95%, 96%, 97%, 98%, or 99% identical to SEQ ID NO: 2; a third polypeptide comprising a first light chain variable region (VL) comprising an amino acid sequence that is at least 90%, 95%, 96%, 97%, 98%, or 99% identical to SEQ ID NO: 3; a fourth polypeptide comprising a second light chain variable region (VL) comprising an amino acid sequence that is at least 90%, 95%, 96%, 97%, 98%, or 99% identical to SEQ ID NO: 3.

In some embodiments, the first heavy chain variable region (VH) comprises SEQ ID NO: 1; the second heavy chain variable region (VH) comprise SEQ ID NO: 2; the first light chain variable region (VL) comprise SEQ ID NO: 3; and the second light chain variable region (VL) comprises SEQ ID NO: 3.

In some embodiments, the first polypeptide comprises an amino acid sequence that is at least 90%, 95%, 96%, 97%, 98%, or 99% identical to SEQ ID NO: 34, 35, or 36; the second polypeptide comprises an amino acid sequence that is at least 90%, 95%, 96%, 97%, 98%, or 99% identical to SEQ ID NO: 37, 38, or 39; the third polypeptide comprises an amino acid sequence that is at least 90%, 95%, 96%, 97%, 98%, or 99% identical to SEQ ID NO: 40; and the fourth polypeptide comprises an amino acid sequence that is at least 90%, 95%, 96%, 97%, 98%, or 99% identical to SEQ ID NO: 40.

In some embodiments, the first polypeptide comprises an amino acid sequence that is set forth in SEQ ID NO: 35; and the second polypeptide comprises an amino acid sequence that is set forth in SEQ ID NO: 38.

In one aspect, the disclosure provides a bispecific antibody or antigen-binding fragment thereof that binds to PD-L1 and CD55 comprising a first polypeptide comprising a first heavy chain variable region (VH) comprising an amino acid sequence that is at least 90%, 95%, 96%, 97%, 98%, or 99% identical to SEQ ID NO: 4; a second polypeptide comprising a second heavy chain variable region (VH) comprising an amino acid sequence that is at least 90%, 95%, 96%, 97%, 98%, or 99% identical to SEQ ID NO: 5; a third polypeptide comprising a first light chain variable region (VL) comprising an amino acid sequence that is at least 90%, 95%, 96%, 97%, 98%, or 99% identical to SEQ ID NO: 6 or 7; a fourth polypeptide comprising a second light chain variable region (VL) comprising an amino acid sequence that is at least 90%, 95%, 96%, 97%, 98%, or 99% identical to SEQ ID NO: 6 or 7.

In some embodiments, the first heavy chain variable region (VH) comprises SEQ ID NO: 4; the second heavy chain variable region (VH) comprise SEQ ID NO: 5; the first light chain variable region (VL) comprise SEQ ID NO: 7; and the second light chain variable region (VL) comprises SEQ ID NO: 7.

In some embodiments, the first polypeptide comprises an amino acid sequence that is at least 90%, 95%, 96%, 97%, 98%, or 99% identical to SEQ ID NO: 65; the second polypeptide comprises an amino acid sequence that is at least 90%, 95%, 96%, 97%, 98%, or 99% identical to SEQ ID NO: 66; the third polypeptide comprises an amino acid sequence that is at least 90%, 95%, 96%, 97%, 98%, or 99% identical to SEQ ID NO: 67 or 68; and the fourth polypeptide comprises an amino acid sequence that is at least 90%, 95%, 96%, 97%, 98%, or 99% identical to SEQ ID NO: 67 or 68.

In some embodiments, the first polypeptide comprises an amino acid sequence that is set forth in SEQ ID NO: 65; the second polypeptide comprises an amino acid sequence that is set forth in SEQ ID NO: 66; the third polypeptide comprises an amino acid sequence that is set forth in SEQ ID NO: 68; and the fourth polypeptide comprises an amino acid sequence that is set forth in SEQ ID NO: 68.

In one aspect, the disclosure provides an antibody-drug conjugate comprising the antibody or antigen-binding fragment thereof described herein covalently bound to a therapeutic agent. In some embodiments, the therapeutic agent is a cytotoxic or cytostatic agent.

In one aspect, the disclosure provides methods of treating a subject having cancer. The methods involve administering a therapeutically effective amount of a composition comprising the antibody or antigen-binding fragment thereof described herein, or the antibody-drug conjugate described herein, to the subject. In some embodiments, the subject has a solid tumor. In some embodiments, the cancer is melanoma, pancreatic carcinoma, or a hematological malignancy. In some embodiments, the cancer is Non-Hodgkin's lymphoma, lymphoma, or chronic lymphocytic leukemia.

In one aspect, the disclosure provides methods of decreasing the rate of tumor growth. The methods involve contacting a tumor cell with an effective amount of a composition comprising an antibody or antigen-binding fragment thereof described herein, or the antibody-drug conjugate described herein, to the subject.

In one aspect, the disclosure provides methods of killing a tumor cell. The methods involve contacting a tumor cell with an effective amount of a composition comprising the antibody or antigen-binding fragment thereof described herein, or the antibody-drug conjugate described herein, to the subject.

In one aspect, the disclosure provides a pharmaceutical composition comprising the antibody or antigen-binding fragment thereof described herein, and a pharmaceutically acceptable carrier.

In one aspect, the disclosure provides a pharmaceutical composition comprising the antibody drug conjugate described herein, and a pharmaceutically acceptable carrier.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 24. The alignment for common light chain for BsMab v1 (SEQ IN NO: 67) and common light chain for BsMab v2 (SEQ ID NO: 68). The majority sequence (SEQ ID NO: 69) is shown on the top.

FIG. 29 is a schematic diagram showing how a bispecific antibody that binds to a cancer specific antigen and a cancer-associated antigen can recognize and kill a tumor cell.

SEQUENCE LISTING

The instant application contains a Sequence Listing which has been submitted electronically in ASCII format and is hereby incorporated by reference in its entirety. Said ASCII copy, created on Jul. 26, 2022 is named "44836-0002US1_ST25.txt" and is 67,161 bytes in size.

DETAILED DESCRIPTION

A bispecific antibody or antigen-binding fragment thereof is an artificial protein that can simultaneously bind to two different types of antigens. In some embodiments, a bispecific antibody or antigen-binding fragment thereof can have two arms (Arms A and B). Each arm has one heavy chain variable region and one light chain variable region.

The bispecific antibody or antigen-binding fragment thereof can be IgG-like and non-IgG-like. The IgG-like bispecific antibody can have two Fab arms and one Fc region, and the two Fab arms bind to different antigens. The non-IgG-like bispecific antibody or antigen-binding fragment can be e.g., chemically linked Fabs (e.g., two Fab regions are chemically linked), and single-chain variable fragments (scFVs). For example, a scFV can have two heavy chain variable regions and two light chain variable regions.

In an imbalanced bispecific antibody or antigen-binding fragment thereof, the two arms (Arms: A and B) or the two antigen binding regions (Antigen binding regions: A and B) can bind to the respective target antigens with different affinities. The binding affinities can be expressed by the association constant (Ka):

$$Ka=[\text{Antibody-Antigen}]/[\text{Antibody}][\text{Antigen}]$$

Antibodies with high affinity usually have Ka>$10^7$ M$^{-1}$. The Ka for one arm or one antigen binding region can be greater than $10^5$ M$^{-1}$, $10^6$ M$^{-1}$, $10^7$ M$^{-1}$, $10^8$ M$^{-1}$, $10^9$ M$^{-1}$, $10^{10}$ M$^{-1}$, $10^{11}$ M$^{-1}$, or $10^{12}$ M$^{-1}$. In some embodiments, the Ka can be less than $10^5$ M$^{-1}$, $10^6$ M$^{-1}$, $10^7$ M$^{-1}$, $10^8$ M$^{-1}$, $10^9$ M$^{-1}$, $10^{10}$ M$^{-1}$, $10^{11}$ M$^{-1}$, or $10^{12}$ M$^{-1}$.

Figure 28:
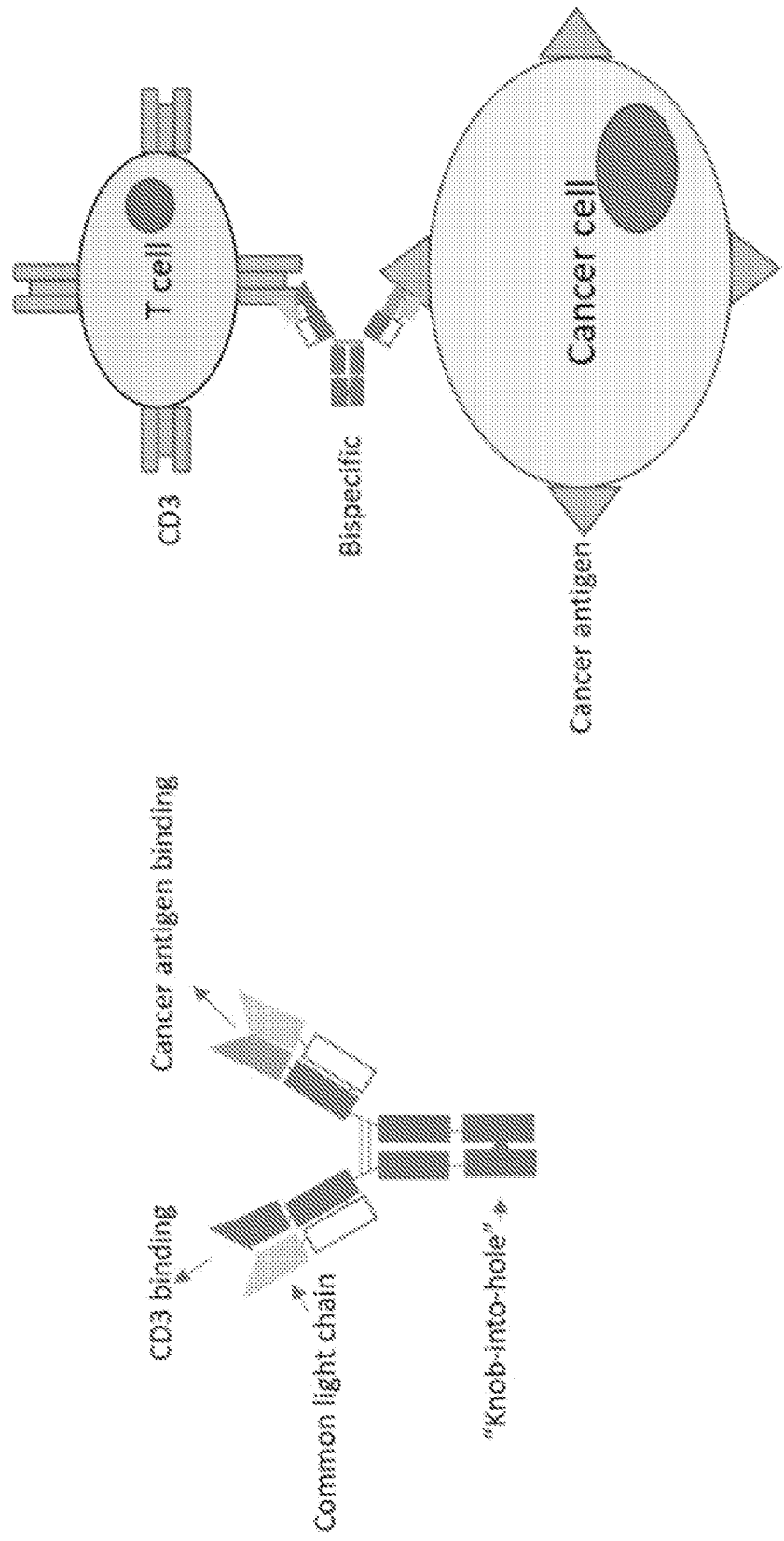
FIG. 28 is a schematic diagram showing how a bispecific antibody that binds to CD3 and a cancer antigen (e.g., cancer specific antigen) can recognize and kill a tumor cell.

The binding affinity of the first arm or the first antigen binding region (A) can be greater than the binding affinity of the second arm or the second antigen binding region (B). Bispecific antibodies with imbalanced affinities can have various advantages. For example, bispecific antibodies with imbalanced affinities can be used to target a cancer specific antigen on cancer cells and CD3 on T cell. In this case, high affinity to the cancer specific antigen can lead to better capturing of cancer cells by T cells, and low affinity to CD3 can avoid triggering T-cell signaling by CD3 (FIG. 28). Only when the bispecific antibody is presented to the T cell in a multivalent fashion by a target cancer cell, can the T cell be activated and kill the target cancer cell. Furthermore, the bispecific antibodies with imbalanced affinities can also be used to target a cancer specific antigen and a cancer-associated antigen (FIG. 29). In this case, the bispecific antibody only weakly binds to non-cancer cells expressing low level of cancer-associated antigens, but strongly binds to cancer cells expressing both cancer specific antigens and high level of cancer-associated antigens.

For a bispecific antibody with imbalanced affinities, the Ka for the first arm or the first antigen binding region (A) can be greater than $10^7$ M$^{-1}$, $10^8$ M$^{-1}$, $10^9$ M$^{-1}$, $10^{10}$ M$^{-1}$, $10^{11}$ M$^{-1}$, or $10^{12}$ M$^{-1}$. In some embodiments, the Ka for the first arm or the first antigen binding region (A) can be 10, 100, 1000, 10000, or 100000 times greater than the Ka for the second arm or the second antigen binding region (B). Thus, in some embodiments, the Ka for the second arm or the second antigen binding region (B) can be less than $10^5$ M$^{-1}$, $10^6$ M$^{-1}$, $10^7$ M$^{-1}$, $10^8$ M$^{-1}$, or $10^9$ M$^{-1}$.

In some embodiments, the Ka for the second arm or the second antigen binding region (B) still specifically binds to the target antigen with a reasonable affinity, e.g., greater than $10^4$ M$^{-1}$, $10^5$ M$^{-1}$ or $10^6$ M$^{-1}$.

The binding affinity can also be expressed by the dissociation constant (Kd).

$$Kd=[Antibody][Antigen]/[Antibody-Antigen]$$

The Kd can be less than $10^{-5}$ M, $10^{-6}$ M, $10^{-7}$ M, $10^{-8}$ M, $10^{-9}$ M, $10^{-10}$ M, $10^{-11}$ M, or $10^{-12}$ M. In some embodiments, the Kd can be greater than $10^{-5}$ M, $10^{-6}$ M, $10^{-7}$ M, $10^{-8}$ M, $10^{-9}$ M, $10^{-10}$ M, $10^{-11}$ M, or $10^{-12}$ M.

In some embodiments, the binding affinity of the first arm or the first antigen binding region (A) is greater than the binding affinity of the second arm or the second antigen binding region (B). For example, the Kd for the second arm or the second antigen binding region (B) can be 10, 100, 1000, 10000, or 100000 times greater (thus with less affinity) than the Kd for the first arm or the first antigen binding region (A). Thus, in some embodiments, the Kd for the first arm or the first antigen binding region (A) can be less than $10^{-7}$ M, $10^{-8}$ M, $10^{-9}$ M, $10^{-10}$ M, $10^{-11}$ M, or $10^{-12}$ M; and the Kd for the second arm or the second antigen binding region (B) can be greater than $10^{-5}$ M, $10^{-6}$ M, $10^{-7}$ M, $10^{-8}$ M, or $10^{-9}$ M.

In some embodiments, the bispecific antibody or antigen-binding fragment thereof comprises two light chains and two heavy chains. Each of the two light chains has one light chain variable region (VL) and one light chain constant region (CL). Each of the two heavy chains has one heavy chain variable region (VH) and three heavy chain constant regions (CH1, CH2, and CH3). In some embodiments, the two light chains for Arm A and Arm B are the same. Thus, the CDRs in the VL of two light chains can be the same. In some embodiments, the two heavy chains in the bispecific antibody or antigen-binding fragment thereof are different. Thus, the CDRs in the VH of two heavy chains are different.

Various methods can be used to ensure that the same heavy chains do not associate with each other when making the bispecific antibodies. For example, the "knobs into holes" approach introduces a mutation for an amino acid with a large sidechain in one heavy chain, and a mutation for an amino acid with a small sidechain in the other heavy chain. Thus, the same heavy chains are less likely to associate with each other and the two different heavy chains have a higher chance to associate with each other. The "knobs into holes" approaches are described, e.g., in Ridgway, John B B, Leonard G. Presta, and Paul Carter. "'Knobs-into-holes' engineering of antibody CH3 domains for heavy chain heterodimerization." *Protein Engineering, Design and Selection* 9.7 (1996), which is incorporated herein by reference in its entirety.

Imbalanced Bispecific Antibodies that Bind to T Cell Specific Antigen and Cancer Antigens Bispecific antibodies (BsAb or BsMab) with a T cell specific antigen (e.g., CD3, CD4, or CD8) binding arm that can recruit and activate T cells have been widely studied for cancer therapy. However, the effector function of many of these bispecific antibodies are eliminated because of safety concerns. Because an antibody's effector function such as ADCC and CDC have been shown to play a critical role in cancer cell killing, "safely" maintaining an antibody's effector function would expand the mechanisms of action of an therapeutic antibody as well as improve the antibody's cancer killing function. To "safely" maintain the effector functions and expand the applications of these bispecific antibodies, an imbalanced bispecific antibody technology platform has been developed based on computational antibody design.

In this design, the first antigen binding region targets a cancer specific antigen, and the second antigen binding region targets a T cell specific antigen (e.g., CD3, CD4, or CD8) to recruit T cell to attack cancer with the cancer specific antigen (FIG. 28).

As used herein, the term "cancer specific antigen" refers to antigens that are specifically expressed on cancer cell surfaces. These antigens can be used to identify tumor cells. Normal cells rarely express cancer specific antigens. Some exemplary cancer specific antigens include, e.g., CD20, PSA, PSCA, PD-L1, Her2, Her3, Her1, β-Catenin, CD19, CEACAM3, EGFR, c-Met, EPCAM, PSMA, CD40, MUC1, and IGF1R, etc. PSA are primarily expressed on prostate cancer cells, and Her2 are primarily expressed on breast cancer cells.

A bispecific antibody that binds to CD20 and CD3 is provided in this disclosure. This bispecific antibody can be applied to target multiple CD20 positive cancers such as CD20-positive non-Hodgkin's lymphoma (NHL), thus can be used to treat non-Hodgkin's lymphoma in a subject. Because the bispecific antibody applies different mechanism of action to treat cancer compared to therapeutic antibodies target CD20 alone, it can be applied as a complementary therapy for CD20 positive cancers, especially for those CD20 positive cancers which don not respond well to current CD20 therapies (such has rituximab-resistant NHL).

An antibody with high affinity to CD3 can trigger T-cell signaling, and cause undesirable immune response. Thus, a low affinity (e.g., Ka can be less than $10^5$ M$^{-1}$, $10^6$ M$^{-1}$, or $10^7$ M$^{-1}$) to CD3 is required to reduce the risk of triggering T-cell signaling by CD3 while "safely" maintaining the antibody's effector function. As used herein, the term "safely maintaining the antibody's effector function" means that the antibody does not induce ADCC or CDC on normal cells (e.g., non-cancer cells). When multiple bispecific antibodies are presented on a target cancer cells (e.g., in a cluster) and bridge the interaction between cancer cell and T cell, these bispecific antibodies can trigger T-cell signaling though CD3 in a multivalent fashion, and the activated T cells will then kill the target cancer cells.

Therefore, the disclosure provides bispecific antibody or antigen-binding fragment thereof comprising two heavy chain variable regions and two light chain variable regions, wherein the first heavy chain variable region comprises a sequence that is at least 80%, 85%, 90%, 91%, 92%, 93%, 94%, 95%, 96%, 97%, 98%, or 99% identical to SEQ ID NO: 1, the second heavy chain variable region comprises a sequence that is at least 80%, 85%, 90%, 91%, 92%, 93%, 94%, 95%, 96%, 97%, 98%, or 99% identical to SEQ ID NO: 2, and the first and the second light chain variable regions comprise a sequence that is at least 80%, 85%, 90%, 91%, 92%, 93%, 94%, 95%, 96%, 97%, 98%, or 99% identical to SEQ ID NO: 3.

In some embodiments, the CDR sequences for binding to CD20 include CDRs of the heavy chain variable domain, SEQ ID NOs: 16-18, and CDRs of the light chain variable domain, SEQ ID NOs: 28-30, as defined by Kabat numbering. Under Chothia numbering, the CDR sequences of the heavy chain variable domain are set forth in SEQ ID NOs: 19-21, and CDRs of the light chain variable domain are set forth in SEQ ID NOs: 31-33.

In some embodiments, the CDR sequences for binding to CD3 include CDRs of the heavy chain variable domain, SEQ ID NOs: 22-24, and CDRs of the light chain variable domain, SEQ ID NOs: 28-30, as defined by Kabat numbering. Under Chothia numbering, the CDR sequences of the heavy chain variable domain are set forth in SEQ ID NOs: 25-27, and CDRs of the light chain variable domain are set forth in SEQ ID NOs: 31-33.

In some embodiments, the bispecific antibody or antigen-binding fragment thereof comprises a first heavy chain amino acid sequence that is at least 80%, 85%, 90%, 91%, 92%, 93%, 94%, 95%, 96%, 97%, 98%, or 99% identical to SEQ ID NO: 34, 35, or 36; a second heavy chain amino acid sequence that is at least 80%, 85%, 90%, 91%, 92%, 93%, 94%, 95%, 96%, 97%, 98%, or 99% identical to SEQ ID NO: 37, 38, or 39; a first light chain amino acid sequence that is at least 80%, 85%, 90%, 91%, 92%, 93%, 94%, 95%, 96%, 97%, 98%, or 99% identical to SEQ ID NO: 40; and a second light chain amino acid sequence that is at least 80%, 85%, 90%, 91%, 92%, 93%, 94%, 95%, 96%, 97%, 98%, or 99% identical to SEQ ID NO: 40. In some embodiments, the first light chain amino acid sequence and the second light chain amino acid sequence are identical.

Imbalanced Bispecific Antibodies that Bind to Cancer Specific Antigens and Cancer-Associated Antigen.

The present disclosure also provides imbalanced bispecific antibodies that have the first antigen binding region targets a cancer specific antigen, and the second antigen binding region targets a cancer-associated antigen.

As used herein, the term "cancer-associated antigen" refers to antigens that are expressed at a relatively high level on cancer cells but may be also expressed at a relatively low level on normal cells. CD55, CD59, CD46 and many adhesion molecules such as N-cadherin, VE-cadherin, NCAM, Mel-CAM, ICAM, NrCAM, VCAM1, ALCAM, MCAM, etc., are cancer-associated antigens. While both cancer specific antigen and cancer-associated antigen are expressed on cancer cell surface, the difference between a cancer specific antigen and a cancer-associated antigen is that the cancer-associated antigen is also expressed on normal cells, but at a relative low level as compared to the level on cancer cells. In contrast, a cancer specific antigen is rarely expressed on normal cells, and even if it is expressed on normal cells, the amount is extremely low. An antibody that targets cancer specific antigen usually will not induce Antibody-dependent Cellular Cytotoxicity (ADCC) or Complement-dependent cytotoxicity (CDC) on normal cells. In contrast, an antibody that targets a cancer-associated antigen with a high affinity may cause cytotoxic effects among normal cells. Thus, it is important that the bispecific antibody binds to a cancer-associated antigen with a relatively low affinity (FIG. 29).

A bispecific antibody that binds to PD-L1 and CD55 is provided in the examples. This antibody can be used for treating a subject with PD-L1 and CD55 positive cancers though ADCC or CDC as well as blocking the PD-L1/PD1 interaction to activate T cell dependent immune response and to decrease CD55's repression on CDC. Furthermore, as cancer cells may become resistant to PD-L1 antibodies, the binding between the second arm and CD55 on the cancer cells can provide additional therapeutic effects.

Therefore, the disclosure provides bispecific antibody or antigen-binding fragment thereof comprising two heavy chain variable regions and two light chain variable regions, wherein the first heavy chain variable region comprises a sequence that is at least 80%, 85%, 90%, 91%, 92%, 93%, 94%, 95%, 96%, 97%, 98%, or 99% identical to SEQ ID NO: 4, the second heavy chain variable region comprises a sequence that is at least 80%, 85%, 90%, 91%, 92%, 93%, 94%, 95%, 96%, 97%, 98%, or 99% identical to SEQ ID NO: 5, and the first and the second light chain variable regions comprise a sequence that is at least 80%, 85%, 90%, 91%, 92%, 93%, 94%, 95%, 96%, 97%, 98%, or 99% identical to SEQ ID NO: 6 or 7.

In some embodiments, the CDR sequences for binding to PD-L1 include CDRs of the heavy chain variable domain, SEQ ID NOs: 41-43, and CDRs of the light chain variable domain, SEQ ID NOs: 53-55 or 59-61, as defined by Kabat numbering. Under Chothia numbering, the CDR sequences of the heavy chain variable domain are set forth in SEQ ID NOs: 44-46, and CDRs of the light chain variable domain are set forth in SEQ ID NOs: 56-58 or 62-64.

In some embodiments, the CDR sequences for binding to CD55 include CDRs of the heavy chain variable domain, SEQ ID NOs: 47-49, and CDRs of the light chain variable domain, SEQ ID NOs: 53-55 or 59-61, as defined by Kabat numbering. Under Chothia numbering, the CDR sequences of the heavy chain variable domain are set forth in SEQ ID NOs: 50-52, and CDRs of the light chain variable domain are set forth in SEQ ID NOs: 56-58 or 62-64.

In some embodiments, the bispecific antibody or antigen-binding fragment thereof comprises a first heavy chain amino acid sequence that is at least 80%, 85%, 90%, 91%, 92%, 93%, 94%, 95%, 96%, 97%, 98%, or 99% identical to SEQ ID NO: 65; a second heavy chain amino acid sequence that is at least 80%, 85%, 90%, 91%, 92%, 93%, 94%, 95%, 96%, 97%, 98%, or 99% identical to SEQ ID NO: 66; a first light chain amino acid sequence that is at least 80%, 85%, 90%, 91%, 92%, 93%, 94%, 95%, 96%, 97%, 98%, or 99% identical to SEQ ID NO: 67 or 68; and a second light chain amino acid sequence that is at least 80%, 85%, 90%, 91%, 92%, 93%, 94%, 95%, 96%, 97%, 98%, or 99% identical to SEQ ID NO: 67 or 68. In some embodiments, the first light chain amino acid sequence and the second light chain amino acid sequence are identical.

Making an Imbalance Bispecific Antibody or Antigen or Antigen-Binding Fragment Thereof The bispecific antibody or antigen or antigen-binding fragment thereof can be made by the following methods:

1) Select two target antigens and determine the heavy chain variable region sequence (VHa) and the light chain variable region sequence (VLa) of an antibody (Antibody A) that binds to the first antigen, and determine the heavy chain variable region sequence (VHb) and the light chain variable region sequence (VLb) of an antibody (Antibody B) that binds to the second antigen.

2) Align the VLa and VLb, if the sequence homology is more than 80%, design a common VL by using computer modeling tools (such as BioLuminate from Schordingerm, Cambridge, MA). During the design process, try to maintain VLa's affinity but can sacrifice VLb's affinity to some extent. The common VL can be VLa, VLb itself or a new VLc of which the sequence share high homology to VLa and VLb. The 3D structure of the VLa and VLb can be determined, e.g., from structure modeling or crystal structure. The process can start with the sequence of VLa. If based on the 3D structure, an amino acid in the light chain is identified to be important for binding to the second antigen (e.g., when it is paired with VHb), and not involved in the binding with the first antigen (e.g., when it is paired with VHa), then the amino acid in VLa can be changed to the corresponding amino acid in VLb. After repeating this process several times, a common VLc can be obtained.

3) If the homology of VLa and VLb is less than 80%, make a human ScFV or Fab phage library by replacing the VLs of an existing human naïve ScFV library with the VL of Antibody A, then use error prone PCR to induce less than 20% of nucleic tide mutations into VL, panning against Antibody B's antigen to get a new Antibody B' with VLa or its homologue (with >80% homology) as its VL. If the VL is not VLa, but a VLa homologue (e.g., with >80% homology), step 2) is repeated to design a common VL.
4) Use computer modeling tools to re-design VHa and VHb sequence respectively in order to increase the difference of A and B's biochemical and biophysical characteristics (such as 3D isoelectric point (PI)). During this process, A's affinity cannot be reduced and B's affinity can be reduced to some extent.
5) Develop a buffer system to purify the imbalanced bispecific antibody.

The isoelectric point (PI) of a peptide is the pH at which a particular molecule carries no net electrical charge in the statistical mean. Amino acids that make up a peptide may be positive, negative, neutral, or polar in nature, and together give a protein its overall charge. However, certain amino acids in a protein are buried in the protein and will have no interaction with the solution surrounding it. The 3D PI takes the 3D structure of the protein into account, and provides a better estimate of the pH value at which a protein, when it is properly folded, carries no net electrical charge in the statistical mean. (We used a gradient pH buffer from a publication, so the buffer is not our invention. But we still need to optimize purification process).

In some embodiments, the bispecific antibody or antigen or antigen-binding fragment thereof can also be made by the following methods:

(a) selecting a first antigen and a second antigen, and identifying a first antibody or antigen-binding fragment thereof that binds to the first antigen and a second antibody or antigen-binding fragment thereof that binds to the second antigen, wherein the first antibody or antigen-binding fragment thereof comprises a first heavy chain variable region (VHa) and a first light chain variable region (VLa), and the second antibody or antigen-binding fragment thereof comprises a second heavy chain variable region (VHb) and a second light chain variable region (VLb);
(b) determining the amino acid sequence of VHa, VLa, and VLb;
(c) aligning the amino acid sequences of VLa and VLb and determining the sequence homology between VLa and VLb is less than 80%;
(d) replacing all light chain variable regions in a phage display antibody library with the VLa, and panning against the second antigen to obtain a third heavy chain variable region (VHc);
(e) redesigning the VHa and VHc sequences, thereby obtaining VHa' and VHc' to increase the difference of biochemical or biophysical characteristics between a first protein comprising two polypeptides each comprising VHa' and two polypeptides each comprising VLa, and a second protein comprising two polypeptides each comprising VHc' and two polypeptides each comprising VLa; and
(f) producing a bispecific antibody or antigen-binding fragment thereof that has two light chain variable regions and two heavy chain variable regions, wherein the two light variable regions each comprises VLa, and the two heavy chain variable regions comprise VHa' and VHc' respectively.

In some embodiments, the bispecific antibody or antigen or antigen-binding fragment thereof can also be made by the following methods:

(a) selecting a first antigen and a second antigen, and identifying a first antibody or antigen-binding fragment thereof that binds to the first antigen and a second antibody or antigen-binding fragment thereof that binds to the second antigen, wherein the first antibody or antigen-binding fragment thereof comprises a first heavy chain variable region (VHa) and a first light chain variable region (VLa), and the second antibody or antigen-binding fragment thereof comprises a second heavy chain variable region (VHb) and a second light chain variable region (VLb);
(b) determining the amino acid sequence of VHa, VLa, VHb, and VLb;
(c) aligning the amino acid sequences of VLa and VLb and determining the sequence homology between VLa and VLb is less than 80%;
(d) replacing all light chain variable regions in a phage display antibody library with a plurality of light chain variable regions, wherein the light chain variables regions are at least 80%, 85%, 90%, 95%, or 99% identical to VLa or VLb;
(e) panning against the first and/or the second antigen (e.g., the second antigen);
(f) selecting a common light chain variable region (VLc), and a third heavy chain variable region (VHc), wherein VHa-VLc binds to the first antigen with a desired affinity and VHc-VLc binds to the second antigen with a desired affinity;
(g) redesigning the VHa and VHc sequences, thereby obtaining VHa' and VHc' to increase the difference of biochemical or biophysical characteristics between a first protein comprising two polypeptides each comprising VHa' and two polypeptides each comprising VLc, and a second protein comprising two polypeptides each comprising VHc' and two polypeptides each comprising VLc; and (h) producing a bispecific antibody or antigen-binding fragment thereof that has two light chain variable regions and two heavy chain variable regions, wherein the two light variable regions each comprises VLc, and the two heavy chain variable regions comprise VHa' and VHc' respectively.

In some embodiments, if VHa-VLc cannot bind to the first antigen with a desired affinity, additional steps can be performed. For example, if VLc is at least 80% identical to VLa, a new common light chain can be designed. In some embodiments, the process starts with VLa, and the amino acids can be mutated to the amino acid in VLc based on the methods described herein (e.g., based on the 3D structure of VLa and VLc).

In some embodiments, to design a common light chain variable region involves aligning VLa and VLb, and studying the different residues between VLa and VLb on the same kabat position. If the different residue on VLb does not contact CDRs, interface residues, canonical residues or vernier zone residues on B Fv structure, the residues on VLb are mutated to the residue at the same kabat position on VLa. Otherwise, the residues on VLb are kept.

In some embodiments, to redesign a heavy chain variable region involves using BioLuminate to calculate 3D PI of Fv A and Fv B, and mutating non-CDR, non-canonical, non-interface and non-vernier zone residues to make the Fv which has high 3D PI even higher and the one which has low 3D PI even lower.

How to use BioLuminate can be found, e.g., in BioLuminate's user guide for reference, which is incorporated herein by reference in its entirety.

Antibodies and Antigen Binding Fragments

The present disclosure provides antibodies and antigen-binding fragments thereof that comprise complementary determining regions (CDRs), heavy chain variable regions, light chain variable regions, heavy chains, or light chains described herein. In some embodiments, the antibodies and antigen-binding fragments thereof are imbalanced bispecific antibodies and antigen-binding fragments thereof.

In general, antibodies (also called immunoglobulins) are made up of two classes of polypeptide chains, light chains and heavy chains. A non-limiting antibody of the present disclosure can be an intact, four immunoglobulin chain antibody comprising two heavy chains and two light chains. The heavy chain of the antibody can be of any isotype including IgM, IgG, IgE, IgA, or IgD or sub-isotype including IgG1, IgG2, IgG2a, IgG2b, IgG3, IgG4, IgE1, IgE2, etc. The light chain can be a kappa light chain or a lambda light chain. An antibody can comprise two identical copies of a light chain and/or two identical copies of a heavy chain. The heavy chains, which each contain one variable domain (or variable region, VH) and multiple constant domains (or constant regions), bind to one another via disulfide bonding within their constant domains to form the "stem" of the antibody. The light chains, which each contain one variable domain (or variable region, VL) and one constant domain (or constant region), each bind to one heavy chain via disulfide binding. The variable region of each light chain is aligned with the variable region of the heavy chain to which it is bound. The variable regions of both the light chains and heavy chains contain three hypervariable regions sandwiched between more conserved framework regions (FR).

These hypervariable regions, known as the complementary determining regions (CDRs), form loops that comprise the principle antigen binding surface of the antibody. The four framework regions largely adopt a beta-sheet conformation and the CDRs form loops connecting, and in some cases forming part of, the beta-sheet structure. The CDRs in each chain are held in close proximity by the framework regions and, with the CDRs from the other chain, contribute to the formation of the antigen-binding region.

Methods for identifying the CDR regions of an antibody by analyzing the amino acid sequence of the antibody are well known, and a number of definitions of the CDRs are commonly used. The Kabat definition is based on sequence variability, and the Chothia definition is based on the location of the structural loop regions. These methods and definitions are described in, e.g., Martin, "Protein sequence and structure analysis of antibody variable domains," Antibody engineering, Springer Berlin Heidelberg, 2001. 422-439; Abhinandan, et al. "Analysis and improvements to Kabat and structurally correct numbering of antibody variable domains," Molecular immunology 45.14 (2008): 3832-3839; Wu, T. T. and Kabat, E. A. (1970) J. Exp. Med. 132: 211-250; Martin et al., Methods Enzymol. 203:121-53 (1991); Morea et al., Biophys Chem. 68(1-3):9-16 (October 1997); Morea et al., J Mol Biol. 275(2):269-94 (January 1998); Chothia et al., Nature 342(6252):877-83 (December 1989); Ponomarenko and Bourne, BMC Structural Biology 7:64 (2007); each of which is incorporated herein by reference in its entirety. Unless specifically indicated in the present disclosure, Kabat numbering is used in the present disclosure as a default.

The CDRs are important for recognizing an epitope of an antigen. As used herein, an "epitope" is the smallest portion of a target molecule capable of being specifically bound by the antigen binding domain of an antibody. The minimal size of an epitope may be about three, four, five, six, or seven amino acids, but these amino acids need not be in a consecutive linear sequence of the antigen's primary structure, as the epitope may depend on an antigen's three-dimensional configuration based on the antigen's secondary and tertiary structure.

In some embodiments, the antibody is an intact immunoglobulin molecule (e.g., IgG1, IgG2a, IgG2b, IgG3, IgM, IgD, IgE, IgA). The IgG subclasses (IgG1, IgG2, IgG3, and IgG4) are highly conserved, differ in their constant region, particularly in their hinges and upper CH2 domains. The sequences and differences of the IgG subclasses are known in the art, and are described, e.g., in Vidarsson, et al, "IgG subclasses and allotypes: from structure to effector functions." Frontiers in immunology 5 (2014); Irani, et al. "Molecular properties of human IgG subclasses and their implications for designing therapeutic monoclonal antibodies against infectious diseases." Molecular immunology 67.2 (2015): 171-182; Shakib, Farouk, ed. The human IgG subclasses: molecular analysis of structure, function and regulation. Elsevier, 2016; each of which is incorporated herein by reference in its entirety.

The antibody can also be an immunoglobulin molecule that is derived from any species (e.g., human, rodent, mouse, rat, camelid). Antibodies disclosed herein also include, but are not limited to, polyclonal, monoclonal, monospecific, polyspecific antibodies, and chimeric antibodies that include an immunoglobulin binding domain fused to another polypeptide. The term "antigen binding domain" or "antigen binding fragment" is a portion of an antibody that retains specific binding activity of the intact antibody, i.e., any portion of an antibody that is capable of specific binding to an epitope on the intact antibody's target molecule. It includes, e.g., Fab, Fab', F(ab')2, and variants of these fragments. Thus, in some embodiments, an antibody or an antigen binding fragment thereof can be, e.g., a scFv, a Fv, a Fd, a dAb, a bispecific antibody, a bispecific scFv, a diabody, a linear antibody, a single-chain antibody molecule, a multi-specific antibody formed from antibody fragments, and any polypeptide that includes a binding domain which is, or is homologous to, an antibody binding domain. Non-limiting examples of antigen binding domains include, e.g., the heavy chain and/or light chain CDRs of an intact antibody, the heavy and/or light chain variable regions of an intact antibody, full length heavy or light chains of an intact antibody, or an individual CDR from either the heavy chain or the light chain of an intact antibody.

In some embodiments, the scFV has two heavy chain variable domains, and two light chain variable domains. In some embodiments, the scFV has two antigen binding regions (Antigen binding regions: A and B), and the two antigen binding regions can bind to the respective target antigens with different affinities.

In some embodiments, the antigen binding fragment can form a part of a chimeric antigen receptor (CAR). In some embodiments, the chimeric antigen receptor are fusions of single-chain variable fragments (scFv) as described herein, fused to CD3-zeta transmembrane- and endodomain. In some embodiments, the chimeric antigen receptor also comprises intracellular signaling domains from various costimulatory protein receptors (e.g., CD28, 41BB, ICOS). In some embodiments, the chimeric antigen receptor comprises multiple signaling domains, e.g., CD3z-CD28-41BB or CD3z-CD28-OX40, to increase potency. Thus, in one aspect, the disclosure further provides cells (e.g., T cells) that express the chimeric antigen receptors as described herein.

In some embodiments, the antibodies or antigen-binding fragments thereof can bind to two different antigens or two different epitopes.

In some embodiments, the antibodies or antigen-binding fragments thereof can comprises one, two, or three heavy chain variable region CDRs selected from Table 1, Table 2, Table 11 and Table 12. In some embodiments, the antibodies or antigen-binding fragments thereof can comprises one, two, or three light chain variable region CDRs selected from Table 3, Table 13 and Table 14.

In some embodiments, the antibodies can have a heavy chain variable region (VH) comprising complementarity determining regions (CDRs) 1, 2, 3, wherein the CDR1 region comprises or consists of an amino acid sequence that is at least 80%, 85%, 90%, or 95% identical to a selected VH CDR1 amino acid sequence, the CDR2 region comprises or consists of an amino acid sequence that is at least 80%, 85%, 90%, or 95% identical to a selected VH CDR2 amino acid sequence, and the CDR3 region comprises or consists of an amino acid sequence that is at least 80%, 85%, 90%, or 95% identical to a selected VH CDR3 amino acid sequence, and a light chain variable region (VL) comprising CDRs 1, 2, 3, wherein the CDR1 region comprises or consists of an amino acid sequence that is at least 80%, 85%, 90%, or 95% identical to a selected VL CDR1 amino acid sequence, the CDR2 region comprises or consists of an amino acid sequence that is at least 80%, 85%, 90%, or 95% identical to a selected VL CDR2 amino acid sequence, and the CDR3 region comprises or consists of an amino acid sequence that is at least 80%, 85%, 90%, or 95% identical to a selected VL CDR3 amino acid sequence. The selected VH CDRs 1, 2, 3 amino acid sequences are shown in Table 1, Table 2, Table 11 and Table 12, and the selected VL CDRs, 1, 2, 3 amino acid sequences are shown in Table 3, Table 13 and Table 14.

In some embodiments, the antibody or an antigen-binding fragment described herein can contain a heavy chain variable domain containing one, two, or three of the CDRs selected from Table 1, Table 2, Table 11 and Table 12 with zero, one or two amino acid insertions, deletions, or substitutions.

In some embodiments, the antibody or an antigen-binding fragment described herein can contain a light chain variable domain containing one, two, or three of the CDRs selected from Table 3, Table 13 and Table 14 with zero, one or two amino acid insertions, deletions, or substitutions.

The insertions, deletions, and substitutions can be within the CDR sequence, or at one or both terminal ends of the CDR sequence.

Antibodies and antibody fragments of the present disclosure can be modified in the Fc region to provide desired effector functions or serum half-life.

Multimerization of antibodies may be accomplished through natural aggregation of antibodies or through chemical or recombinant linking techniques known in the art. For example, some percentage of purified antibody preparations (e.g., purified IgG1 molecules) spontaneously form protein aggregates containing antibody homodimers and other higher-order antibody multimers.

Any of the antibodies or antigen-binding fragments described herein may be conjugated to a stabilizing molecule (e.g., a molecule that increases the half-life of the antibody or antigen-binding fragment thereof in a subject or in solution). Non-limiting examples of stabilizing molecules include: a polymer (e.g., a polyethylene glycol) or a protein (e.g., serum albumin, such as human serum albumin). The conjugation of a stabilizing molecule can increase the half-life or extend the biological activity of an antibody or an antigen-binding fragment in vitro (e.g., in tissue culture or when stored as a pharmaceutical composition) or in vivo (e.g., in a human).

In some embodiments, the antibodies or antigen-binding fragments (e.g., bispecific antibodies) described herein can be conjugated to a therapeutic agent. The antibody-drug conjugate comprising the antibody or antigen-binding fragment thereof can covalently or non-covalently bind to a therapeutic agent. In some embodiments, the therapeutic agent is a cytotoxic or cytostatic agent (e.g., cytochalasin B, gramicidin D, ethidium bromide, emetine, mitomycin, etoposide, tenoposide, vincristine, vinblastine, colchicin, doxorubicin, daunorubicin, dihydroxy anthracin, maytansinoids such as DM-1 and DM-4, dione, mitoxantrone, mithramycin, actinomycin D, 1-dehydrotestosterone, glucocorticoids, procaine, tetracaine, lidocaine, propranolol, puromycin, epirubicin, and cyclophosphamide and analogs).

Antibody Characteristics

The antibodies or antigen-binding fragments thereof (e.g., bispecific antibodies) as described herein can increase immune response. In some embodiments, the antibodies or antigen-binding fragments thereof as described herein can increase immune response, activity or number of T cells (e.g., CD3+ cells, CD8+ and/or CD4+ cells) by at least 10%, 20%, 30%, 40%, 50%, 60%, 70%, 80%, 90%, 100%, 2 folds, 3 folds, 5 folds, 10 folds, or 20 folds.

In some embodiments, the antibodies or antigen-binding fragments thereof as described herein can decrease the activity or number of T cells by at least 10%, 20%, 30%, 40%, 50%, 60%, 70%, 80%, 90%, 100%, 2 folds, 3 folds, 5 folds, 10 folds, or 20 folds.

In some embodiments, the antibodies or antigen-binding fragments thereof as described herein does not induce immune response in normal cells (e.g., non-tumor cells) or in the absence of tumor cells.

In some embodiments, the antibodies or antigen-binding fragments thereof (e.g., bispecific antibodies) can bind to PD-L1 or PD-L2. Thus, the antibodies or antigen-binding fragments thereof described herein can block the binding between PD-1 and PD-L1 and/or the binding between PD-1 and PD-L2. In some embodiments, by binding to PD-L1 or PD-L2, the antibody can inhibit PD-1 signaling pathway and upregulates the immune response. Thus, in some embodiments, the antibodies or antigen-binding fragments thereof as described herein are PD-1 antagonist. In some embodiments, the antibodies or antigen-binding fragments thereof are PD-1 agonist.

In some embodiments, the antibodies or antigen-binding fragments thereof (e.g., bispecific antibodies) can bind to CD3. Thus, the antibodies or antigen-binding fragments thereof described herein can recruit T cells to a target cell.

In some embodiments, the antibody (or antigen-binding fragments thereof) specifically binds to an antigen (e.g., a human protein, a monkey protein, and/or a mouse protein) with a dissociation rate (koff) of less than 0.1 s$^{-1}$, less than 0.01 s$^{-1}$, less than 0.001 s$^{-1}$, less than 0.0001 s$^{-1}$, or less than 0.00001 s$^{-1}$. In some embodiments, the dissociation rate (koff) is greater than 0.01 s$^{-1}$, greater than 0.001 s$^{-1}$, greater than 0.0001 s$^{-1}$, greater than 0.00001 s$^{-1}$, or greater than 0.000001 s$^{-1}$. In some embodiments, kinetic association rates (kon) is greater than $1\times10^2$/Ms, greater than $1\times10^3$/Ms, greater than $1\times10^4$/Ms, greater than $1\times10^5$/Ms, or greater than $1\times10^6$/Ms. In some embodiments, kinetic association rates (kon) is less than $1\times10^5$/Ms, less than $1\times10^6$/Ms, or less than $1\times10^7$/Ms.

Affinities can be deduced from the quotient of the kinetic rate constants (Kd=koff/kon). In some embodiments, Kd is less than $1\times10^{-4}$ M, less than $1\times10^{-5}$ M, less than $1\times10^{-6}$ M, less than $1\times10^{-7}$ M, less than $1\times10^{-8}$ M, less than $1\times10^{-9}$ M, or less than $1\times10^{-10}$ M. In some embodiments, the Kd is less than 50 nM, 30 nM, 20 nM, 15 nM, 10 nM, 9 nM, 8 nM, 7 nM, 6 nM, 5 nM, 4 nM, 3 nM, 2 nM, or 1 nM. In some embodiments, Kd is greater than $1\times10^{-4}$ M, greater than $1\times10^{-5}$ M, greater than $1\times10^{-6}$ M, greater than $1\times10^{-7}$ M, greater than $1\times10^{-8}$ M, greater than $1\times10^{-9}$ M, greater than $1\times10^{-10}$ M, greater than $1\times10^{-11}$ M, or greater than $1\times10^{-12}$ M. Furthermore, Ka can be deduced from Kd by the formula Ka=1/Kd.

General techniques for measuring the affinity of an antibody for an antigen include, e.g., ELISA, RIA, and surface plasmon resonance (SPR).

In some embodiments, thermal stabilities are determined. The antibodies or antigen binding fragments as described herein can have a Tm greater than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C.

As IgG can be described as a multi-domain protein, the melting curve sometimes shows two transitions, or three transitions, with a first denaturation temperature, Tm D1, and a second denaturation temperature Tm D2, and optionally a third denaturation temperature Tm D3.

In some embodiments, the antibodies or antigen binding fragments as described herein has a Tm D1 greater than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C. In some embodiments, the antibodies or antigen binding fragments as described herein has a Tm D2 greater than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C. In some embodiments, the antibodies or antigen binding fragments as described herein has a Tm D3 greater than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C.

In some embodiments, Tm, Tm D1, Tm D2, Tm D3 are less than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C.

In some embodiments, the antibodies or antigen binding fragments as described herein do not start to form aggregation when the temperate is less than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C. In some embodiments, Tagg266 or Tagg473 is less than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C.

In some embodiments, the antibodies or antigen binding fragments as described herein have a pI greater than 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, or 9.9. In some embodiments, the antibodies or antigen binding fragments as described herein have a pI less than 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, or 9.9.

In some embodiments, the antibody has a tumor growth inhibition percentage (TGI %) that is greater than 10%, 20%, 30%, 40%, 50%, 60%, 70%, 80%, 90%, 100%, 110%, 120%, 130%, 140%, 150%, 160%, 170%, 180%, 190%, or 200%. In some embodiments, the antibody has a tumor growth inhibition percentage that is less than 60%, 70%, 80%, 90%, 100%, 110%, 120%, 130%, 140%, 150%, 160%, 170%, 180%, 190%, or 200%. The TGI % can be determined, e.g., at 3, 4, 5, 6, 7, 8, 9, 10, 11, 12, 13, 14, 15, 16, 17, 18, 19, 20, 21, 22, 23, 24, 25, 26, 27, 28, 29, or 30 days after the treatment starts, or 1, 2, 3, 4, 5, 6, 7, 8, 9, 10, 11, or 12 months after the treatment starts. As used herein, the tumor growth inhibition percentage (TGI %) is calculated using the following formula:

$$\text{TGI } (\%) = [1-(Ti-T0)/(Vi-V0)] \times 100$$

Ti is the average tumor volume in the treatment group on day i. T0 is the average tumor volume in the treatment group on day zero. Vi is the average tumor volume in the control group on day i. V0 is the average tumor volume in the control group on day zero.

In some embodiments, the antibodies or antigen binding fragments can increase complement dependent cytotoxicity (CDC) by at least 10%, 20%, 30%, 40%, 50%, 60%, 70%, 80%, 90%, 100%, 2 folds, 3 folds, 5 folds, 10 folds, or 20 folds.

In some embodiments, the antibodies or antigen binding fragments can increase antibody-dependent cell-mediated cytotoxicity (ADCC) by at least 10%, 20%, 30%, 40%, 50%, 60%, 70%, 80%, 90%, 100%, 2 folds, 3 folds, 5 folds, 10 folds, or 20 folds.

In some embodiments, the antibodies or antigen binding fragments can increase internalization rate by at least 10%, 20%, 30%, 40%, 50%, 60%, 70%, 80%, 90%, 100%, 2 folds, 3 folds, 5 folds, 10 folds, or 20 folds.

In some embodiments, the antibodies or antigen binding fragments can increase phagocytosis rate by at least 10%, 20%, 30%, 40%, 50%, 60%, 70%, 80%, 90%, 100%, 2 folds, 3 folds, 5 folds, 10 folds, or 20 folds.

In some embodiments, the antibodies or antigen binding fragments can enhance T cell function, for example, by increasing effector T cell proliferation and/or increasing gamma interferon production by the effector T cell (e.g., as compared to proliferation and/or cytokine production prior to treatment with the antibodies or antigen binding fragments).

In some embodiments, the antibodies or antigen binding fragments enhance CD4+ effector T cell function, for example, by increasing CD4+ effector T cell proliferation and/or increasing gamma interferon production by the CD4+ effector T cell (e.g., as compared to proliferation and/or cytokine production prior to treatment with the antibodies or antigen binding fragments). In some embodiments, the cytokine is gamma interferon. In some embodiments, the antibodies or antigen binding fragments increase number of intratumoral (infiltrating) CD4+ effector T cells (e.g., total number of CD4+ effector T cells, or e.g., percentage of CD4+ cells in CD45+ cells), e.g., as compared to number of intratumoral (infiltrating) CD4+ T cells prior to treatment with antibodies or antigen binding fragments. In some embodiments, the antibodies or antigen binding fragments increase number of intratumoral (infiltrating) CD4+ effector T cells that express gamma interferon (e.g., total gamma interferon expressing CD4+ cells, or e.g., percentage of gamma interferon expressing CD4+ cells in total CD4+ cells), e.g., as compared to number of intratumoral (infiltrating) CD4+ T cells that express gamma interferon prior to treatment.

In some embodiments, the antibodies or antigen binding fragments increase number of intratumoral (infiltrating) CD8+ effector T cells (e.g., total number of CD8+ effector T cells, or e.g., percentage of CD8+ in CD45+ cells), e.g., as compared to number of intratumoral (infiltrating) CD8+ T effector cells prior to treatment. In some embodiments, the antibodies or antigen binding fragments increase number of intratumoral (infiltrating) CD8+ effector T cells that express gamma interferon (e.g., percentage of CD8+ cells that express gamma interferon in total CD8+ cells), e.g., compared to number of intratumoral (infiltrating) CD8+ T cells that express gamma interferon prior to treatment with the antibody.

In some embodiments, the antibodies or antigen binding fragments enhance memory T cell function, for example by increasing memory T cell proliferation and/or increasing cytokine (e.g., gamma interferon) production by the memory cell.

In some embodiments, the antibodies or antigen binding fragments have a functional Fc region. In some embodiments, effector function of a functional Fc region is antibody-dependent cell-mediated cytotoxicity (ADCC). In some embodiments, effector function of a functional Fc region is phagocytosis. In some embodiments, effector function of a functional Fc region is ADCC and phagocytosis. In some embodiments, the Fc region is human IgG1, human IgG2, human IgG3, or human IgG4.

In some embodiments, the antibodies or antigen binding fragments can induce apoptosis.

In some embodiments, the antibodies or antigen binding fragments do not have a functional Fc region. For example, the antibodies or antigen binding fragments are Fab, Fab', F(ab')2, and Fv fragments.

In some embodiments, the antibodies or antigen binding fragments are humanized antibodies. The humanization percentage means the percentage identity of the heavy chain or light chain variable region sequence as compared to human antibody sequences in International Immunogenetics Information System (IMGT) database. In some embodiments, humanization percentage is greater than 80%, 81%, 82%, 83%, 84%, 85%, 86%, 87%, 88%, 89%, 90%, 91%, 92%, 93%, 94%, or 95%. A detailed description regarding how to determine humanization percentage is known in the art, and is described, e.g., in Jones, Tim D., et al. "The INNs and outs of antibody nonproprietary names." MAbs. Vol. 8. No. 1. Taylor & Francis, 2016, which is incorporated herein by reference in its entirety. A high humanization percentage often has various advantages, e.g., more safe and more effective in humans, more likely to be tolerated by a human subject, and/or less likely to have side effects. In some embodiments, the antibodies or antigen binding fragments are human antibodies.

Recombinant Vectors

The present disclosure also provides recombinant vectors (e.g., an expression vectors) that include an isolated polynucleotide disclosed herein (e.g., a polynucleotide that encodes a polypeptide disclosed herein), host cells into which are introduced the recombinant vectors (i.e., such that the host cells contain the polynucleotide and/or a vector comprising the polynucleotide), and the production of recombinant antibody polypeptides or fragments thereof by recombinant techniques.

As used herein, a "vector" is any construct capable of delivering one or more polynucleotide(s) of interest to a host cell when the vector is introduced to the host cell. An "expression vector" is capable of delivering and expressing the one or more polynucleotide(s) of interest as an encoded polypeptide in a host cell into which the expression vector has been introduced. Thus, in an expression vector, the polynucleotide of interest is positioned for expression in the vector by being operably linked with regulatory elements such as a promoter, enhancer, and/or a poly-A tail, either within the vector or in the genome of the host cell at or near or flanking the integration site of the polynucleotide of interest such that the polynucleotide of interest will be translated in the host cell introduced with the expression vector.

A vector can be introduced into the host cell by methods known in the art, e.g., electroporation, chemical transfection (e.g., DEAE-dextran), transformation, transfection, and infection and/or transduction (e.g., with recombinant virus). Thus, non-limiting examples of vectors include viral vectors (which can be used to generate recombinant virus), naked DNA or RNA, plasmids, cosmids, phage vectors, and DNA or RNA expression vectors associated with cationic condensing agents.

In some implementations, a polynucleotide disclosed herein (e.g., a polynucleotide that encodes a polypeptide disclosed herein) is introduced using a viral expression system (e.g., vaccinia or other pox virus, retrovirus, or adenovirus), which may involve the use of a non-pathogenic (defective), replication competent virus, or may use a replication defective virus. In the latter case, viral propagation generally will occur only in complementing virus packaging cells. Suitable systems are disclosed, for example, in Fisher-Hoch et al., 1989, Proc. Natl. Acad. Sci. USA 86:317-321; Flexner et al., 1989, Ann. N.Y. Acad Sci. 569:86-103; Flexner et al., 1990, Vaccine, 8:17-21; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner-Biotechniques, 6:616-627, 1988; Rosenfeld et al., 1991, Science, 252:431-434; Kolls et al., 1994, Proc. Natl. Acad. Sci. USA, 91:215-219; Kass-Eisler et al., 1993, Proc. Natl. Acad. Sci. USA, 90:11498-11502; Guzman et al., 1993, Circulation, 88:2838-2848; and Guzman et al., 1993, Cir. Res., 73:1202-1207. Techniques for incorporating DNA into such expression systems are well known to those of ordinary skill in the art. The DNA may also be "naked," as described, for example, in Ulmer et al., 1993, Science, 259:1745-1749, and Cohen, 1993, Science, 259:1691-1692. The uptake of naked DNA may be increased by coating the DNA onto biodegradable beads that are efficiently transported into the cells.

For expression, the DNA insert comprising an antibody-encoding or polypeptide-encoding polynucleotide disclosed herein can be operatively linked to an appropriate promoter (e.g., a heterologous promoter), such as the phage lambda PL promoter, the *E. coli* lac, trp and tac promoters, the SV40 early and late promoters and promoters of retroviral LTRs, to name a few. Other suitable promoters are known to the skilled artisan. The expression constructs can further contain sites for transcription initiation, termination and, in the transcribed region, a ribosome binding site for translation. The coding portion of the mature transcripts expressed by the constructs may include a translation initiating at the beginning and a termination codon (UAA, UGA, or UAG) appropriately positioned at the end of the polypeptide to be translated.

As indicated, the expression vectors can include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli, Streptomyces*, and *Salmonella typhimurium* cells; fungal cells, such as yeast cells; insect cells such as *Drosophila* S2 and *Spodoptera* Sf9 cells; animal cells such as CHO, COS, Bowes melanoma, and HK 293 cells; and plant cells. Appropriate culture mediums and conditions for the host cells described herein are known in the art.

Non-limiting vectors for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Non-limiting eukaryotic vectors include pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Non-limiting bacterial promoters suitable for use include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

In the yeast *Saccharomyces cerevisiae*, a number of vectors containing constitutive or inducible promoters such as alpha factor, alcohol oxidase, and PGH may be used. For reviews, see Ausubel et al. (1989) Current Protocols in Molecular Biology, John Wiley & Sons, New York, NY, and Grant et al., *Methods Enzymol.*, 153: 516-544 (1997).

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods In Molecular Biology (1986), which is incorporated herein by reference in its entirety.

Transcription of DNA encoding an antibody of the present disclosure by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at base pairs 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide (e.g., antibody) can be expressed in a modified form, such as a fusion protein (e.g., a GST-fusion) or with a histidine-tag, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties can be added to the polypeptide to facilitate purification. Such regions can be removed prior to final preparation of the polypeptide. The addition of peptide moieties to polypeptides to engender secretion or excretion, to improve stability and to facilitate purification, among others, are familiar and routine techniques in the art.

The disclosure also provides a nucleic acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any nucleotide sequence as described herein, and an amino acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any amino acid sequence as described herein.

The disclosure also provides a nucleic acid sequence that has a homology of at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% to any nucleotide sequence as described herein, and an amino acid sequence that has a homology of at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% to any amino acid sequence as described herein.

In some embodiments, the disclosure relates to nucleotide sequences encoding any peptides that are described herein, or any amino acid sequences that are encoded by any nucleotide sequences as described herein. In some embodiments, the nucleic acid sequence is less than 10, 20, 30, 40, 50, 60, 70, 80, 90, 100, 110, 120, 130, 150, 200, 250, 300, 350, 400, 500, or 600 nucleotides. In some embodiments, the amino acid sequence is less than 5, 6, 7, 8, 9, 10, 20, 30, 40, 50, 60, 70, 80, 90, 100, 110, 120, 130, 140, 150, 160, 170, 180, 190, 200, 250, 300, 350, or 400 amino acid residues.

In some embodiments, the amino acid sequence (i) comprises an amino acid sequence; or (ii) consists of an amino acid sequence, wherein the amino acid sequence is any one of the sequences as described herein.

In some embodiments, the nucleic acid sequence (i) comprises a nucleic acid sequence; or (ii) consists of a nucleic acid sequence, wherein the nucleic acid sequence is any one of the sequences as described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences. For purposes of the present invention, the comparison of sequences and determination of percent identity between two sequences can be accomplished using a Blossum 62 scoring matrix with a gap penalty of 12, a gap extend penalty of 4, and a frameshift gap penalty of 5.

The percentage of sequence homology (e.g., amino acid sequence homology or nucleic acid homology) can also be determined. How to determine percentage of sequence homology is known in the art. In some embodiments, amino acid residues conserved with similar physicochemical properties (percent homology), e.g. leucine and isoleucine, can be used to measure sequence similarity. Families of amino acid residues having similar physicochemical properties have been defined in the art. These families include e.g., amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The homology percentage, in many cases, is higher than the identity percentage.

Methods of Making Antibodies

An isolated fragment of human protein (e.g., CD55, CD3, cancer specific antigen or cancer-associated antigen) can be used as an immunogen to generate antibodies using standard techniques for polyclonal and monoclonal antibody preparation. Polyclonal antibodies can be raised in animals by multiple injections (e.g., subcutaneous or intraperitoneal injections) of an antigenic peptide or protein. In some embodiments, the antigenic peptide or protein is injected with at least one adjuvant. In some embodiments, the antigenic peptide or protein can be conjugated to an agent that is immunogenic in the species to be immunized. Animals can be injected with the antigenic peptide or protein more than one time (e.g., twice, three times, or four times).

The full-length polypeptide or protein can be used or, alternatively, antigenic peptide fragments thereof can be used as immunogens. The antigenic peptide of a protein comprises at least 8 (e.g., at least 10, 15, 20, or 30) amino acid residues of the amino acid sequence of the protein and encompasses an epitope of the protein such that an antibody raised against the peptide forms a specific immune complex with the protein.

An immunogen typically is used to prepare antibodies by immunizing a suitable subject (e.g., human or transgenic animal expressing at least one human immunoglobulin locus). An appropriate immunogenic preparation can contain, for example, a recombinantly-expressed or a chemically-synthesized polypeptide. The preparation can further include an adjuvant, such as Freund's complete or incomplete adjuvant, or a similar immunostimulatory agent.

Polyclonal antibodies can be prepared as described above by immunizing a suitable subject with a polypeptide, or an antigenic peptide thereof (e.g., part of the protein) as an immunogen. The antibody titer in the immunized subject can be monitored over time by standard techniques, such as with an enzyme-linked immunosorbent assay (ELISA) using the immobilized polypeptide or peptide. If desired, the antibody molecules can be isolated from the mammal (e.g., from the blood) and further purified by well-known techniques, such as protein A of protein G chromatography to obtain the IgG fraction. At an appropriate time after immunization, e.g., when the specific antibody titers are highest, antibody-producing cells can be obtained from the subject and used to prepare monoclonal antibodies by standard techniques, such as the hybridoma technique originally described by Kohler et al. (Nature 256:495-497, 1975), the human B cell hybridoma technique (Kozbor et al., Immunol. Today 4:72, 1983), the EBV-hybridoma technique (Cole et al., Monoclonal Antibodies and Cancer Therapy, Alan R. Liss, Inc., pp. 77-96, 1985), or trioma techniques. The technology for producing hybridomas is well known (see, generally, Current Protocols in Immunology, 1994, Coligan et al. (Eds.), John Wiley & Sons, Inc., New York, NY). Hybridoma cells producing a monoclonal antibody are detected by screening the hybridoma culture supernatants for antibodies that bind the polypeptide or epitope of interest, e.g., using a standard ELISA assay.

Variants of the antibodies or antigen-binding fragments described herein can be prepared by introducing appropriate nucleotide changes into the DNA encoding a human, humanized, or chimeric antibody, or antigen-binding fragment thereof described herein, or by peptide synthesis. Such variants include, for example, deletions, insertions, or substitutions of residues within the amino acids sequences that make-up the antigen-binding site of the antibody or an antigen-binding domain. In a population of such variants, some antibodies or antigen-binding fragments will have increased affinity for the target protein. Any combination of deletions, insertions, and/or combinations can be made to arrive at an antibody or antigen-binding fragment thereof that has increased binding affinity for the target. The amino acid changes introduced into the antibody or antigen-binding fragment can also alter or introduce new post-translational modifications into the antibody or antigen-binding fragment, such as changing (e.g., increasing or decreasing) the number of glycosylation sites, changing the type of glycosylation site (e.g., changing the amino acid sequence such that a different sugar is attached by enzymes present in a cell), or introducing new glycosylation sites.

Antibodies disclosed herein can be derived from any species of animal, including mammals. Non-limiting examples of native antibodies include antibodies derived from humans, primates, e.g., monkeys and apes, cows, pigs, horses, sheep, camelids (e.g., camels and llamas), chicken, goats, and rodents (e.g., rats, mice, hamsters and rabbits), including transgenic rodents genetically engineered to produce human antibodies.

Phage display (panning) can be used to optimize antibody sequences with desired binding affinities. In this technique, a gene encoding single chain Fv (comprising VH or VL) can be inserted into a phage coat protein gene, causing the phage to "display" the scFv on its outside while containing the gene for the protein on its inside, resulting in a connection between genotype and phenotype. These displaying phages can then be screened against target antigens, in order to detect interaction between the displayed antigen binding sites and the target antigen. Thus, large libraries of proteins can be screened and amplified in a process called in vitro selection, and antibodies sequences with desired binding affinities can be obtained.

Human and humanized antibodies include antibodies having variable and constant regions derived from (or having the same amino acid sequence as those derived from) human germline immunoglobulin sequences. Human antibodies may include amino acid residues not encoded by human germline immunoglobulin sequences (e.g., mutations introduced by random or site-specific mutagenesis in vitro or by somatic mutation in vivo), for example in the CDRs.

A humanized antibody, typically has a human framework (FR) grafted with non-human CDRs. Thus, a humanized antibody has one or more amino acid sequence introduced into it from a source which is non-human. These non-human amino acid residues are often referred to as "import" residues, which are typically taken from an "import" variable domain. Humanization can be essentially performed by e.g., substituting rodent CDRs or CDR sequences for the corresponding sequences of a human antibody. These methods are described in e.g., Jones et al., Nature, 321:522-525 (1986); Riechmann et al., Nature, 332:323-327 (1988); Verhoeyen et al., Science, 239:1534-1536 (1988); each of which is incorporated by reference herein in its entirety. Accordingly, "humanized" antibodies are chimeric antibodies wherein substantially less than an intact human V domain has been substituted by the corresponding sequence from a non-human species. In practice, humanized antibodies are typically mouse antibodies in which some CDR residues and some FR residues are substituted by residues from analogous sites in human antibodies.

It is further important that antibodies be humanized with retention of high specificity and affinity for the antigen and other favorable biological properties. To achieve this goal, humanized antibodies can be prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved.

Identity or homology with respect to an original sequence is usually the percentage of amino acid residues present within the candidate sequence that are identical with a sequence present within the human, humanized, or chimeric antibody or fragment, after aligning the sequences and introducing gaps, if necessary, to achieve the maximum percent sequence identity, and not considering any conservative substitutions as part of the sequence identity.

In some embodiments, a covalent modification can be made to the antibody or antigen-binding fragment thereof. These covalent modifications can be made by chemical or enzymatic synthesis, or by enzymatic or chemical cleavage. Other types of covalent modifications of the antibody or antibody fragment are introduced into the molecule by reacting targeted amino acid residues of the antibody or fragment with an organic derivatization agent that is capable of reacting with selected side chains or the N- or C-terminal residues.

In some embodiments, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues; or position 314 in Kabat numbering); however, Asn297 may also be located about ±3 amino acids upstream or downstream of position 297, i.e., between positions 294 and 300, due to minor sequence variations in antibodies. Such fucosylation variants may have improved ADCC function. In some embodiments, to reduce glycan heterogeneity, the Fc region of the antibody can be further engineered to replace the Asparagine at position 297 with Alanine (N297A).

In some embodiments, to facilitate production efficiency by avoiding Fab-arm exchange, the Fc region of the antibodies was further engineered to replace the serine at position 228 (EU numbering) of IgG4 with proline (S228P). A detailed description regarding S228 mutation is described, e.g., in Silva et al. "The S228P mutation prevents in vivo and in vitro IgG4 Fab-arm exchange as demonstrated using a combination of novel quantitative immunoassays and physiological matrix preparation." Journal of Biological Chemistry 290.9 (2015): 5462-5469, which is incorporated by reference in its entirety.

In some embodiments, the methods described here are designed to make a bispecific antibody. Bispecific antibodies can be made by engineering the interface between a pair of antibody molecules to maximize the percentage of heterodimers that are recovered from recombinant cell culture. For example, the interface can contain at least a part of the CH3 domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. This method is described, e.g., in WO 96/27011, which is incorporated by reference in its entirety.

In some embodiments, one or more amino acid residues in the CH3 portion of the IgG are substituted. In some embodiments, one heavy chain has one or more of the following substitutions Y349C and T366W. The other heavy chain can have one or more the following substitutions E356C, T366S, L368A, and Y407V. Furthermore, a substitution (-ppcpScp→-ppcpPcp-) can also be introduced at the hinge regions of both substituted IgG. In some embodiments, one heavy chain has a T366Y (knob) substitution, and the other heavy chain has a Y407T (hole) substation.

Furthermore, an anion-exchange chromatography can be used to purify bispecific antibodies. Anion-exchange chromatography is a process that separates substances based on their charges using an ion-exchange resin containing positively charged groups, such as diethyl-aminoethyl groups (DEAE). In solution, the resin is coated with positively charged counter-ions (cations). Anion exchange resins will bind to negatively charged molecules, displacing the counter-ion. Anion exchange chromatography can be used to purify proteins based on their isoelectric point (pI). The isoelectric point is defined as the pH at which a protein has no net charge. When the pH>pI, a protein has a net negative charge and when the pH<pI, a protein has a net positive charge. Thus, in some embodiments, different amino acid substitution can be introduced into two heavy chains, so that the pI for the homodimer comprising two Arm A and the pI for the homodimer comprising two Arm B is different. The pI for the bispecific antibody having Arm A and Arm B will be somewhere between the two pIs of the homodimers. Thus, the two homodimers and the bispecific antibody can be released at different pH conditions. The present disclosure shows that a few amino acid residue substitutions can be introduced to the heavy chains to adjust pI.

Thus, in some embodiments, the amino acid residue at Kabat numbering position 83 is lysine, arginine, or histidine. In some embodiments, the amino acid residues at one or more of the positions 1, 6, 43, 81, and 105 (Kabat numbering) is aspartic acid or glutamic acid.

In some embodiments, the amino acid residues at one or more of the positions 13 and 105 (Kabat numbering) is aspartic acid or glutamic acid. In some embodiments, the amino acid residues at one or more of the positions 13 and 42 (Kabat numbering) is lysine, arginine, histidine, or glycine.

Bispecific antibodies can also include e.g., cross-linked or "heteroconjugate" antibodies. For example, one of the antibodies in the heteroconjugate can be coupled to avidin and the other to biotin. Heteroconjugate antibodies can also be made using any convenient cross-linking methods. Suitable cross-linking agents and cross-linking techniques are well known in the art and are disclosed in U.S. Pat. No. 4,676,980, which is incorporated herein by reference in its entirety.

Methods for generating bispecific antibodies from antibody fragments are also known in the art. For example, bispecific antibodies can be prepared using chemical linkage. Brennan et al. (Science 229:81, 1985) describes a procedure where intact antibodies are proteolytically cleaved to generate F(ab')2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab' TNB derivatives is then reconverted to the Fab' thiol by reduction with mercaptoethylamine, and is mixed with an equimolar amount of another Fab' TNB derivative to form the bispecific antibody.

Methods of Treatment

The methods described herein include methods for the treatment of disorders associated with cancer. Generally, the methods include administering a therapeutically effective amount of engineered bispecific antibodies (e.g., imbalanced bispecific antibodies) of antigen-binding fragments thereof as described herein, to a subject who is in need of, or who has been determined to be in need of, such treatment.

As used in this context, to "treat" means to ameliorate at least one symptom of the disorder associated with cancer. Often, cancer results in death; thus, a treatment can result in an increased life expectancy (e.g., by at least 1, 2, 3, 4, 5, 6, 7, 8, 9, 10, 11, 12 months, or by at least 1, 2, 3, 4, 5, 6, 7, 8, 9, 10 years). Administration of a therapeutically effective amount of an agent described herein (e.g., imbalanced bispecific antibodies) for the treatment of a condition associated with cancer will result in decreased number of cancer cells and/or alleviated symptoms.

As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancerous cells. Cancers that can be treated or diagnosed using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. In some embodiments, the agents described herein are designed for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In some embodiments, the cancer is Rituximab (Rituxan®) resistant cancer.

In one aspect, the disclosure also provides methods for treating a cancer in a subject, methods of reducing the rate of the increase of volume of a tumor in a subject over time, methods of reducing the risk of developing a metastasis, or methods of reducing the risk of developing an additional metastasis in a subject. In some embodiments, the treatment can halt, slow, retard, or inhibit progression of a cancer. In some embodiments, the treatment can result in the reduction of in the number, severity, and/or duration of one or more symptoms of the cancer in a subject.

In one aspect, the disclosure features methods that include administering a therapeutically effective amount of an antibody or antigen-binding fragment thereof, or an antibody drug conjugate disclosed herein to a subject in need thereof, e.g., a subject having, or identified or diagnosed as having, a cancer, e.g., breast cancer (e.g., triple-negative breast cancer), carcinoid cancer, cervical cancer, endometrial cancer, glioma, head and neck cancer, liver cancer, lung cancer, small cell lung cancer, lymphoma, melanoma, ovarian cancer, pancreatic cancer, prostate cancer, renal cancer, colorectal cancer, gastric cancer, testicular cancer, thyroid cancer, bladder cancer, urethral cancer, or hematologic malignancy.

As used herein, the terms "subject" and "patient" are used interchangeably throughout the specification and describe an animal, human or non-human, to whom treatment according to the methods of the present invention is provided. Veterinary and non-veterinary applications are contemplated by the present invention. Human patients can be adult humans or juvenile humans (e.g., humans below the age of 18 years old). In addition to humans, patients include but are not limited to mice, rats, hamsters, guinea-pigs, rabbits, ferrets, cats, dogs, and primates. Included are, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

In some embodiments, the cancer is unresectable melanoma or metastatic melanoma, non-small cell lung carcinoma (NSCLC), small cell lung cancer (SCLC), bladder cancer, or metastatic hormone-refractory prostate cancer. In some embodiments, the subject has a solid tumor. In some embodiments, the cancer is squamous cell carcinoma of the head and neck (SCCHN), renal cell carcinoma (RCC), triple-negative breast cancer (TNBC), or colorectal carcinoma. In some embodiments, the subject has Hodgkin's lymphoma. In some embodiments, the subject has triple-negative breast cancer (TNBC), gastric cancer, urothelial cancer, Merkel-cell carcinoma, or head and neck cancer. In some embodiments, the cancer is melanoma, pancreatic carcinoma, mesothelioma, hematological malignancies, especially Non-Hodgkin's lymphoma, lymphoma, chronic lymphocytic leukemia, or advanced solid tumors.

In some embodiments, the compositions and methods disclosed herein can be used for treatment of patients at risk for a cancer. Patients with cancer can be identified with various methods known in the art.

As used herein, by an "effective amount" is meant an amount or dosage sufficient to effect beneficial or desired results including halting, slowing, retarding, or inhibiting progression of a disease, e.g., a cancer. An effective amount will vary depending upon, e.g., an age and a body weight of a subject to which the antibody, antigen binding fragment, antibody-drug conjugates, antibody-encoding polynucleotide, vector comprising the polynucleotide, and/or compositions thereof is to be administered, a severity of symptoms and a route of administration, and thus administration can be determined on an individual basis.

An effective amount can be administered in one or more administrations. By way of example, an effective amount of an antibody, an antigen binding fragment, or an antibody-drug conjugate is an amount sufficient to ameliorate, stop, stabilize, reverse, inhibit, slow and/or delay progression of an autoimmune disease or a cancer in a patient or is an amount sufficient to ameliorate, stop, stabilize, reverse, slow and/or delay proliferation of a cell (e.g., a biopsied cell, any of the cancer cells described herein, or cell line (e.g., a cancer cell line)) in vitro. As is understood in the art, an effective amount of an antibody, antigen binding fragment, or antibody-drug conjugate may vary, depending on, inter alia, patient history as well as other factors such as the type (and/or dosage) of antibody used.

Effective amounts and schedules for administering the antibodies, antibody-encoding polynucleotides, antibody-drug conjugates, and/or compositions disclosed herein may be determined empirically, and making such determinations is within the skill in the art. Those skilled in the art will understand that the dosage that must be administered will vary depending on, for example, the mammal that will receive the antibodies, antibody-encoding polynucleotides, antibody-drug conjugates, and/or compositions disclosed herein, the route of administration, the particular type of antibodies, antibody-encoding polynucleotides, antigen binding fragments, antibody-drug conjugates, and/or compositions disclosed herein used and other drugs being administered to the mammal. Guidance in selecting appropriate doses for antibody or antigen binding fragment can be found in the literature on therapeutic uses of antibodies and antigen binding fragments, e.g., Handbook of Monoclonal Antibodies, Ferrone et al., eds., Noges Publications, Park Ridge, N.J., 1985, ch. 22 and pp. 303-357; Smith et al., Antibodies in Human Diagnosis and Therapy, Haber et al., eds., Raven Press, New York, 1977, pp. 365-389.

A typical daily dosage of an effective amount of an antibody is 0.01 mg/kg to 100 mg/kg. In some embodiments, the dosage can be less than 100 mg/kg, 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.5 mg/kg, or 0.1 mg/kg. In some embodiments, the dosage can be greater than 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.5 mg/kg, 0.1 mg/kg, 0.05 mg/kg, or 0.01 mg/kg. In some embodiments, the dosage is about 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.9 mg/kg, 0.8 mg/kg, 0.7 mg/kg, 0.6 mg/kg, 0.5 mg/kg, 0.4 mg/kg, 0.3 mg/kg, 0.2 mg/kg, or 0.1 mg/kg.

In any of the methods described herein, the at least one antibody, antigen-binding fragment thereof, antibody-drug conjugates, or pharmaceutical composition (e.g., any of the antibodies, antigen-binding fragments, antibody-drug conjugates, or pharmaceutical compositions described herein) and, optionally, at least one additional therapeutic agent can be administered to the subject at least once a week (e.g., once a week, twice a week, three times a week, four times a week, once a day, twice a day, or three times a day). In some embodiments, at least two different antibodies and/or antigen-binding fragments are administered in the same composition (e.g., a liquid composition). In some embodiments, at least one antibody, antigen-binding fragment, antibody-drug conjugates, and at least one additional therapeutic agent are administered in the same composition (e.g., a liquid composition). In some embodiments, the at least one antibody or antigen-binding fragment and the at least one additional therapeutic agent are administered in two different compositions (e.g., a liquid composition containing at least one antibody or antigen-binding fragment and a solid oral composition containing at least one additional therapeutic agent). In some embodiments, the at least one additional therapeutic agent is administered as a pill, tablet, or capsule. In some embodiments, the at least one additional therapeutic agent is administered in a sustained-release oral formulation.

In some embodiments, the one or more additional therapeutic agents can be administered to the subject prior to, or after administering the at least one antibody, antigen-binding antibody fragment, antibody-drug conjugate, or pharmaceutical composition (e.g., any of the antibodies, antigen-binding antibody fragments, or pharmaceutical compositions described herein). In some embodiments, the one or more additional therapeutic agents and the at least one antibody, antigen-binding antibody fragment, antibody-drug conjugate, or pharmaceutical composition (e.g., any of the antibodies, antigen-binding antibody fragments, or pharmaceutical compositions described herein) are administered to the subject such that there is an overlap in the bioactive period of the one or more additional therapeutic agents and the at least one antibody or antigen-binding fragment (e.g., any of the antibodies or antigen-binding fragments described herein) in the subject.

In some embodiments, the subject can be administered the at least one antibody, antigen-binding antibody fragment, antibody-drug conjugate, or pharmaceutical composition (e.g., any of the antibodies, antigen-binding antibody fragments, or pharmaceutical compositions described herein) over an extended period of time (e.g., over a period of at least 1 week, 2 weeks, 3 weeks, 1 month, 2 months, 3 months, 4 months, 5 months, 6 months, 7 months, 8 months, 9 months, 10 months, 11 months, 12 months, 1 year, 2 years, 3 years, 4 years, or 5 years). A skilled medical professional may determine the length of the treatment period using any of the methods described herein for diagnosing or following the effectiveness of treatment (e.g., the observation of at least one symptom of cancer). As described herein, a skilled medical professional can also change the identity and number (e.g., increase or decrease) of antibodies or antigen-binding antibody fragments, antibody-drug conjugates (and/or one or more additional therapeutic agents) administered to the subject and can also adjust (e.g., increase or decrease) the dosage or frequency of administration of at least one antibody or antigen-binding antibody fragment (and/or one or more additional therapeutic agents) to the subject based on an assessment of the effectiveness of the treatment (e.g., using any of the methods described herein and known in the art).

In some embodiments, one or more additional therapeutic agents can be administered to the subject. The additional therapeutic agent can comprise one or more inhibitors selected from the group consisting of an inhibitor of B-Raf, an EGFR inhibitor, an inhibitor of a MEK, an inhibitor of ERK, an inhibitor of K-Ras, an inhibitor of c-Met, an inhibitor of anaplastic lymphoma kinase (ALK), an inhibitor of a phosphatidylinositol 3-kinase (PI3K), an inhibitor of an Akt, an inhibitor of mTOR, a dual PI3K/mTOR inhibitor, an inhibitor of Bruton's tyrosine kinase (BTK), and an inhibitor of Isocitrate dehydrogenase 1 (IDH1) and/or Isocitrate dehydrogenase 2 (IDH2). In some embodiments, the additional therapeutic agent is an inhibitor of indoleamine 2,3-dioxygenase-1) (IDO1) (e.g., epacadostat).

In some embodiments, the additional therapeutic agent can comprise one or more inhibitors selected from the group consisting of an inhibitor of HER3, an inhibitor of LSD1, an inhibitor of MDM2, an inhibitor of BCL2, an inhibitor of CHK1, an inhibitor of activated hedgehog signaling pathway, and an agent that selectively degrades the estrogen receptor.

In some embodiments, the additional therapeutic agent can comprise one or more therapeutic agents selected from the group consisting of Trabectedin, nab-paclitaxel, Trebananib, Pazopanib, Cediranib, Palbociclib, everolimus, fluoropyrimidine, IFL, regorafenib, Reolysin, Alimta, Zykadia, Sutent, temsirolimus, axitinib, everolimus, sorafenib, Votrient, Pazopanib, IMA-901, AGS-003, cabozantinib, Vinflunine, an Hsp90 inhibitor, Ad-GM-CSF, Temazolomide, IL-2, IFNa, vinblastine, Thalomid, dacarbazine, cyclophosphamide, lenalidomide, azacytidine, lenalidomide, bortezomid, amrubicine, carfilzomib, pralatrexate, and enzastaurin.

In some embodiments, the additional therapeutic agent can comprise one or more therapeutic agents selected from the group consisting of an adjuvant, a TLR agonist, tumor necrosis factor (TNF) alpha, IL-1, HMGB1, an IL-10 antagonist, an IL-4 antagonist, an IL-13 antagonist, an IL-17 antagonist, an HVEM antagonist, an ICOS agonist, a treatment targeting CX3CL1, a treatment targeting CXCL9, a treatment targeting CXCL10, a treatment targeting CCL5, an LFA-1 agonist, an ICAM1 agonist, and a Selectin agonist.

In some embodiments, carboplatin, nab-paclitaxel, paclitaxel, cisplatin, pemetrexed, gemcitabine, FOLFOX, or FOLFIRI are administered to the subject.

In some embodiments, the additional therapeutic agent is an anti-OX40 antibody, an anti-PD-1 antibody, an anti-PD-L1 antibody, an anti-PD-L2 antibody, an anti-LAG-3 antibody, an anti-TIGIT antibody, an anti-BTLA antibody, an anti-CTLA-4 antibody, or an anti-GITR antibody.

Pharmaceutical Compositions and Routes of Administration

Also provided herein are pharmaceutical compositions that contain at least one (e.g., one, two, three, or four) of the antibodies, antigen-binding fragments, or antibody-drug conjugates described herein. Two or more (e.g., two, three, or four) of any of the antibodies, antigen-binding fragments, or antibody-drug conjugates described herein can be present in a pharmaceutical composition in any combination. The pharmaceutical compositions may be formulated in any manner known in the art.

Pharmaceutical compositions are formulated to be compatible with their intended route of administration (e.g., intravenous, intraarterial, intramuscular, intradermal, subcutaneous, or intraperitoneal). The compositions can include a sterile diluent (e.g., sterile water or saline), a fixed oil, polyethylene glycol, glycerine, propylene glycol or other synthetic solvents, antibacterial or antifungal agents, such as benzyl alcohol or methyl parabens, chlorobutanol, phenol, ascorbic acid, thimerosal, and the like, antioxidants, such as ascorbic acid or sodium bisulfite, chelating agents, such as ethylenediaminetetraacetic acid, buffers, such as acetates, citrates, or phosphates, and isotonic agents, such as sugars (e.g., dextrose), polyalcohols (e.g., mannitol or sorbitol), or salts (e.g., sodium chloride), or any combination thereof. Liposomal suspensions can also be used as pharmaceutically acceptable carriers (see, e.g., U.S. Pat. No. 4,522,811). Preparations of the compositions can be formulated and enclosed in ampules, disposable syringes, or multiple dose vials. Where required (as in, for example, injectable formulations), proper fluidity can be maintained by, for example, the use of a coating, such as lecithin, or a surfactant. Absorption of the antibody or antigen-binding fragment thereof can be prolonged by including an agent that delays absorption (e.g., aluminum monostearate and gelatin). Alternatively, controlled release can be achieved by implants and microencapsulated delivery systems, which can include biodegradable, biocompatible polymers (e.g., ethylene vinyl acetate, polyanhydrides, polyglycolic acid, collagen, polyorthoesters, and polylactic acid; Alza Corporation and Nova Pharmaceutical, Inc.).

Compositions containing one or more of any of the antibodies, antigen-binding fragments, antibody-drug conjugates described herein can be formulated for parenteral (e.g., intravenous, intraarterial, intramuscular, intradermal, subcutaneous, or intraperitoneal) administration in dosage unit form (i.e., physically discrete units containing a predetermined quantity of active compound for ease of administration and uniformity of dosage).

Toxicity and therapeutic efficacy of compositions can be determined by standard pharmaceutical procedures in cell cultures or experimental animals (e.g., monkeys). One can determine the LD50 (the dose lethal to 50% of the population) and the ED50 (the dose therapeutically effective in 50% of the population): the therapeutic index being the ratio of LD50:ED50. Agents that exhibit high therapeutic indices are preferred. Where an agent exhibits an undesirable side effect, care should be taken to minimize potential damage (i.e., reduce unwanted side effects). Toxicity and therapeutic efficacy can be determined by other standard pharmaceutical procedures.

Data obtained from cell culture assays and animal studies can be used in formulating an appropriate dosage of any given agent for use in a subject (e.g., a human). A therapeutically effective amount of the one or more (e.g., one, two, three, or four) antibodies or antigen-binding fragments thereof (e.g., any of the antibodies or antibody fragments described herein) will be an amount that treats the disease in a subject (e.g., kills cancer cells) in a subject (e.g., a human subject identified as having cancer), or a subject identified as being at risk of developing the disease (e.g., a subject who has previously developed cancer but now has been cured), decreases the severity, frequency, and/or duration of one or more symptoms of a disease in a subject (e.g., a human). The effectiveness and dosing of any of the antibodies or antigen-binding fragments described herein can be determined by a health care professional or veterinary professional using methods known in the art, as well as by the observation of one or more symptoms of disease in a subject (e.g., a human). Certain factors may influence the dosage and timing required to effectively treat a subject (e.g., the severity of the disease or disorder, previous treatments, the general health and/or age of the subject, and the presence of other diseases).

Exemplary doses include milligram or microgram amounts of any of the antibodies or antigen-binding fragments, or antibody-drug conjugates described herein per kilogram of the subject's weight (e.g., about 1 µg/kg to about 500 mg/kg; about 100 µg/kg to about 500 mg/kg; about 100 µg/kg to about 50 mg/kg; about 10 µg/kg to about 5 mg/kg; about 10 µg/kg to about 0.5 mg/kg; or about 1 µg/kg to about 50 µg/kg). While these doses cover a broad range, one of ordinary skill in the art will understand that therapeutic agents, including antibodies and antigen-binding fragments thereof, vary in their potency, and effective amounts can be determined by methods known in the art. Typically, relatively low doses are administered at first, and the attending health care professional or veterinary professional (in the case of therapeutic application) or a researcher (when still working at the development stage) can subsequently and gradually increase the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, and the half-life of the antibody or antibody fragment in vivo.

The pharmaceutical compositions can be included in a container, pack, or dispenser together with instructions for administration. The disclosure also provides methods of manufacturing the antibodies or antigen binding fragments thereof, or antibody-drug conjugates for various uses as described herein.

EXAMPLES

The invention is further described in the following examples, which do not limit the scope of the invention described in the claims.

Example 1: Methods and Materials

The following assays were used in the examples.
Binding Assay
a) Dispense $5\times10^5$ cells in 50 µl of media to each well of 96 well plate.
b) Add 100 µL of antibodies at different dilution into wells.
c) Incubate the plate at room temperature (RT) for 60 min
d) Spin cells down and wash cells×3 with phosphate-buffered saline (PBS) with 0.1 bovine serum albumin (BSA).
e) Resuspend cell pellet in 100 µL of PBS with 0.1% BSA containing 1:500 Cy3 conjugated goat anti-human IgG.
f) Incubate for 30 min at room temperature in the dark.
g) Wash cells 3 times and resuspend in fluorescence-activated cell sorting (FACS) buffer.
h) Analyze the cells on the flow cytometer.

Antibody-Dependent Cellular Cytotoxicity (ADCC) Assay
a) Target cells are washed with PBS one time before Calcein AM labeling.
b) Use 1:333 Calcein AM stock of 2.5 mM to label target cells.
c) Incubate cells at 37° C. for 30 mins preventing from light.
d) Wash cells with PBS three times.
e) Dispense $1\times10^4$ Calcein AM labeled target cells in 50 µL to each well.
f) Add 100 µL of diluted antibodies in wells
g) Incubate the plate at room temperature for 60 minutes.
h) Add $5\times10^4$ of PBMS (effect cells) in 50p of media in each well (E/T ratio is 5).
i) Incubate the plate at 37° C. for 4 hours.
j) Spin cells down, transfer 180 µL of supernatant into another translucent bottom and black wall 96 well plate.
k) Read the plate at wavelength of 485 excitation and 520 emissions.

Complement-Dependent Cytotoxicity (CDC) Assay
a) Target cells were collected and stained with Calcein AM as ADCC (Only for calcein release assay).
b) 50 µL of target cells ($1\times10^5$ cells) were seeded in the well of 96 well plate.
c) 100 µL Antibody was added in wells at different concentration.
d) Incubate the plate at room temperature for 15 min.
e) 50 µL of 10% complements enriched human serum were added to each well (final 5%).
f) Incubate the plate at room temperature for 45 min.
g) Transfer 180 µL of supernatant into another translucent bottom and black wall 96 well plate. (Only for calcein release assay).
h) Wash cells with PBS with 0.1% BSA three times.

i) Staining cells with 2 µL of 7-Aminoactinomycin D (7AAD) per well at room temperature for 15 min in the dark.
j) Wash cells three times and analyze cells on flow cytometer.

T Cell Activation

Pre-activated peripheral blood mononuclear cell (PBMC) were used in some ADCC experiments.
a) Dynabeads (human T-activator CD3/CD28) are used to activate PBMC.
b) After wash with buffer, Dynabeads are added in PBMC at a ratio of 1:1 along with 30 U/mL of Interleukin-2 (IL2).
c) Cell mixture is incubated for sufficient time period.
d) At the end of incubation, beads are removed on a magnet, activated PBMC are then used for ADCC assay.

Cell-Binding Assay Involving MDA231 Cells
a) MDA231 cells are prepared in media at a concentration of $1 \times 10^6$ cells/mL.
b) Dilute antibody sample to an appropriate concentration.
c) Transfer 50 µL of cells into each well of 96 well V-bottom plate.
d) Transfer 50 µL of antibodies into wells of 96 well V-bottom plate.
e) Incubate cell mixture for 60 min at room temperature.
f) Spin cells down and wash twice with FACS buffer.
g) Re-suspend cells in 100 µL FACS buffer containing Cy3 conjugated goat anti-human (GAH) IgG (1:500) in each well.
h) Incubate at room temperature for 30 min, and wash with FACS buffer×2.
i) FACS analysis.

Internalization Assay Involving MDA231 and SIHA Cells
a) Add 50 µL of cell suspension (MDA231 or SIHA cells) at $1 \times 10^6$/m in each well of the 96 plate.
b) Add 50 µL Ab in corresponding well.
c) Incubate at 37° C. for 30 min,
d) Add 100 µL of pHrodo Red labeled GAH IgG in each well and incubate at 37° C. for 24 hours.
e) Trypsinize and harvest cells, wash twice, and then run FACS.

Complement-Dependent Cytotoxicity (CDC) Assay Involving MDA231 Cells
a) Target cells: MDA231 cells were washed with PBS twice and then adjusted to a concentration of $0.5 \times 10^6$/mL in PBS.
b) Seed cells in flat bottom 24 well plate, 300 L/well.
c) Add 300 µL of 20 µg/mL antibodies to the corresponding wells to make a final concentration of 10 µg/mL.
d) Incubate the plate at 37° C. for 48 hours.
e) At the end of incubation, trypsinize cells, wash twice with plain media.
f) Resuspend cell pellets in 100 µL plain media and transfer cells to 96 well plate.
g) Add 100 µL of 10% complement enriched serum in each well.
h) Incubate cells for 4 hours at 37° C.
i) Wash cells twice with FACS buffer.
j) Detach cells by adding 100 µL Trypsin for 3 min.
k) Resuspend cell pellets In FACS buffer containing 7AAD (1:50 dilution)
l) Wash cells twice after 15 min incubation at RT.
m) Run FACS analysis.

Example 2: A Bispecific Antibody that Binds to CD20 and CD3

A bispecific antibody was designed to bind to CD20 and CD3. This bispecific antibody has two common light chains (with identical sequence) and two different heavy chains. The sequences for the variable regions of the two heavy chains and the common light chain are shown below.

VHa for CD20 (Designed from Rituximab VH):

```
                                        (SEQ ID NO: 1)
QVQLQQPGAELVKPGASVKMSCKASGYTFTSYNMHWVKQTPGRGLEWIGA

IYPGNGDTSYNQKFKGKATLTADKSSSTAYMQLSSLrSEDSAVYYCARST

YYGGDWYFNVWGAGTTVTVSA
```

VHb for CD3 (Designed from MAb 12F6 VH):

```
                                        (SEQ ID NO: 2)
EVQLQESGAELARPGASVKMSCKASGYTFTSYTMHWVKQRPGEGLEWIGY

INPSSGYTKYNQKFKDKATLTADKSSSTAYMELSSLTSEDSAVYYCARWQ

DYDVYFDYWGEGTTLTVSS
```

Common VL (Rituximab's VL)

```
                                        (SEQ ID NO: 3)
QIVLSQSPAILSASPGEKVTMTCRASSSVSYIHWFQQKPGSSPKPWIYAT

SNLASGVPVRFSGSGSGTSYSLTISRVEAEDAATYYCQQWTSNPPTFGGG

TKLEIKR
```

The 12F6 antibody is described, e.g., in Construction and characterization of a humanized anti-human CD3 monoclonal antibody 12F6 with effective immunoregulation functions, *Immunology*, 116 (4), 487-498 (2005), which is incorporated herein by reference in its entirety. The sequences for the parental antibodies are also shown below for comparison purpose:

Parental CD20VH (Rituximab VH):

```
                                        (SEQ ID NO: 8)
QVQLQQPGAELVKPGASVKMSCKASGYTFTSYNMHWVKQTPGRGLEWIGA

IYPGNGDTSYNQKFKGKATLTADKSSSTAYMQLSSLTSEDSAVYYCARST

YYGGDWYFNVWGAGTTVTVSA
```

Parental CD20VL (Rituximab):

```
                                        (SEQ ID NO: 9)
QIVLSQSPAILSASPGEKVTMTCRASSSVSYIHWFQQKPGSSPKPWIYAT

SNLASGVPVRFSGSGSGTSYSLTISRVEAEDAATYYCQQWTSNPPTFGGG

TKLEIKR
```

Parental CD3VH (MAb 12F6 VH):

```
                                        (SEQ ID NO: 10)
QVQLQQSGAELARPGASVKMSCKASGYTFTSYTMHWVKQRPGQGLEWIGY

INPSSGYTKYNQKFKDKATLTADKSSSTAYMQLSSLSEDSAVYYCARWQ

DYDVYFDYWGQGTTLTVSS
```

Parental CD3VL (MAb 12F6 VL):

(SEQ ID NO: 11)
QIVLSQSPAILSASPGEKVTMTCRASSSVSYMHWYQQKPGSSPKPWIYAT

SNLASGVPARFSGSGSGTSYSLTISRVEAEDAATYYCQQWSSNPPTFGGG

TKLETKR

The CDR sequences for the redesigned VH and VL are also summarized in the tables below:

TABLE 1

VHa for CD20 heavy chain

|  | CDR-H1 | CDR-H2 | CDR-H3 |
|---|---|---|---|
| Kabat | SYNMH (SEQ ID NO: 16) | AIYPGNGDTSYNQKFKG (SEQ ID NO: 17) | STYYGGDWYFNV (SEQ ID NO: 18) |
| Chothia | GYTFTSY (SEQ ID NO: 19) | YPGNGD (SEQ ID NO: 20) | STYYGGDWYFNV (SEQ ID NO: 21) |

TABLE 2

VHb for CD3 heavy chain

|  | CDR-H1 | CDR-H2 | CDR-H3 |
|---|---|---|---|
| Kabat | SYTMH (SEQ ID NO: 22) | YINPSSGYTKYNQKFKD (SEQ ID NO: 23) | WQDYDVYFDY (SEQ ID NO: 24) |
| Chothia | GYTFTSY (SEQ ID NO: 25) | NPSSGY (SEQ ID NO: 26) | WQDYDVYFDY (SEQ ID NO: 27) |

TABLE 3

VL for common light chain

|  | CDR-L1 | CDR-L2 | CDR-L3 |
|---|---|---|---|
| Kabat | RASSSVSYIH (SEQ ID NO: 28) | ATSNLAS (SEQ ID NO: 29) | QQWTSNPPT (SEQ ID NO: 30) |
| Chothia | RASSSVSYIH (SEQ ID NO: 31) | ATSNLAS (SEQ ID NO: 32) | QQWTSNPPT (SEQ ID NO: 33) |

The 3D (3-dimensional) isoelectric point (PI) for Rituximab Fv (VH+VL) is 9.9, and the 3D PI for 12F6 Fv is 9.8. After redesigning the sequences, the 3D PI for VHa+common VL is 10.0, and the 3D PI for VHb+common VL is 9.1. The PI change does not affect the binding affinity to CD20, and the second antigen binding region still maintains a reasonable binding affinity to CD3. The mutations in the two VH chains are shown in the tables below.

TABLE 4

Modified amino acids in VH (CD20)

| Kabat numbering | Amino acid in parental | Amino acid after the modification |
|---|---|---|
| 83 | T | R |

TABLE 5

Modified amino acids in VH (CD3)

| Kabat numbering | Amino acid in parental | Amino acid after the modification |
|---|---|---|
| 1 | Q | E |
| 6 | Q | E |
| 43 | Q | E |
| 81 | Q | E |
| 105 | Q | E |

Figure 1A:
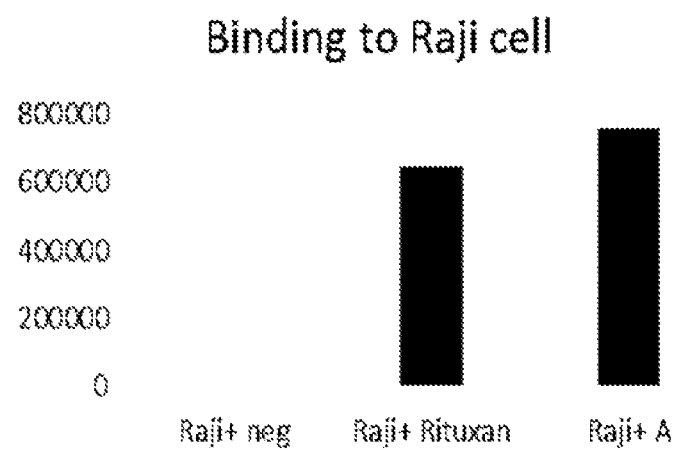
FIG. 1A is a graph showing that redesigned antibody A in Example 1 binds to Raji cells, which express CD20.
Figure 1B:
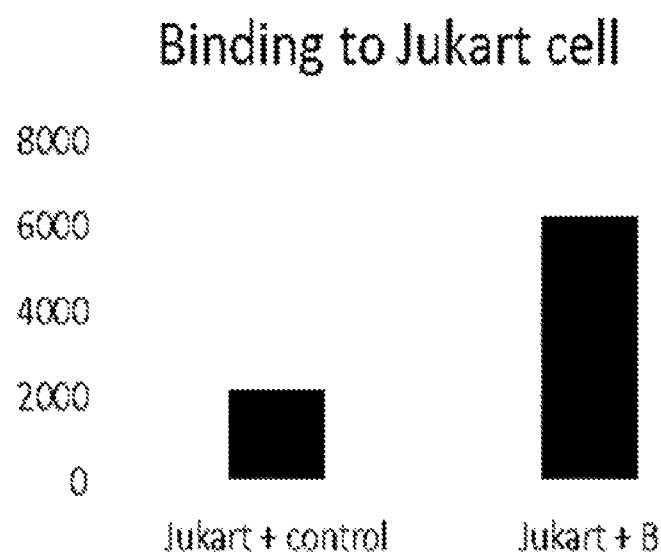
FIG. 1B is a graph showing that redesigned antibody B in Example 1 binds to Jukart cells, which express CD3.

In FIGS. 1A and 1B, antigen binding ability of redesigned Rituximab (antibody A) and redesigned 12F6 (antibody B) were tested respectively. FIG. 1A shows that redesigned Rituximab (antibody A) binds to CD20 positive Raji cells. Antibody A is a homodimer with two VHa (SEQ ID NO: 1) and two common VL (SEQ IN NO: 3). FIG. 1B shows that redesigned 12F6 (antibody B) binds to CD3 positive Jurkart cells. Antibody B is also a homodimer with two VHb (SEQ ID NO: 2) and two common VL (SEQ ID NO: 3). These data suggest the redesigned Rituximab heavy chain, the redesigned 12F6 heavy chain, and the common light chain can be combined into a functional bispecific antibody, e.g., via "knob-into-hole" technology.

Thus, a CD20/CD3 "imbalanced bispecific antibody" was designed. Knob and hole mutations were also introduced into the constant regions of heavy chain to facilitate the formation of the bispecific antibody.

The full-length sequence of the heavy chain and the light chain are shown below:

Full Length for CD20 Heavy Chain Version 1 (Wildtype IgG1 Fc)

(SEQ ID NO: 34)
QVQLQQPGAELVKPGASVKMSCKASGYTFTSYNMHWVKQTPGRGLEWIGA

IYPGNGDTSYNQKFKGKATLTADKSSSTAYMQLSSLRSEDSAVYYCARST

YYGGDWYFNVWGAGTTVTVSAASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSPG

K

Full Length for CD20 Heavy Chain Version 2 (IgG1 Fc with Y407T (Hole) Mutation):

(SEQ ID NO: 35)
QVQLQQPGAELVKPGASVKMSCKASGYTFTSYNMHWVKQTPGRGLEWIGA

IYPGNGDTSYNQKFKGKATLTADKSSSTAYMQLSSLRSEDSAVYYCARST

YYGGDWYFNVWGAGTTVTVSAASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQY

-continued
NSTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPP

VLDSDGSFFLTSKLTVDKSRWQQGNVFSCSVMHEALHNHYTQKSLSLSPG

K

Full Length for CD20 Heavy Chain Version 3 (IgG1 Fc with T366Y (Knob) Mutation):

(SEQ ID NO: 36)
QVQLQQPGAELVKPGASVKMSCKASGYTFTSYNMHWVKQTPGRGLEWIGA

IYPGNGDTSYNQKFKGKATLTADKSSSTAYMQLSSLRSEDSAVYYCARST

YYGGDWYFNVWGAGTTVTVSAASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSREEMTKNQVSLYCLVKGFYPSDIAVEWESNGQPENNYKTTPP

VLDSDGSFFLYSKLTVDKSRWQQGNVFSCSVMHEALHNHYTQKSLSLSPG

K

Full Length for CD3 Heavy Chain Version 1 (Wildtype IgG1 Fc):

(SEQ ID NO: 37)
EVQLQESGAELARPGASVKMSCKASGYTFTSYTMHWVKQRPGEGLEWIGY

INPSSGYTKYNQKFKDKATLTADKSSSTAYMELSSLTSEDSAVYYCARWQ

DYDVYFDYWGEGTTLTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK

Full Length for CD3 Heavy Chain Version 2 (IgG1 Fc with T366Y (Knob) Mutation):

(SEQ ID NO: 38)
EVQLQESGAELARPGASVKMSCKASGYTFTSYTMHWVKQRPGEGLEWIGY

INPSSGYTKYNQKFKDKATLTADKSSSTAYMELSSLTSEDSAVYYCARWQ

DYDVYFDYWGEGTTLTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLYCLVKGFYPSDIAVEWESNGQPENNYKTTPPVL

DSDGSFFLYSKLTVDKSRWQQGNVFSCSVMHEALHNHYTQKSLSLSPGK

Full Length for CD3 Heavy Chain Version 3 (IgG1 Fc with Y407T (Hole) Mutation):

(SEQ ID NO: 39)
EVQLQESGAELARPGASVKMSCKASGYTFTSYTMHWVKQRPGEGLEWIGY

INPSSGYTKYNQKFKDKATLTADKSSSTAYMELSSLTSEDSAVYYCARWQ

DYDVYFDYWGEGTTLTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLTSKLTVDKSRWQQGNVFSCSVMHEALHNHYTQKSLSLSPGK

Full Length for Common Light Chain:

(SEQ ID NO: 40)
QIVLSQSPAILSASPGEKVTMTCRASSSVSYIHWFQQKPGSSPKPWIYAT

SNLASGVPVRFSGSGSGTSYSLTISRVEAEDAATYYCQQWTSNPPTFGGG

TKLEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC

The IgG1 heavy chain for CD20 with a Y407T (EU numbering) (version 2; SEQ ID NO: 35), and the IgG1 heavy chain for CD3 has a T366Y (EU numbering) mutation (version 2; SEQ ID NO: 38) were selected to make the bispecific antibody for further experiments. This bispecific antibody also has two common light chains (SEQ ID NO: 40).

This imbalanced bispecific antibody also includes the following features: (1) CD3 binding affinity was significantly reduced to increase safety; (2) ADCC/CDC effector functions were maintained in order to broaden clinical implementation; (3) Biochemical and biophysical features of the CD20 binding arm and the CD3 binding arm were differentiated to enable better isolation of bispecific antibody during downstream purification process.

As shown in the following examples, this antibody had better CD20+ Raji cell killing efficacy than that of CD20 homodimer and Rituximab in the presence of human PBMCs. Meanwhile, this antibody failed to kill CD3+ Jurkat cells or deplete normal T cell under the same condition. Therefore, this antibody illustrates promising wider clinical applications than current anti-CD20 cancer therapies: 1) as compared to Rituximab, this antibody has T cell recruiting function; 2) compared to CAR-T/other T cell recruiting therapies, this antibody maintains functional effector function; 3) this antibody do not show any safety concern in vitro. Taken together, the CD20/CD3 bispecific antibody and the platform described in this disclosure can address the unmet needs in the field of targeted cancer therapies.

Figure 20:
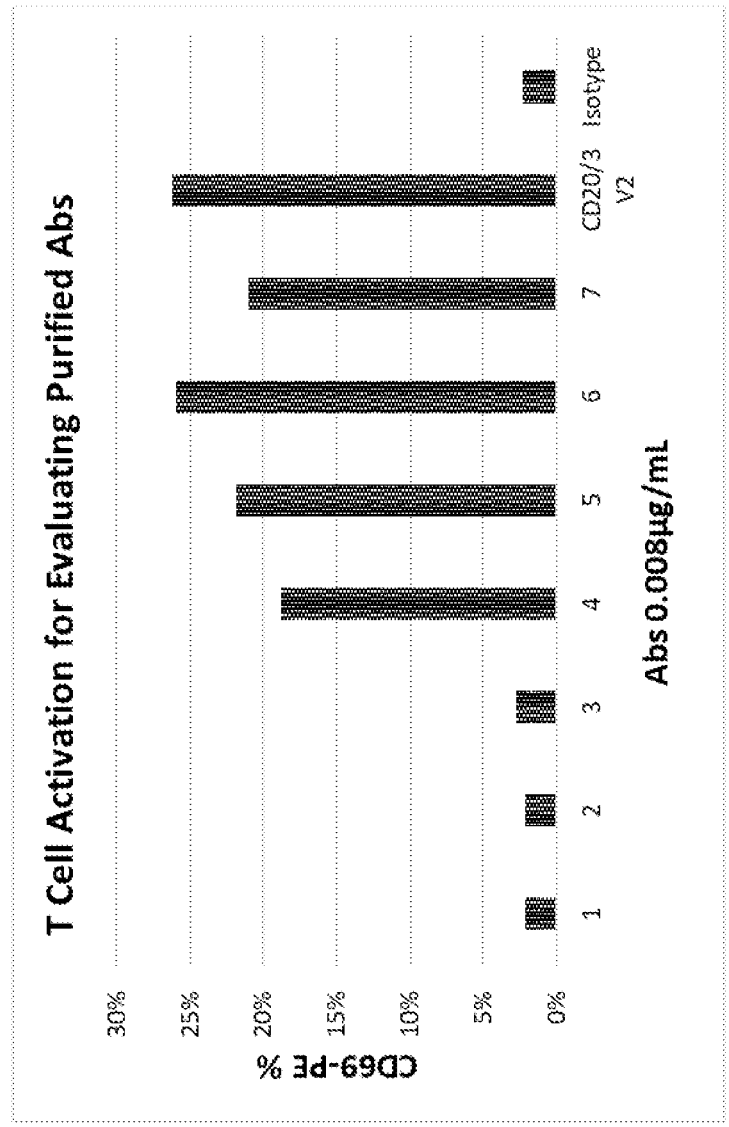
FIG. 20. T cell activation for evaluating purified antibodies.

The bispecific antibody disclosed herein were purified through two steps: affinity purification using Protein A (Round 1) and anion exchange purification using monoQ5/50 (Round 2). In the second round, gradient pH buffer (e.g., PBS) was used to elute the antibodies. T cell activation assay was performed to evaluate different fractions after elution. In FIG. 20, the numbers indicate different fractions. Only CD20/CD3 bispecific antibodies can activate T cells, thus the T cell activation assay can evaluate the purity and the content of CD20/CD3 bispecific antibodies in each fraction. The results indicated that Fractions 4-7 had relatively pure CD20/CD3 bispecific antibodies and demonstrated that the CD20/CD3 bispecific antibodies can be purified by the methods described herein.

Furthermore, the pI for the antibodies described herein have also been determined. This information can be useful to select appropriate pH for elution.

TABLE 6

|  | PI |
|---|---|
| CD20/CD3 BsAb version 1 | 8.48 |
| CD20 homodimer version 1 | 8.72 |
| CD3 homodimer version 1 | 8.09 |
| CD20/CD3 BsAb version 2 | 8.48 |
| CD20 homodimer version 2 | 8.73 |
| CD3 homodimer version 2 | 8.09 |
| CD20/CD3 BsAb version 3 | 8.48 |
| CD20 homodimer version 3 | 8.72 |
| CD3 homodimer version 3 | 8.09 |
| CD20 parental Ab | 8.66 |
| CD3 parental Ab | 8.59 |

Example 3: Binding Affinities for the Bispecific Antibody

Figure 2A:
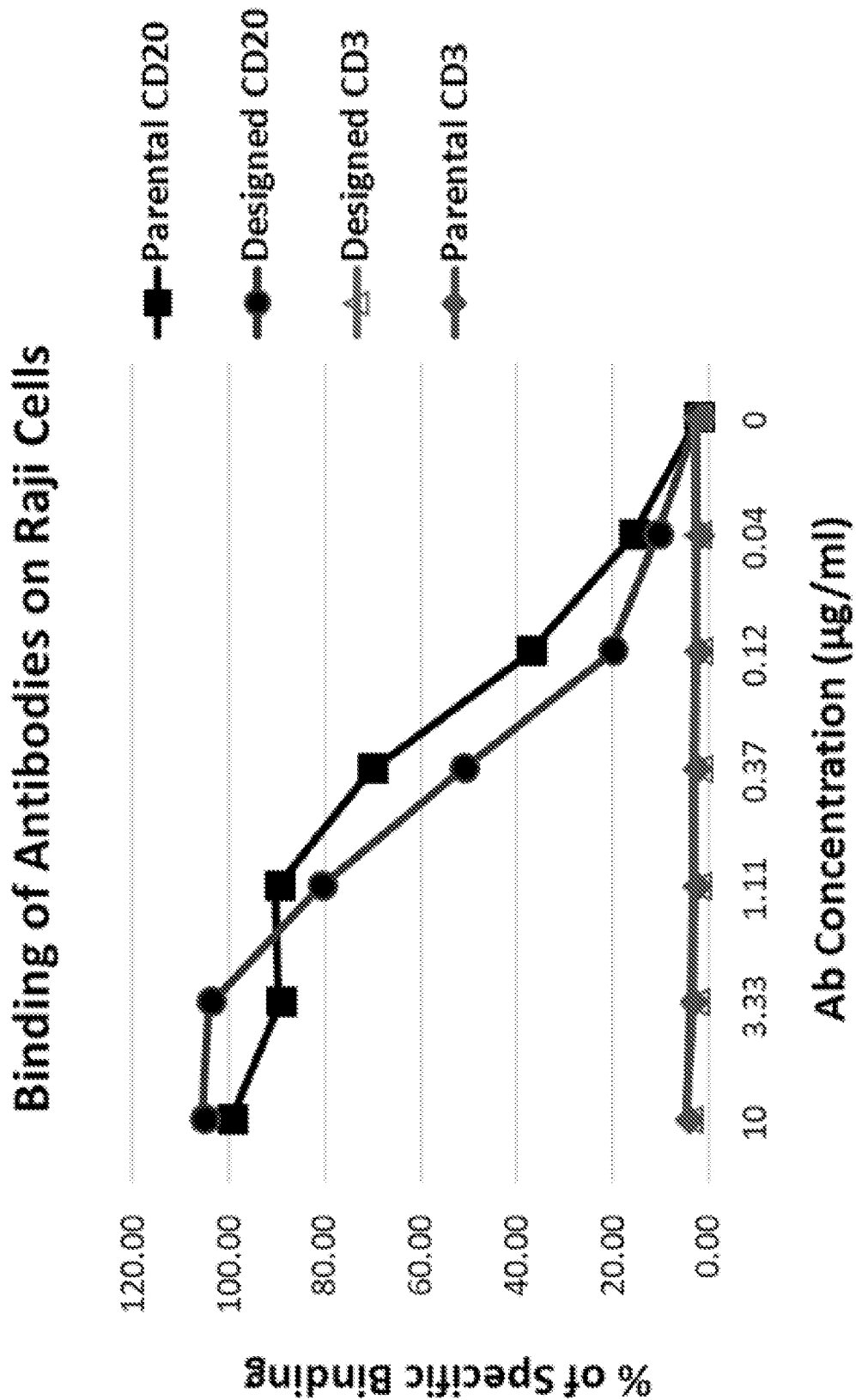
FIG. 2A. Results from CD20+ Raji cell binding assay.

After computational design, CD20 homodimer IgG containing the designed VH sequence (SEQ ID NO: 1) and the common VL sequence (SEQ ID NO: 3) showed similar binding capacity for CD20 compared to that of parental anti-CD20 IgG (Parental CD20). The cell binding affinity assay was performed with Raji cells (expressing CD20). The binding results were shown in FIG. 2A.

Figure 2B:
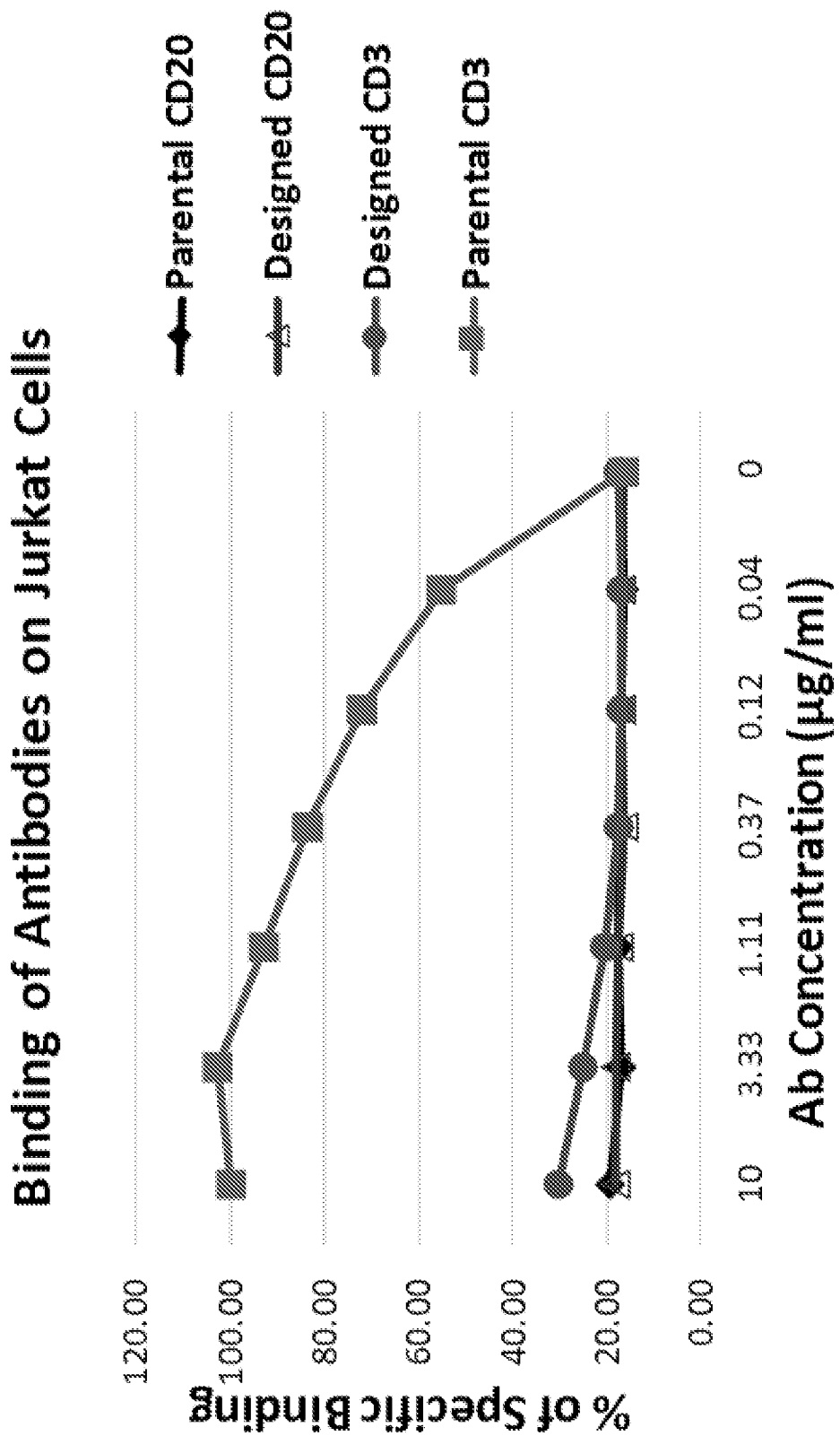
FIG. 2B. Results from CD3+ Jurkat cell binding assay.

CD3 homodimer IgG containing the designed VH sequence (SEQ ID NO: 2) and the common VL sequence (SEQ ID NO: 3) had reduced binding capacity for CD3 compared to that of parental anti-CD3 IgG (Parental CD3). The cell binding affinity assay was performed with Jurkat cells (expressing CD3). The binding results were shown in FIG. 2B.

Example 4: Activation of T Cells by Imbalanced CD20/CD3 Bispecific Antibody

Imbalanced CD20/CD3 bispecific monoclonal antibody (BsMab) activated T cells only in the presence of target tumor cells. The following experiments were performed by using Raji cells as CD20+ target tumor cells, 293 cells as CD20– control cells, and Jurkat cells as T cell models to test whether CD20/CD3 BsMab can activate T cells in the presence of target tumor cells because of the cluster formed by multiple BsMabs that bind to both T cells and target tumor cells. In contrast, CD20/CD3 BsMab cannot activate T cells in the presence of CD20– control cells due to the weak binding of one arm to CD3 on T cell.

The following experiment procedure was used in this example:
1) Separately seed Raji & Jurkat, Jurkat & 293 1×10⁵ in U bottom 96 well plate.
2) Add the test antibody and incubate overnight (19 hrs).
3) Wash the cells one time with PBS+0.1% BSA.
4) Add anti-human CD69 antibody (labeled with PE) (1.5 ul/well) and incubate 30 minutes at room temperature.
5) Wash cells once.
6) Readout.

Figure 3:
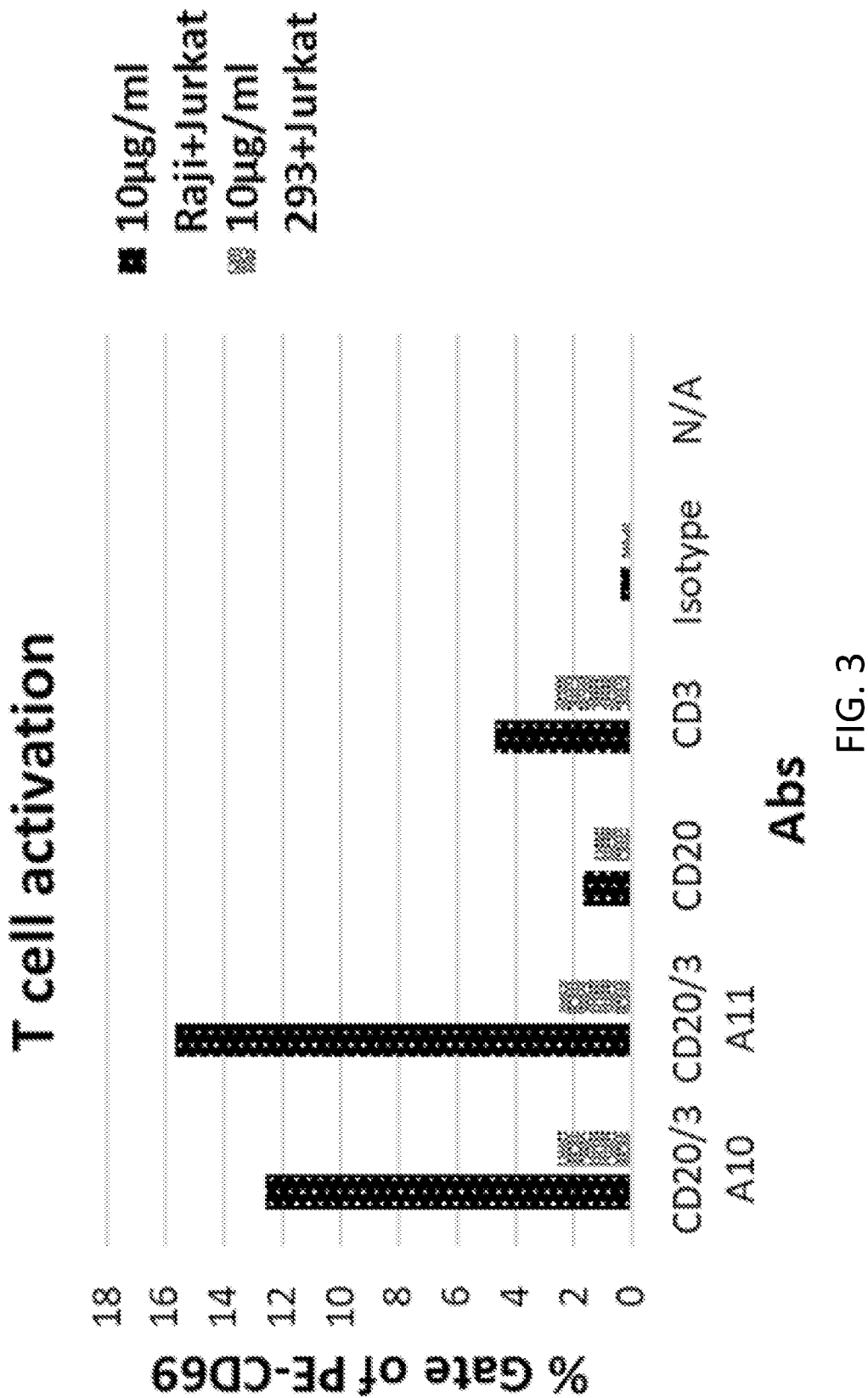
FIG. 3. T cell activation assay (CD20/3 in the figure is the CD20/CD3 BsMab; A10 and A11 indicate different elution fractions; isotype is an IgG1 antibody, which was used as a control).
Figure 4:
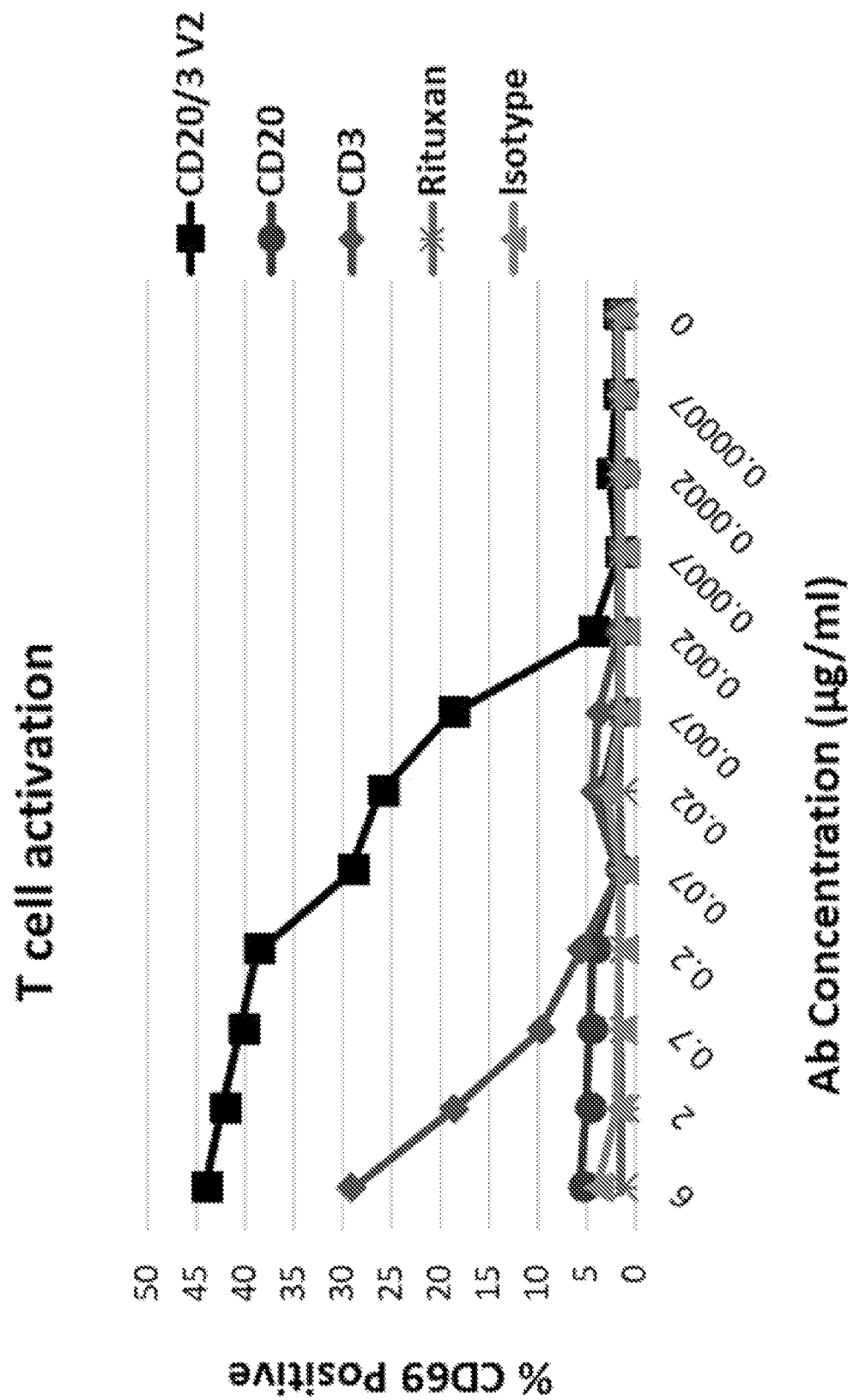
FIG. 4. Titration Curve of T cell activation for different antibodies.

The results were shown in FIG. 3. T cell activation potency in the presence of Raji cells with different concentrations of the test antibody is shown in FIG. 4. Isotype antibodies (non-specific IgG1 antibodies) were used as controls. The T cell activation was measured by the expression of CD69 on the Jurkat cell surface.

Example 5: Imbalanced CD20/CD3 BsMab Induce PBMC Mediated Cell Killing

Imbalanced CD20/CD3 BsMab induced better PBMC mediated cell killing than Rituximab and CD20 homodimer antibody pre- and post-T cell activation.

Figure 5:
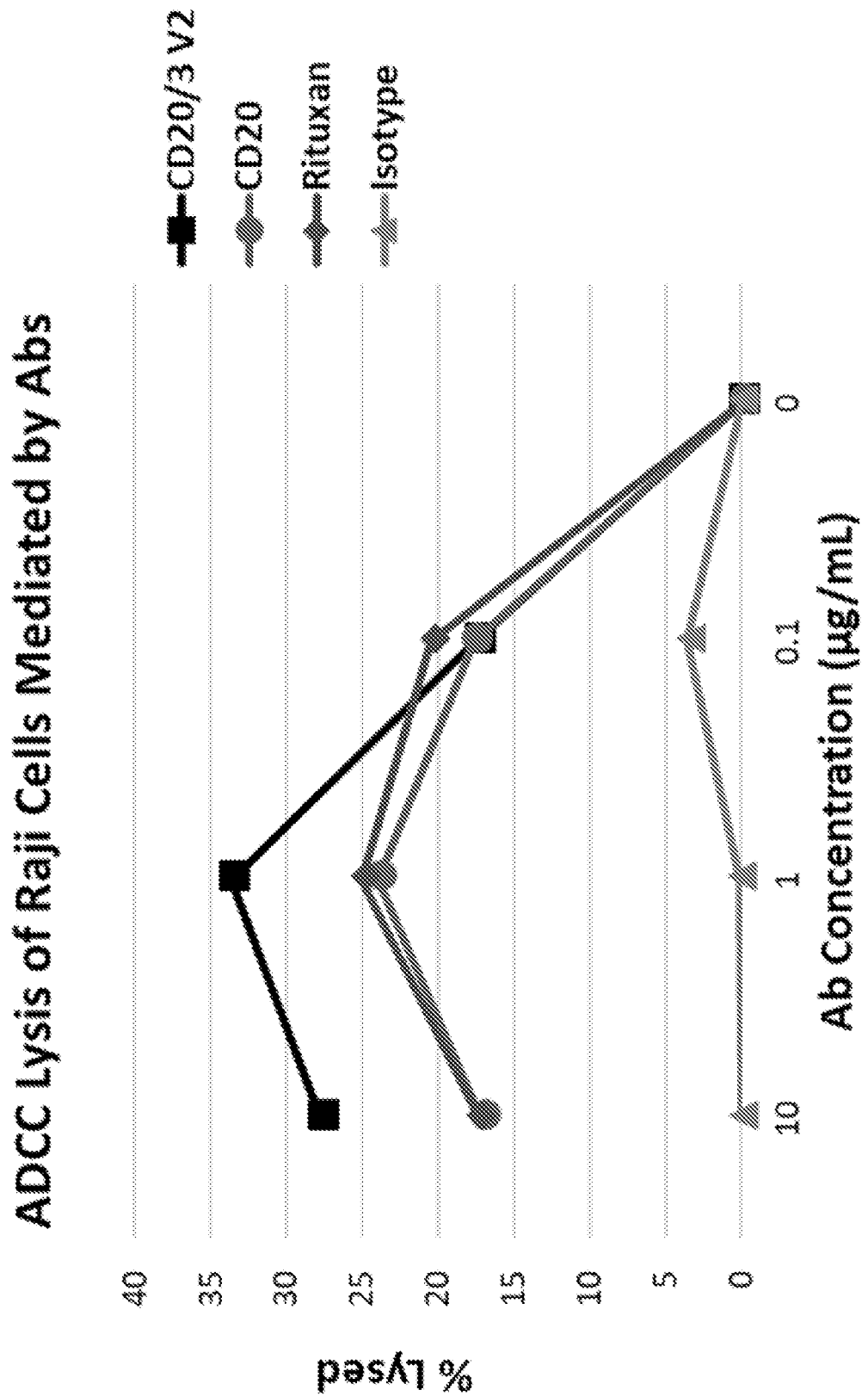
FIG. 5. Antibody mediated CD20+ Raji cell killing in the presence of peripheral blood mononuclear cell (PBMC).

Pre-T cell activation: Fresh peripheral blood mononuclear cells (PBMC) from a healthy donor were subject to resting over night at 37° C. and were incubated with Calcein labeled CD20+ Raji cell in the presence of different antibodies as indicated in the figure for 4 hours. Cell death rate was measured by calcein release. The results are shown in FIG. 5.

Figure 6:
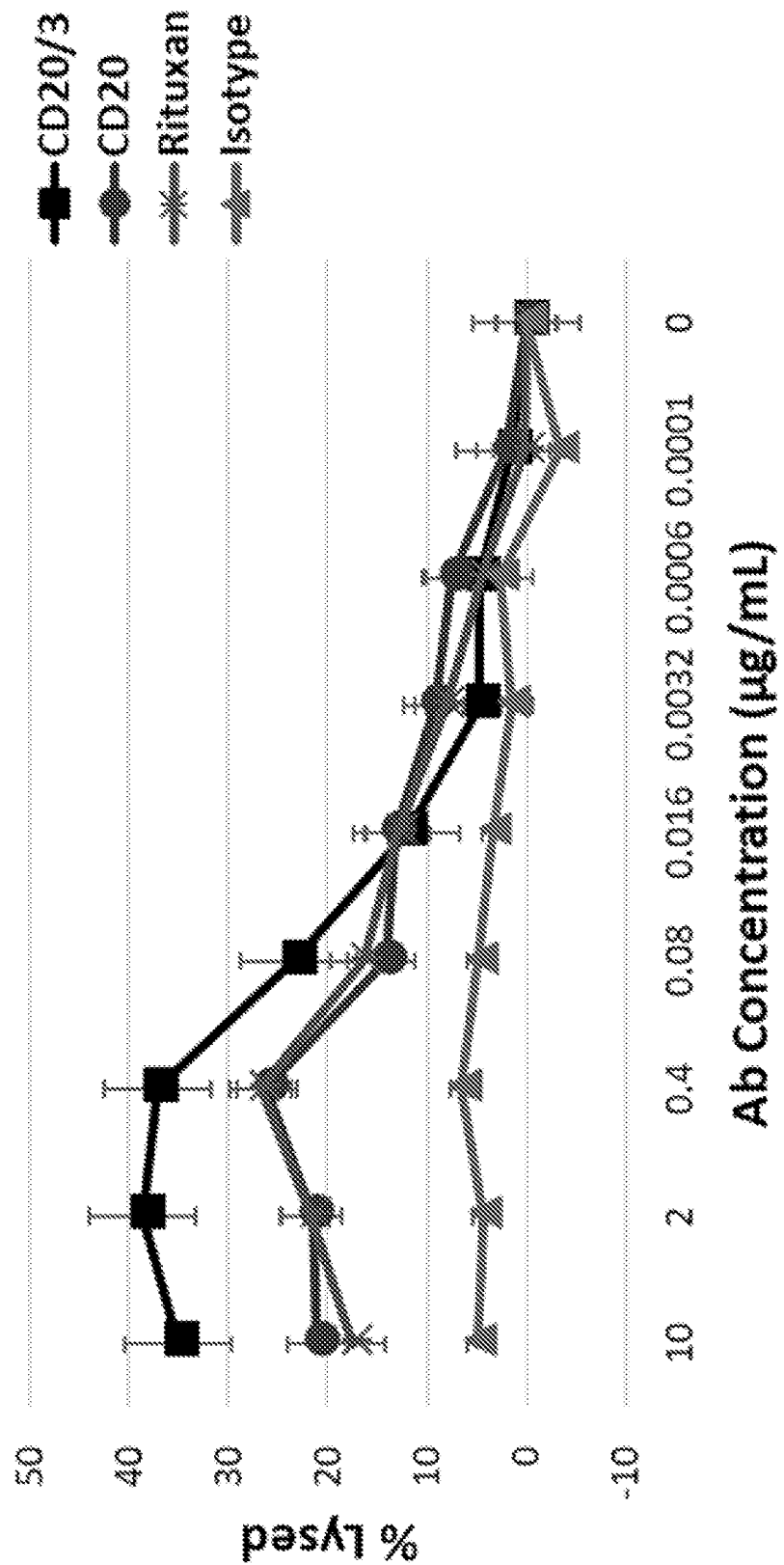
FIG. 6. Antibody mediated CD20+ Raji Cell killing in the presence of PBMC in which T cells were activated by IL-2 and CD3/CD28 beads for 4 days.

Post-T cell activation (4 days): Fresh PBMCs from a healthy donor were incubated with recombinant IL-2 and CD3/CD28 beads for 4 days to activate T cells followed by incubating with Calcein labeled CD20+ Raji cell and different antibodies as indicated in the figure for 2 hours. Cell death rate was measured by calcein release. The results are shown in FIG. 6.

Figure 7:
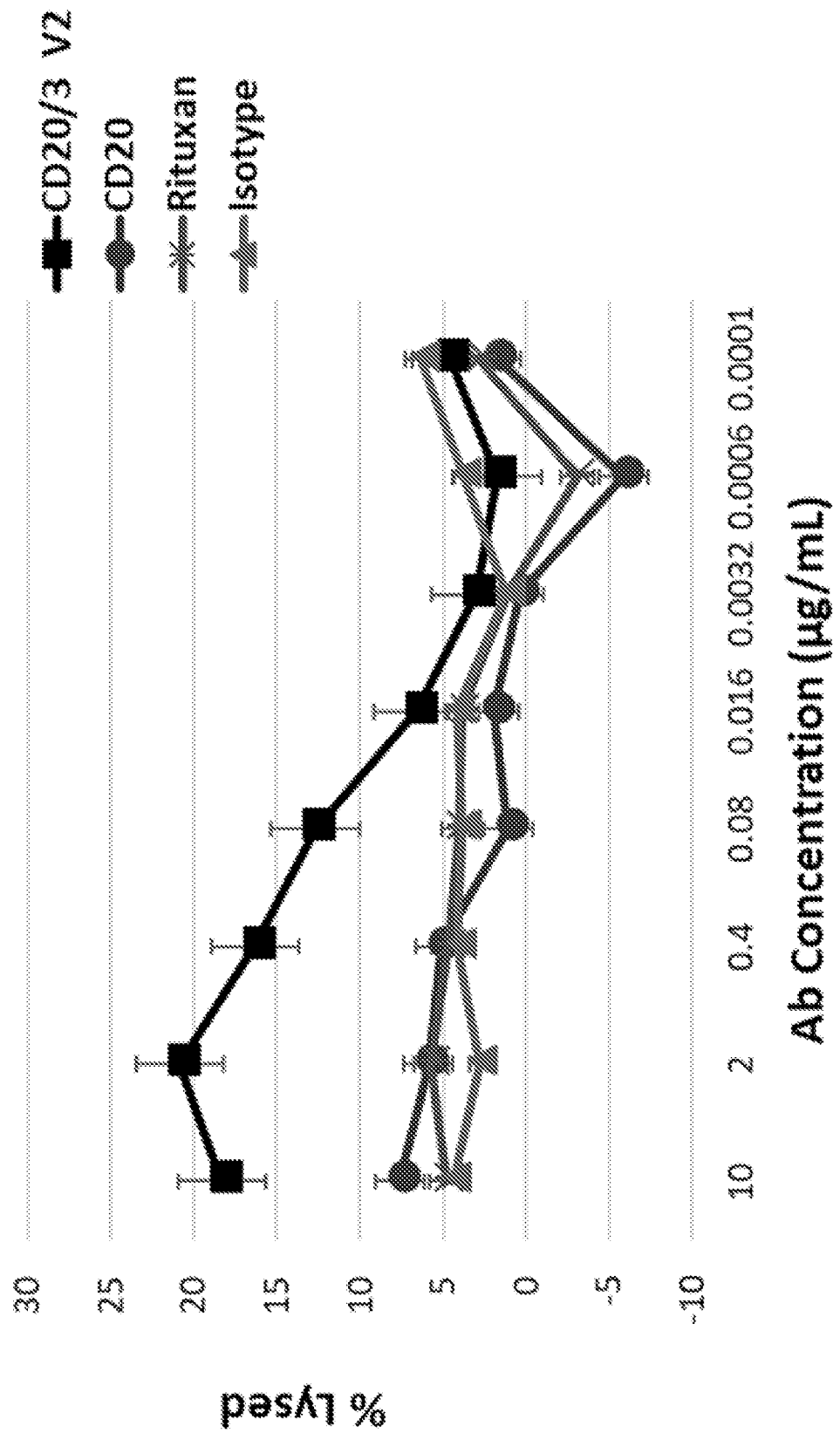
FIG. 7. Antibody mediated CD20+ Raji Cell killing in the presence of PBMC in which T cells were activated by IL-2 and CD3/CD28 beads for 7 days.

Post-T cell activation (7 days): Fresh PBMCs from a healthy donor were incubated with recombinant IL-2 and CD3/CD28 beads for 7 days to activate T cells followed by incubating with Calcein labeled CD20+ Raji cell and different antibodies as indicated in the figure for 2 hours. Cell death rate was measured by calcein release. Results are shown in FIG. 7.

Figure 8:
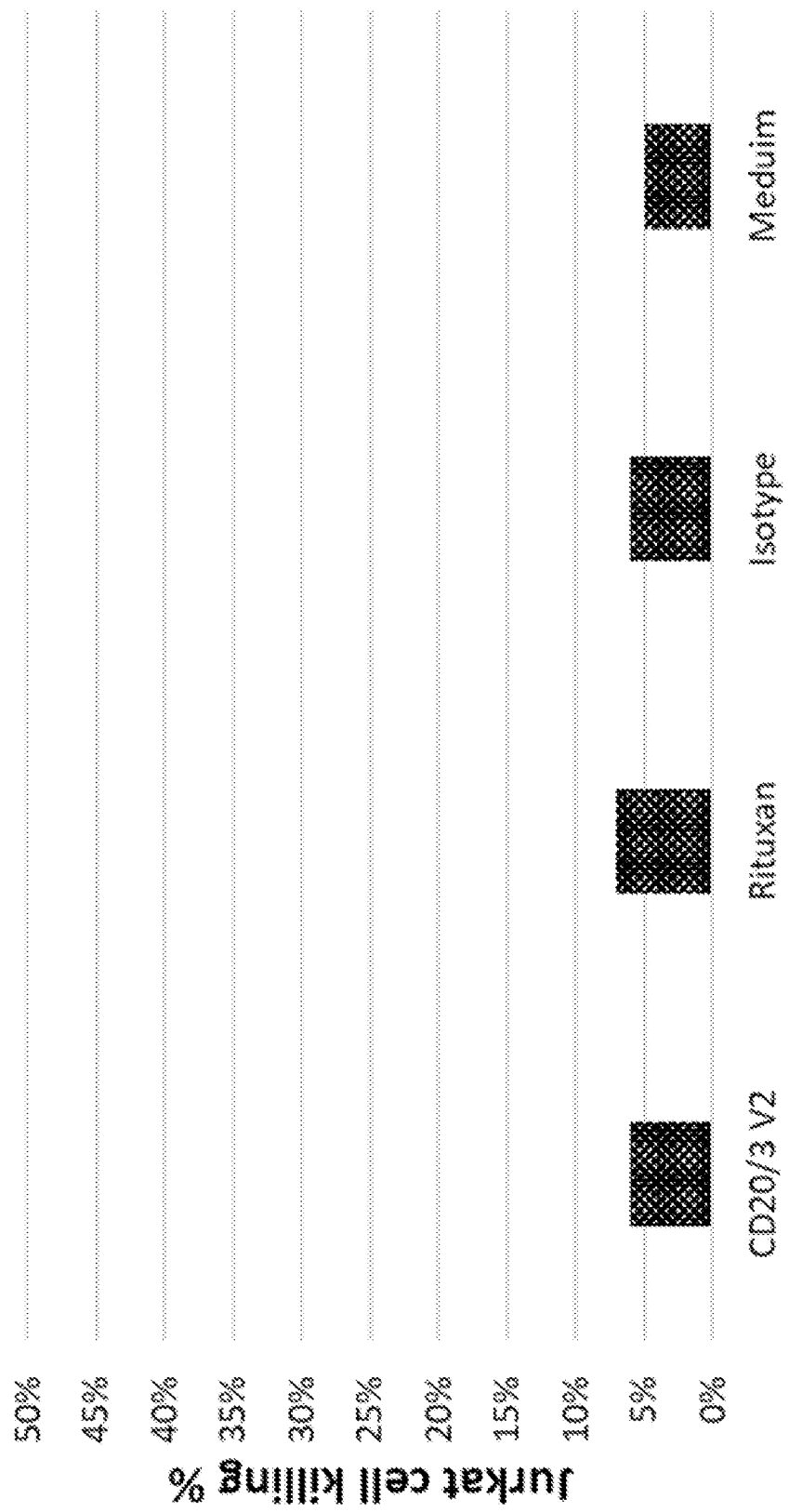
FIG. 8. Antibody mediated CD3+ Jurkat Cell killing in the presence of PBMC.
Figure 9:
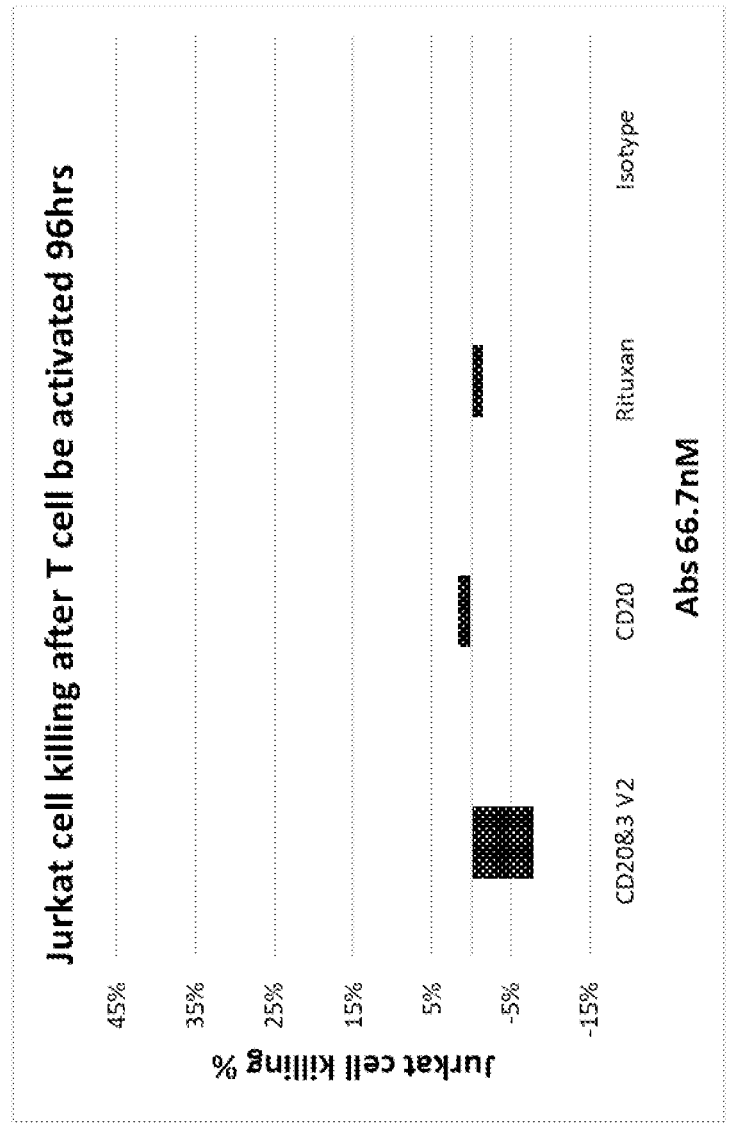
FIG. 9. Antibody mediated CD3+ Jurkat Cell killing in the presence of PBMC in which T cells were activated by IL-2 and CD3/CD28 beads for 4 days.
Figure 10:
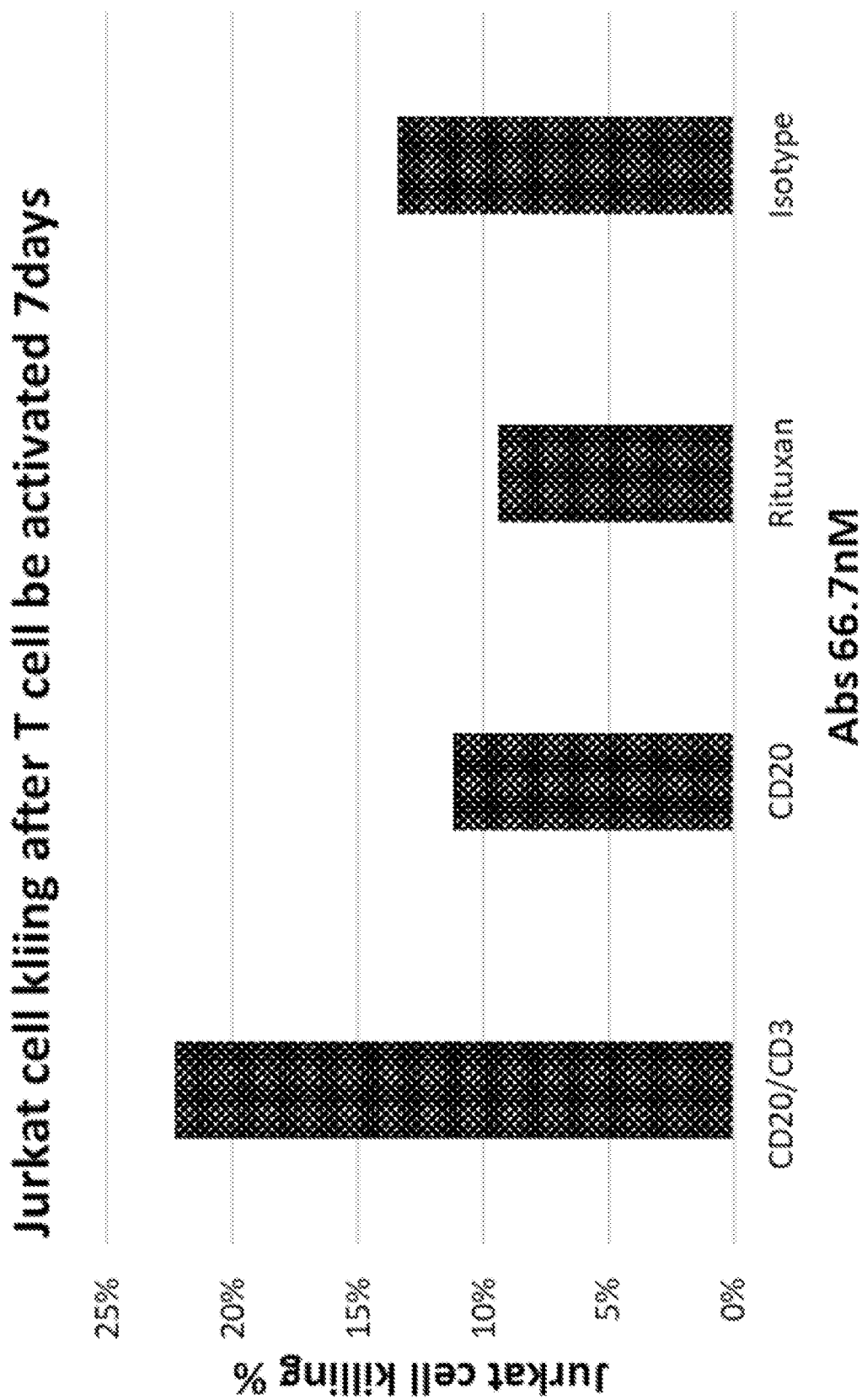
FIG. 10. Antibody mediated CD3+ Jurkat cell killing in the presence of PBMC in which T cells were activated by IL-2 and CD3/CD28 beads for 7 days.

To address the safety concern of whether imbalanced CD20/CD3 BsMab also kill CD3+ T cells under the same condition as indicated in the PBMC killing assays, for each experiment, CD3+ Jurkat cells were used as the control. Only the highest antibody concentration (10 ug/ml) was tested. Pre-T cell activation results are shown in FIG. 8. Post T cell activation (4 days) results are shown in FIG. 9. Post T cell activation (7 days) results are shown in FIG. 10. The number of Jurkat cells in the group treated with PBS was set as the baseline. Thus, the killing percentage would be zero if the number of Jurkat cells is equivalent to the group treated with PBS. The killing percentage would be negative if the number of cells is more than the group treated with PBS.

Figure 11:
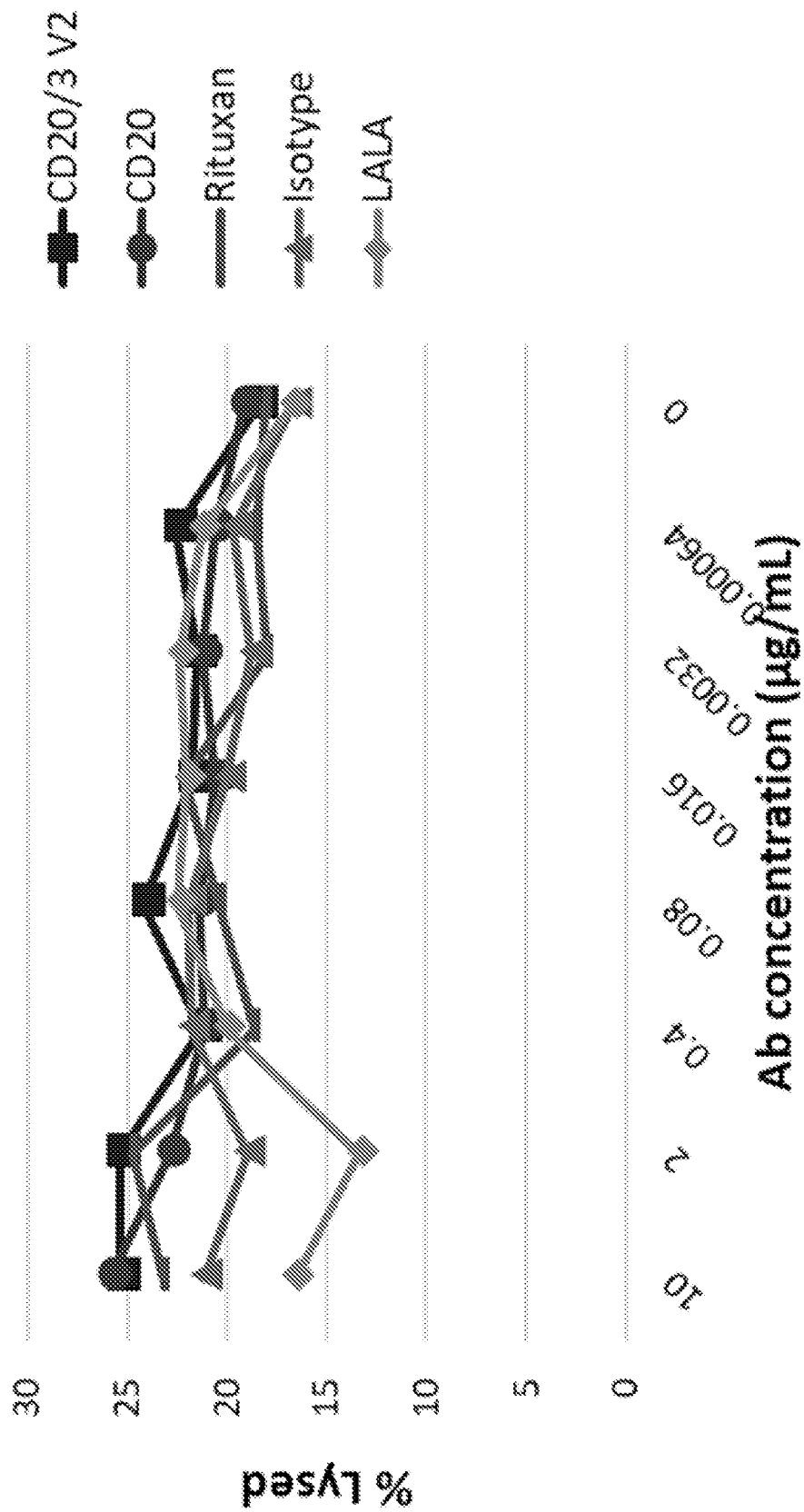
FIG. 11. Depletion of activated T cells in PBMC induced by antibodies.

The results showed that no Jurkat cell killing was observed pre-T cell activation and at 4 days post T cell activation. However, Jurkat killing was observed at 7 days post T cell activation, under which condition Rituximab and CD20 homodimer IgG induced no Raji cell killing. This suggests the 7 day Jurkat cell killing may be caused by T cell super-activation. To further test whether 7 day activated natural T cell themselves were also killed in the presence of imbalanced CD20/CD3 BsMab, the same 7 day activated PBMCs were incubated with different antibodies as indicated in the figure overnight and T cell depletion status was checked. The results are shown in FIG. 11. LALA in the figure is the CD20/CD3 BsMab with L234A and L235A mutations (EU numbering). The antibody with L234A and L235A mutations does not have Fc effector function, which was used as a negative control.

Example 6: T-Cell Depletion by Imbalanced Bispecific CD20/CD3 Antibody

Experiments were also preformed to test whether pre-activated T cell can be depleted by imbalanced CD20/CD3 BsMab.

Figure 12:
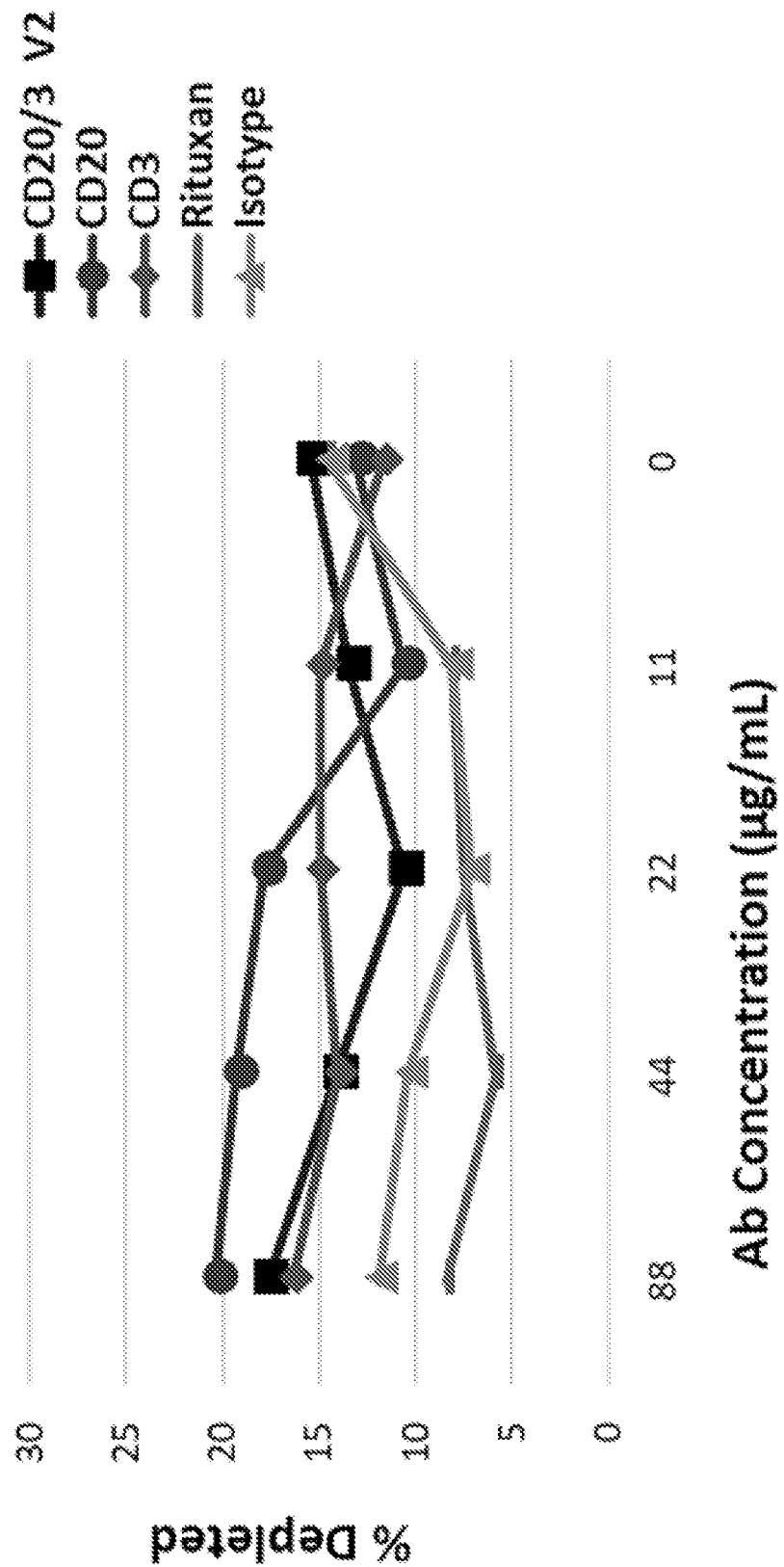
FIG. 12. Depletion of inactivated T cells in PBMC induced by antibodies.

FIG. 12 shows that non-activated T cell in PBMC were not depleted by imbalanced CD20/CD3 BsMab after overnight incubation.

Example 7: Induction of Complement Dependent Cytotoxicity

Figure 13:
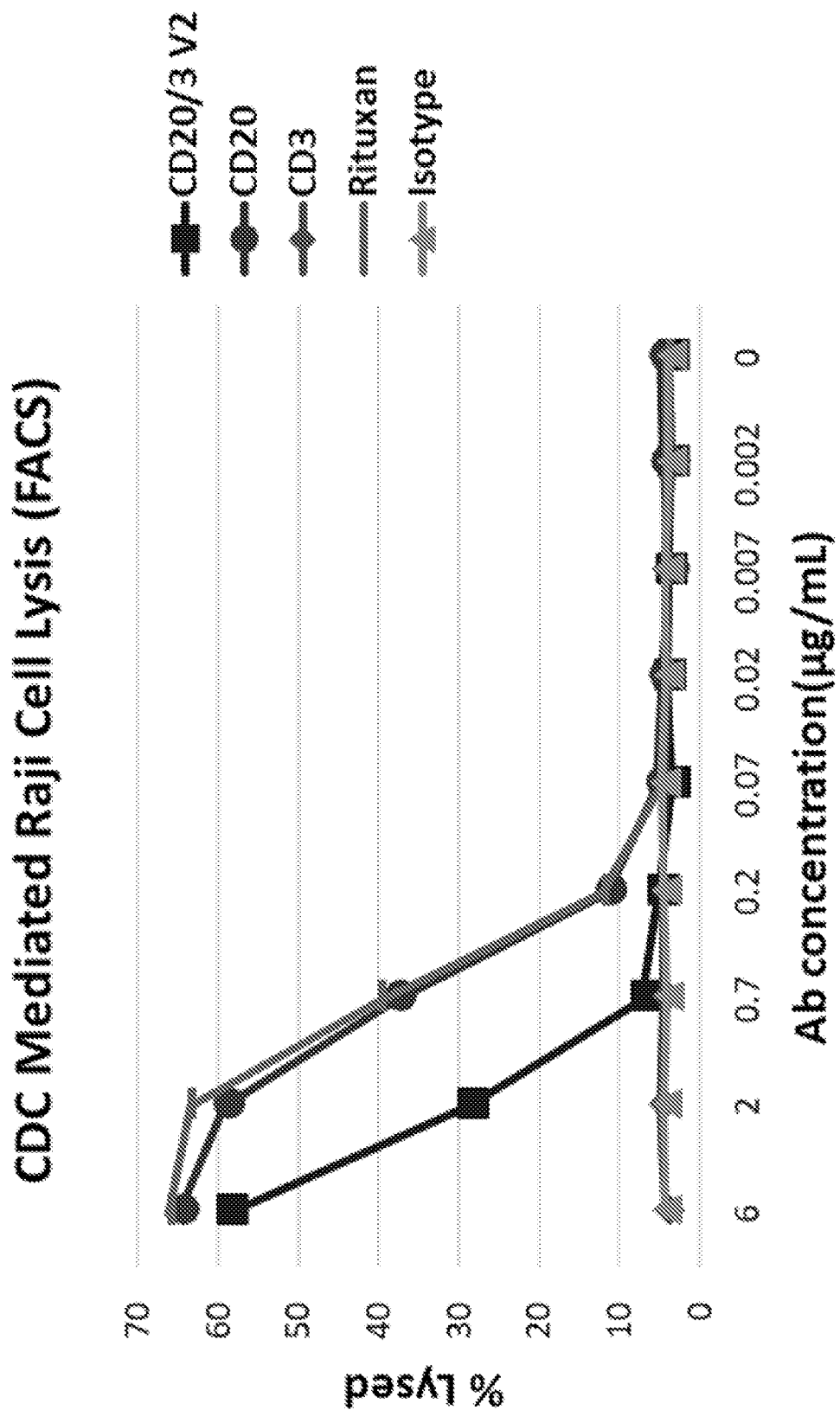
FIG. 13. Raji cell lysis mediated by Complement Dependent Cytotoxicity (CDC) as determined by FACS.
Figure 14:
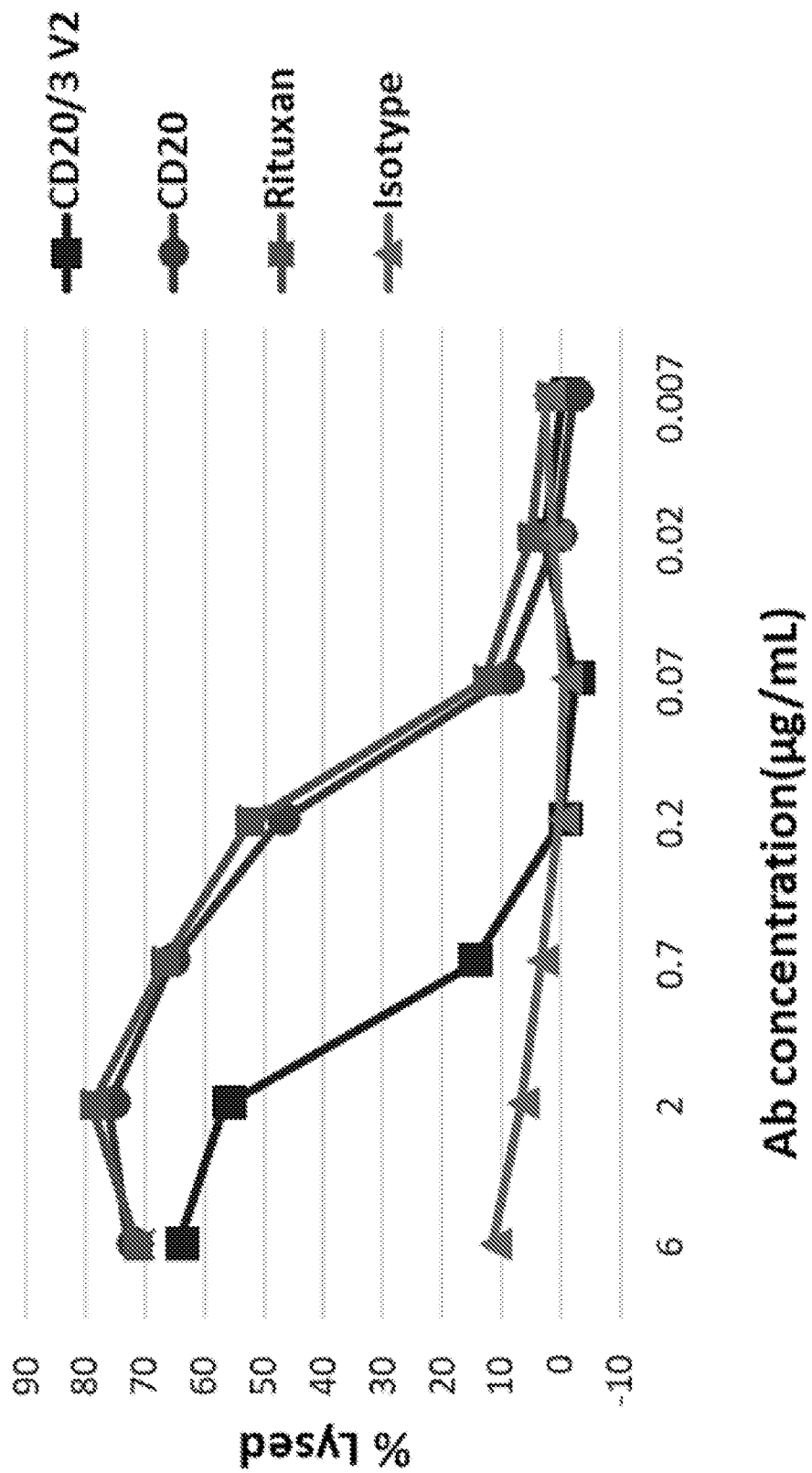
FIG. 14. Raji cell lysis mediated by CDC as determined by calcein release.

Since the CD20/CD3 BsMab has an arm binding to CD20 with a high affinity, experiments were performed to test whether the CD20-arm-binding is sufficient to induce complement dependent cytotoxicity. The antibodies were incubated with human complement enriched serum and CD20+ Raji cells. Imbalanced CD20/CD3 BsMab had reduced CDC efficacy compared to Rituximab and CD20 homodimer antibody. Detection results by FACS (7AAD) is shown in FIG. 13. Detection results by calcein release is shown in FIG. 14.

Example 8: Safety Evaluation

Figure 15:
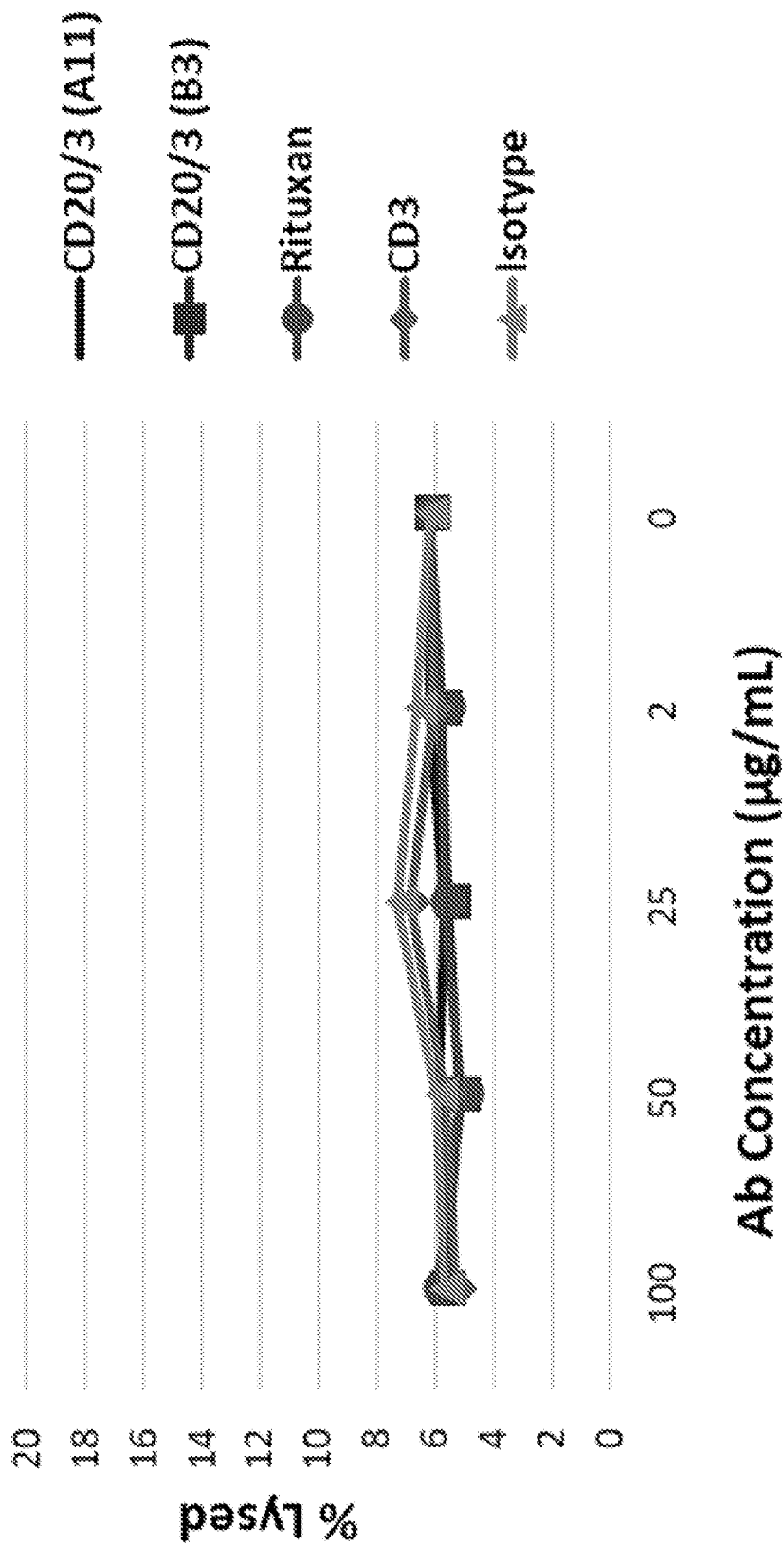
FIG. 15. Jurkat cell lysis mediated by CDC as determined by FACS (A11 and B3 are different elution fractions).

Whether CD3+ Jurkat cells and normal T cells can be killed by imbalanced CD20/CD3 BsMab was also tested. FIG. 15 showed that high dose of imbalanced CD20/CD3 BsMab did not induce CDC on Jurkat Cells.

Figure 16:
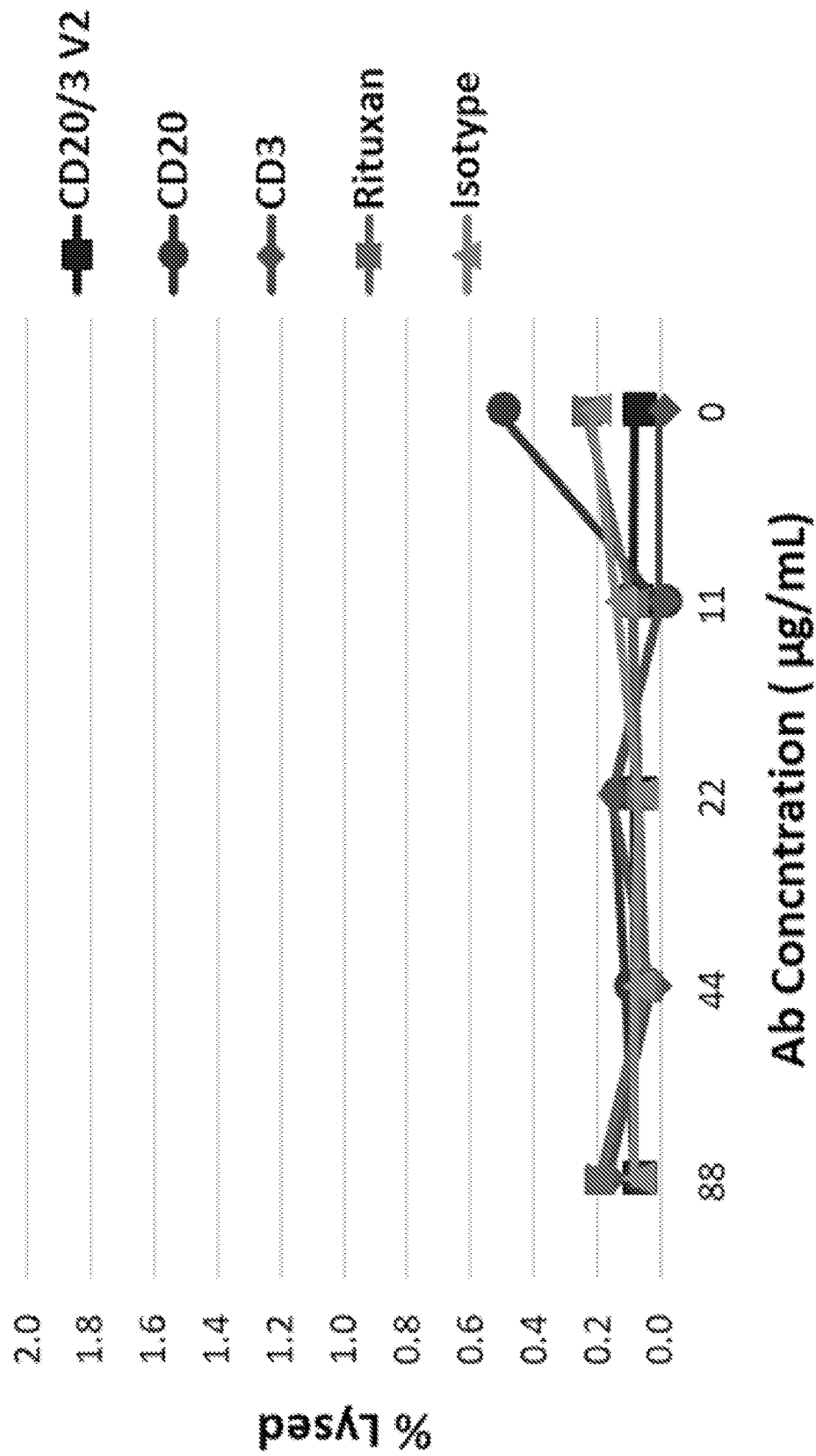
FIG. 16. T cell depletion in PBMC in the presence of human complement enriched serum.

FIG. 16 shows that imbalanced CD20/CD3 BsMab did not induce T cell death after co-Incubation with PBMC and human serum with human complement enriched serum.

Figure 17:
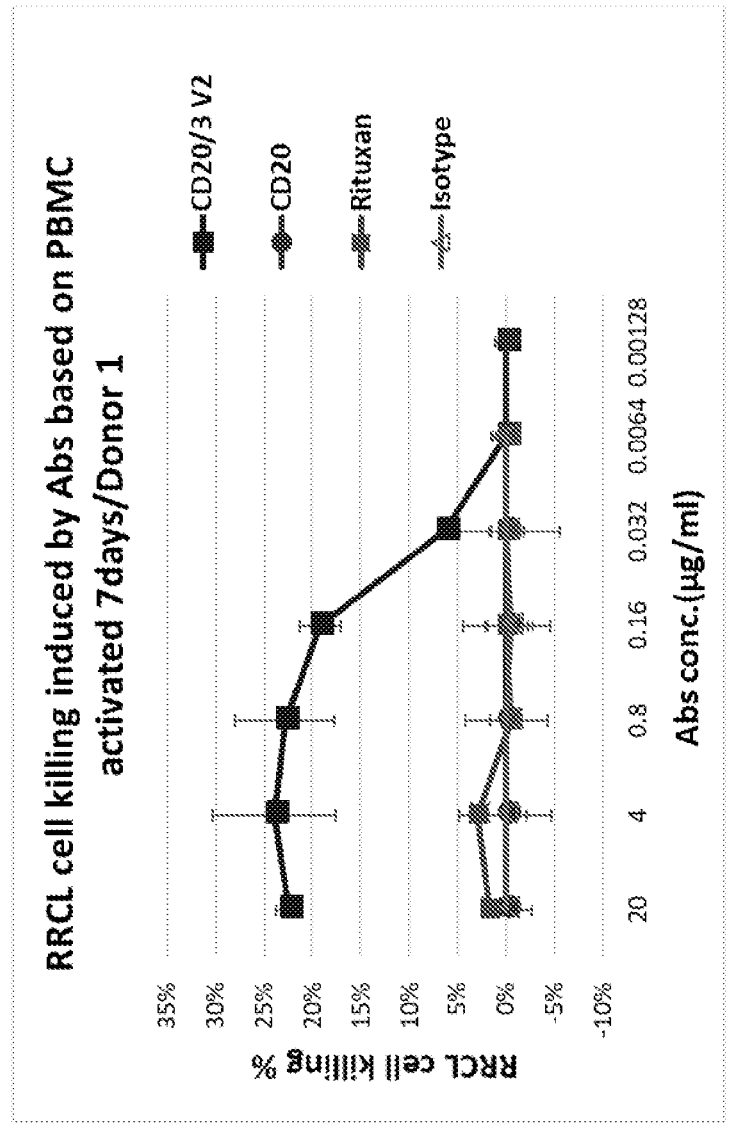
FIGS. 17-19. Rituximab-resistant cell lysis mediated by T cell activation based on PBMC from 3 different donors.
Figure 18:
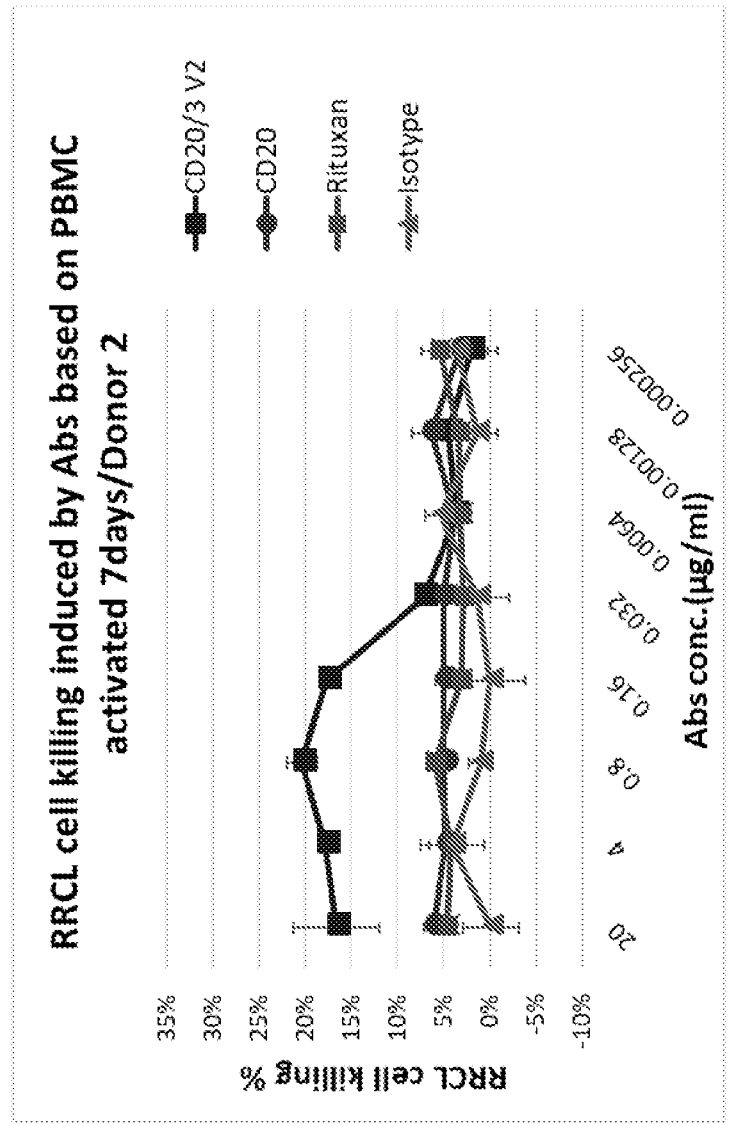
Figure 19:
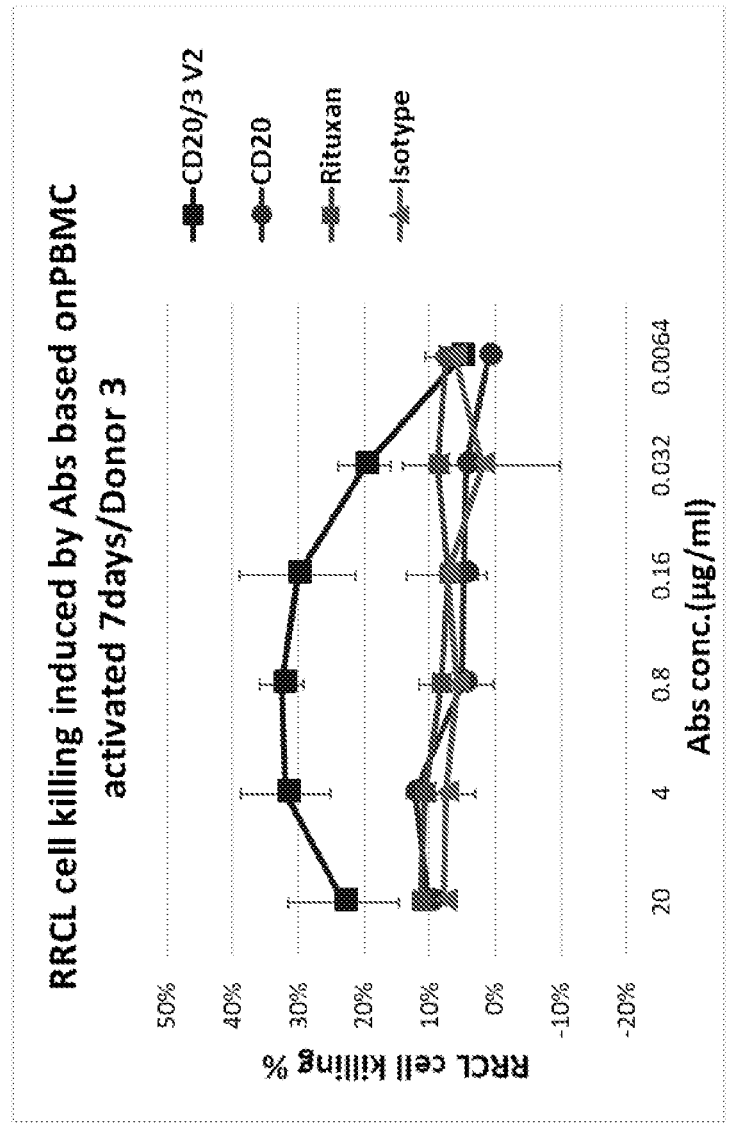

Example 9: Imbalanced CD20/CD3 BsMab can Kill Rituximab Resistant Raji Cells In order to test whether imbalanced CD20/CD3 BsMab can kill Rituximab resistant Raji cells (RRCL), RRCL with 7 day activated PBMCs from three different donors were incubated in the presence of antibodies as indicated in the figures, significant RRCL killing in the presence of imbalanced CD20/CD3 BsMab was observed (FIGS. 17-19).

Example 10: Animal Studies for Imbalanced CD20/CD3 BsMab

Experiments were performed to evaluate the effects of CD20/CD3 BsMab in animals.

Raji cells, human PBMC, and imbalanced CD20/CD3 BsMab were mixed and injected into mice through intravenous administration. These Raji cells were labeled by luciferase. Each mouse (B-NDG, Biocytogen, Beijing, Cat #201811808) in the treatment group received $5\times10^5$ Raji cells, $2.5\times10^6$ human PBMC cells, and 60 μg of antibodies. The mice were imaged to track the Raji cell depletion at day 0, day 2, day 3 and every three days after day 3.

At day 0, luciferase-labeled Raji cells and human PBMC cells were mixed with either phosphate-buffered saline PBS (G1 group; control; n=4), CD20/CD3 BsMab (G2 group; n=4), or Rituximab (anti-CD20 antibodies; G3 group; n=4). The mice were imaged for the first time 15 minutes post intravenous (i.v.) injection, and then were imaged at day 2, day 3 and every 3 days after day 3.

Figure 21A:
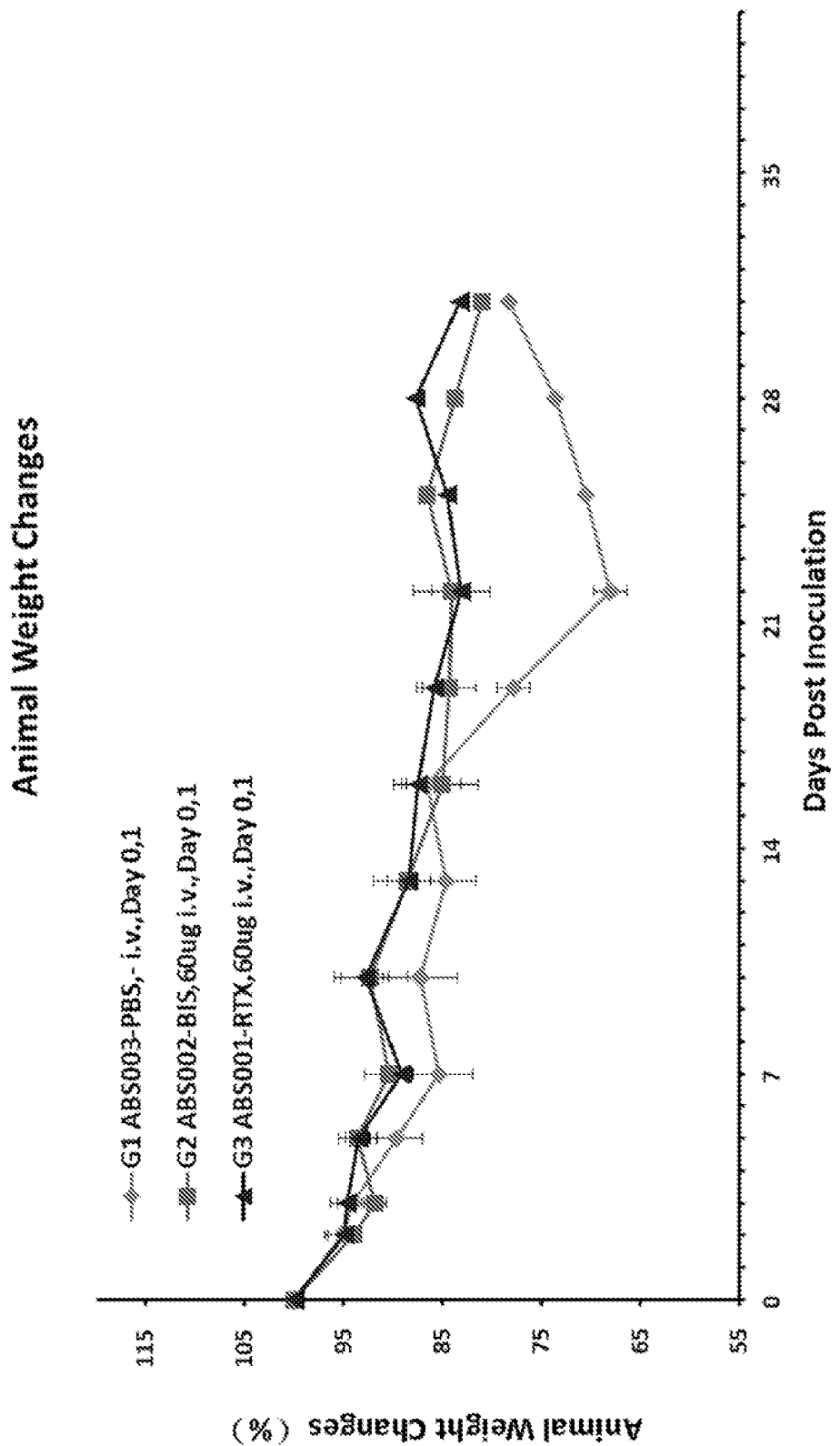
FIG. 21A. The average weight of mice in each group after being injected with phosphate-buffered saline PBS (G1), CD20/CD3 BsMab (G2; "BIS"), or Rituximab (G3; "RTX").
Figure 21B:
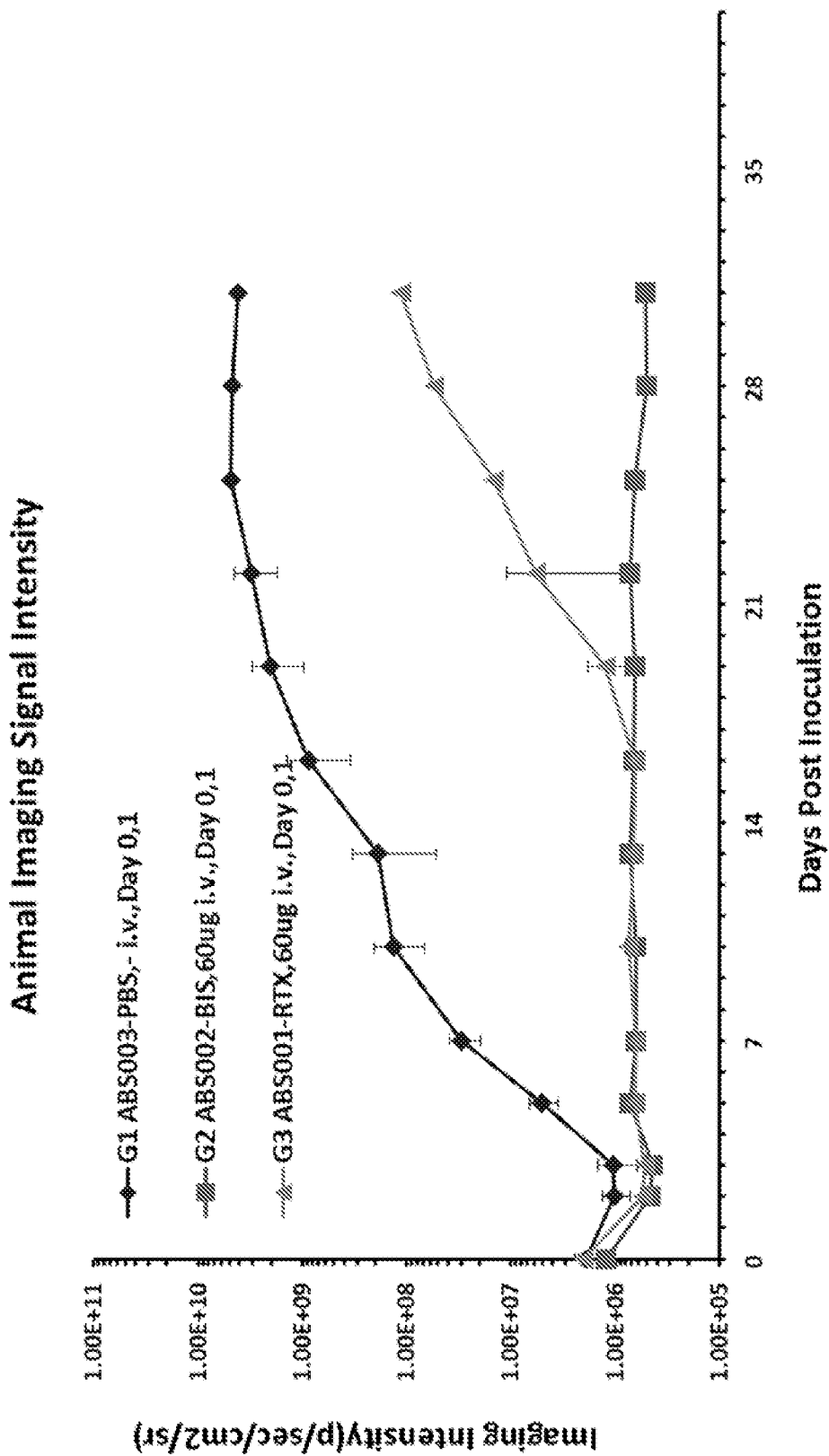
FIG. 21B. The average imaging intensity for luciferase-labeled Raji cells in each group after being injected with phosphate-buffered saline PBS (G1), CD20/CD3 BsMab (G2; "BIS"), or Rituximab (G3; "RTX").

FIG. 21A shows that the CD20/CD3 BsMab and Rituximab did not have obvious toxic effects. FIG. 21B shows that that both CD20/CD3 BsMab and Rituximab had tumor inhibitory effects, and Rituximab were not as effective as the CD20/CD3 BsMab. The difference in tumor inhibitory effects was observed starting from day 16 post injection.

Example 11: Characterization of Imbalanced Bispecific Antibodies

Experiments were performed to characterize the purified CD20/CD3 bispecific antibody sample.

Figure 22A:
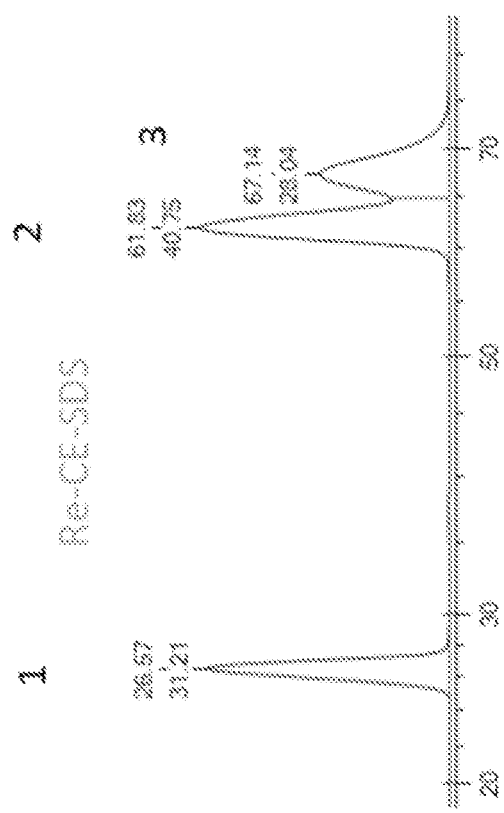
FIG. 22A. Reducing capillary electrophoresis sodium dodecyl sulfate (Re-CE-SDS) results for purified CD20/CD3 bispecific antibody samples.

First, reducing capillary electrophoresis sodium dodecyl sulfate (Re-CE-SDS) was performed for the purified CD20/CD3 bispecific antibody sample. The results showed there were three main peaks. Based on the molecular size, peak #1 was the common light chain (LC), peak #2 and #3 were the two different heavy chains (HC) (FIG. 22A).

Figure 22B:
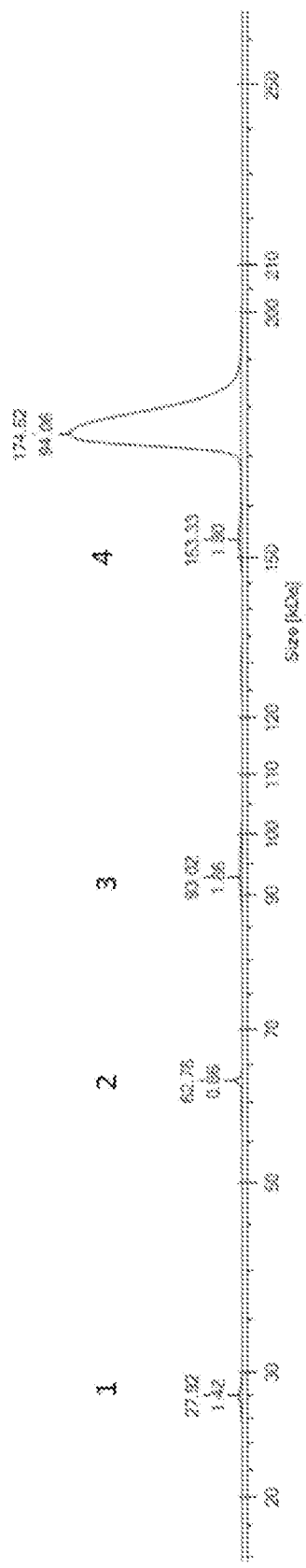
FIG. 22B. Non-reducing CE (Non-Re-CE-SDS) results for purified CD20/CD3 bispecific antibody samples.

Non-reducing CE (Non-Re-CE-SDS) was also performed. The results showed that there was one main peak for the CD20/CD3 bispecific IgG (FIG. 22B). The results in FIGS. 22A and 22B suggest the CD20/CD3 bispecific antibody sample has good purity.

Second, differential scanning fluorimetry (DSF) was performed to measure the protein melting temperature (Tm) and static light scattering (SLS) was performed to measure aggregation temperature at 266 nm (Tagg 266) and 473 nm (Tagg 473). The sample was submitted to the UNcle system for analysis. A temperature ramp of 1° C./min was performed with monitoring from 20° C. to 95° C. for DSF and SLS. UNcle measures SLS at 266 nm and 473 nm. Tm and Tagg were calculated and analyzed by using the UNcle Analysis Software.

Some testing antibodies have two Tms and some have three Tms. This is because that IgG is a multi-domain structure, CH2 domain usually has Tm of ~70° C. in PBS, and CH3 is more stable, its Tm is about 80° C. Fabs have Tm in a wide range, about 50-85° C., due to its large sequence variation. Therefore, The Tm value measured by various analytical techniques are usually "apparent" transition temperature rather than formal melting temperature. In case of antibody whole IgG, there are often 2-3 Tm values in DSF measurement. It is not easy to determine which Tm represents which domain.

In case of this bispecific antibody, it is likely that the 86.7° C. Tm represents CH3 domain only. The other lower 1 or 2 Tms represent Fab, CH2, or Fab+CH2.

As for Tagg, it is the temperature at which SLS starts to detect aggregation. Tagg266 measures SLS at 266 nm, which is more sensitive and suitable to detect smaller particles. Tagg473 measures at 473 nm, and better to detect larger particles.

Both DSF and SLS data show that the CD20/CD3 bispecific antibody has good thermostability.

TABLE 7

| | DSF | | | SLS | |
|---|---|---|---|---|---|
| | Tm D1 | Tm D2 | Tm D3 | Tagg266 | Tagg473 |
| Temperature | 66.0 | 80.1 | 86.7 | 70.9 | 71.2 |

Third, dynamic light scattering (DLS) only detected molecular particle of one size (10.15 nm). The results indicated that there was no aggregation in the sample.

TABLE 8

| DLS | Peak # | Mode Diameter (nm) | Mass (%) | PDI |
|---|---|---|---|---|
| 20° C. | Peak 1 | 10.15 | 100 | 0.177 |
| | Peak 2 | n.a. | | |
| | Peak 3 | n.a. | | |

These characterization data suggest that the CD20/CD3 bispecific antibody has good developability as a therapeutic antibody.

Example 12: Bispecific Antibodies that Bind to PD-L1 and CD55

Two versions bispecific antibodies were designed to bind to PD-L1 and CD55 (PD-L1/CD55 BsMab v1 and PD-L1/CD55 BsMab v2). These bispecific antibodies have two common light chains and two different heavy chains.

The sequences for the variable regions of the two heavy chains and the common light chain for the first version of bispecific antibody (PD-L1/CD55 BsMab v1) are shown below.

VHa for PD-L1 (Designed from Avelumab):

(SEQ ID NO: 4)
EVQLLESGGGLVEPGGSLRLSCAASGFTFSSYIMMWVRQAPGKGLEWVSS

IYPSGGITFYADTVKGRFTISRDNSKNTLYLQMNSLRAEDTAVYYCARIK

LGTVTTVDYWGEGTLVTVSS

VHb for CD55 (Designed from CD55 ScFV):

(SEQ ID NO: 5)
QVKLQESGGGLVKPGGSLKLSCAASGFTFSGYGMSWIRQTPGKRLEWVAT

INSGGSYTYYSDSVKGRFTISRDNVKNTLYLQMSSLKSEDTAMYYCARRN

GTLYYYLMDYWGRGTLVTVSS

Common VL (Designed from CD55 ScFV):

(SEQ ID NO: 6)
QSALTQPASVSGSPGQSITISCTGTSSDVGGYNYVSWYQQHPGKAPKLMI

YDVSKRPSGVSNRFSGSKSGNTASLTISGLQAEDEADYYCSSYTSASTRI

FGGGTKVTVLR

The CD55 ScFV is described e.g., in Identification of a human anti-CD55 single-chain Fv by subtractive panning of a phage library using tumor and nontumor cell lines, *Cancer Res.* 59 (11), 2718-2723 (1999), which is incorporated herein by reference in its entirety. The sequences for the parental antibodies are also shown below for comparison purpose:

Parental PD-L1 VH:

(SEQ ID NO: 12)
EVQLLESGGGLVQPGGSLRLSCAASGFTFSSYIMMWVRQAPGKGLEWVSS

IYPSGGITFYADTVKGRFTISRDNSKNTLYLQMNSLRAEDTAVYYCARIK

LGTVTTVDYWGQGTLVTVSS

Parental PD-L1 VL:

(SEQ ID NO: 13)
QSALTQPASVSGSPGQSITISCTGTSSDVGGYNYVSWYQQHPGKAPKLMI

YDVSNRPSGVSNRFSGSKSGNTASLTISGLQAEDEADYYCSSYTSSSTRV

FGTGTKVTVL

Parental CD55 VH:

(SEQ ID NO: 14)
QVKLQESGGGLVQPGGSLKLSCAASGFTFSGYGMSWIRQTPDKRLEWVAT

INSGGSYTYYSDSVKGRFTISRDNVKNTLYLQMSSLKSEDTAMYYCARRN

GTLYYYLMDYWGRGTLVTVSS

Parental CD55 VL:

(SEQ ID NO: 15)
QSVLTQPPSASGSPGQSVTISCTGTSSDVGGYNYVSWYQQHPGKAPKFMI

YDVSKRPSGVSNRFSGSKSGNTASLTISGVQAEDEADYYCSSYTSASTVI

FGGGTKLTVL

3D PI for Avelumab Fv (VH+VL) is 9.4, and 3D PI for anti-CD55 Fv is 9.8. After redesigning the sequences, 3D PI for VHa+common VL is 9.9, and 3D PI for VHb+common VL is 9.3. The mutations for the two VH chains are shown in the tables below.

TABLE 9

| Modified amino acids in VH (PD-L1) | | |
|---|---|---|
| Kabat numbering | Amino acid in parental | Amino acid after the modification |
| 13 | Q | E |
| 105 | Q | E |

TABLE 10

| Modified amino acids in VH (CD55) | | |
|---|---|---|
| Kabat numbering | Amino acid in parental | Amino acid after the modification |
| 13 | Q | K |
| 42 | D | G |

Example 13: Binding Affinities for the Newly Designed PD-L1 and CD55 Antibodies Experiments were performed to determine the binding affinities for the newly designed PD-L1 and CD55 antibodies.

Figures 23A, 23B:
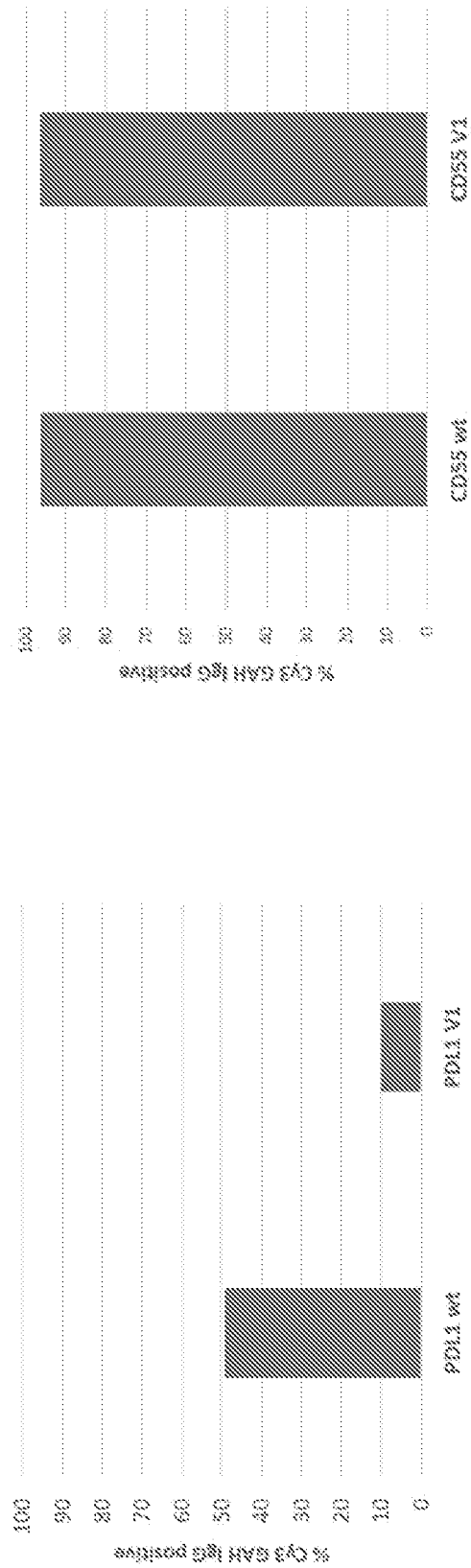
FIG. 23A. Binding affinities for Avelumab (PD-L1 wt) and the designed PD-L1 mono-dimer IgG antibodies (PD-L1 V1) comprising VHa for PD-L1 (SEQ ID NO: 4) and Common VL (SEQ ID NO: 6).
FIG. 23B. Binding affinities for the parental anti-CD55 antibody (CD55 wt) and the designed CD55 mono-dimer IgG antibodies (CD55 V1) comprising VHb for CD55 (SEQ ID NO: 5) and Common VL (SEQ ID NO: 6).

Anti-PD-L1 homodimer IgG (PD-L1 v1) containing the designed VH sequence (SEQ ID NO: 4) and the common VL sequence (SEQ ID NO: 6) had weaker binding affinity than the parental anti-PD-L1 antibody (PD-L1 wt) (FIG. 23A). Anti-CD55 homodimer IgG (CD55 v1) containing the designed VH sequence (SEQ ID NO: 5) and the common VL sequence (SEQ ID NO: 6) had similar binding affinity as compared to the parental anti-CD55 antibody (CD55 wt) (FIG. 23B).

Because the bispecific antibody should bind to the cancer specific antigen (PD-L1) with high affinity, and the other arm of the bispecific antibody should bind to the cancer-associated antigen (CD55) with low affinity, the antibodies (CD55 v1 and PD-L1 v1) did not satisfy this requirement.

Thus, a second version of the bispecific antibody was designed to bind to PD-L1 and CD55 (PD-L1/CD55 BsMab v2). The VHa and the VHb for the second version of the bispecific antibody are identical to the VHa and the VHb of the first version of the bispecific antibody. However, the common light chain was redesigned based on the methods described herein. The sequence for the redesigned common light chain is shown below:

Common VL2 (Re-Designed from SEQ ID NO: 6):

(SEQ ID NO: 7)
QSALTQPASVSGSPGQSITISCTGTSSDVGGYNYVSWYQQHPGKAPKLMI

YDVSNRPSGVSNRFSGSKSGNTASLTISGLQAEDEADYYCSSYTSSSTRI

FGGGTKVTVLR

The alignment for Common VL (SEQ IN NO: 6) and Common VL2 (SEQ ID NO: 7) is shown in FIG. 24. The underlined sequence is the sequence of light chain constant region.

The CDR sequences these redesigned VH and VL are shown below:

TABLE 11

VHa for PD-L1 heavy chain

| | CDR-H1 | CDR-H2 | CDR-H3 |
|---|---|---|---|
| Kabat | SYIMM (SEQ ID NO: 41) | SIYPSGGITFYADTVKG (SEQ ID NO: 42) | IKLGTVTTVDY (SEQ ID NO: 43) |
| Chothia | GFTFSSY (SEQ ID NO: 44) | YPSGGI (SEQ ID NO: 45) | IKLGTVTTVDY (SEQ ID NO: 46) |

TABLE 12

VHb for CD55 heavy chain

| | CDR-H1 | CDR-H2 | CDR-H3 |
|---|---|---|---|
| Kabat | GYGMS (SEQ ID NO: 47) | TINSGGSYTYYSDSVKG (SEQ ID NO: 48) | RNGTLYYYLMDY (SEQ ID NO: 49) |
| Chothia | GFTFSGY (SEQ ID NO: 50) | NSGGSY (SEQ ID NO: 51) | RNGTLYYYLMDY (SEQ ID NO: 52) |

TABLE 13

VL version 1 for the common VL

| | CDR-L1 | CDR-L2 | CDR-L3 |
|---|---|---|---|
| Kabat | TGTSSDVGGYNYVS (SEQ ID NO: 53) | DVSKRPS (SEQ ID NO: 54) | SSYTSASTRI (SEQ ID NO: 55) |
| Chothia | TGTSSDVGGYNYVS (SEQ ID NO: 56) | DVSKRPS (SEQ ID NO: 57) | SSYTSASTRI (SEQ ID NO: 58) |

TABLE 14

VL version 2 for the common VL

| | CDR-L1 | CDR-L2 | CDR-L3 |
|---|---|---|---|
| Kabat | TGTSSDVGGYNYVS (SEQ ID NO: 59) | DVSNRPS (SEQ ID NO: 60) | SSYTSSSTRI (SEQ ID NO: 61) |
| Chothia | TGTSSDVGGYNYVS (SEQ ID NO: 62) | DVSNRPS (SEQ ID NO: 63) | SSYTSSSTRI (SEQ ID NO: 64) |

Furthermore, because lambda light chains are less common as compared to kappa light chains in human serum, the constant region of the lambda light chain was replaced by the constant region of the kappa light chain in the examples.

Figures 25A, 25B:
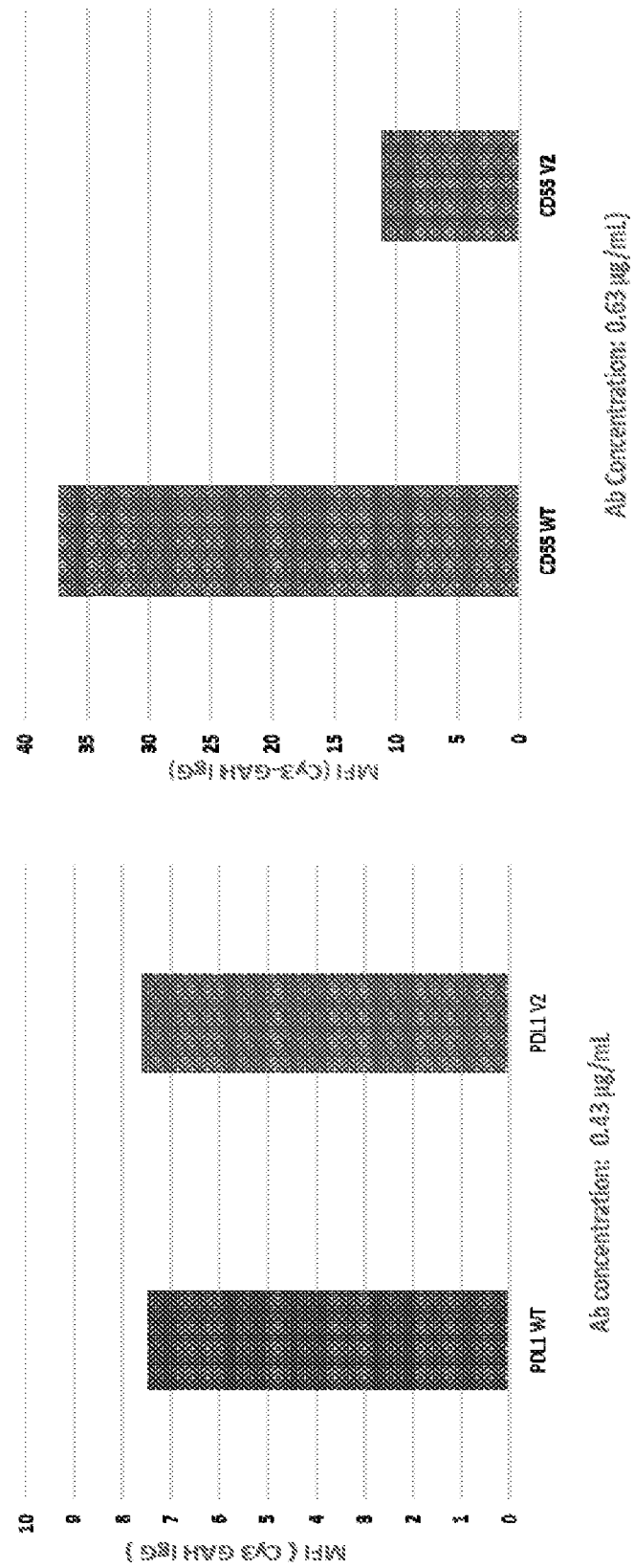
FIG. 25A. Binding affinities for Avelumab (PD-L1 wt) and the redesigned PD-L1 mono-dimer IgG antibodies (PD-L1 V2) comprising VHa for PD-L1 (SEQ ID NO: 4) and Common VL v2 (SEQ ID NO: 7).
FIG. 25B. Binding affinities for the parental anti-CD55 antibody (CD55 wt) and the redesigned CD55 mono-dimer IgG antibodies (CD55 V2) comprising VHb for CD55 (SEQ ID NO: 5) and Common VL v2 (SEQ ID NO: 7).

Experiments were performed to determine the binding affinities for the second version of antibodies. Anti-PD-L1 homodimer IgG (PD-L1 v2) containing the designed VH sequence (SEQ ID NO: 4) and the common VL2 sequence (SEQ ID NO: 7) had similar binding affinity as compared to the parental anti-PD-L1 antibody (PD-L1 wt) (FIG. 25A). Anti-CD55 homodimer IgG (CD55 v2) containing the designed VH sequence (SEQ ID NO: 5) and the common VL2 sequence (SEQ ID NO: 7) had weaker binding affinity as compared to the parental anti-CD55 antibody (CD55 wt) (FIG. 25B). Thus, the binding affinities for antibodies with the re-designed sequences meet the requirements, and PD-L1/CD55 BsMab v2 was selected for further experiments. The PD-L1/CD55 BsMab v2 has two common light chains (kappa chain) comprising SEQ ID NO: 7, one IgG1 heavy chain comprising SEQ ID NO: 4 and one IgG1 heavy chain comprising SEQ ID NO: 5. Furthermore, the heavy chain for PD-L1 has Y407T mutation (EU numbering), and the IgG1 heavy chain for CD55 has a T366Y (EU numbering) mutation.

The full-length sequence of the heavy chain and the light chain are shown below:

Full Length for PD-L1 Heavy Chain:

(SEQ ID NO: 65)
EVQLLESGGGLVEPGGSLRLSCAASGFTFSSYIMMWVRQAPGKGLEWVSS

IYPSGGITFYADTVKGRFTISRDNSKNTLYLQMNSLRAEDTAVYYCARIK

LGTVTTVDYWGEGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSREEMTKNQVSLYCLVKGFYPSDIAVEWESNGQPENNYKTTPPV

LDSDGSFFLYSKLTVDKSRWQQGNVFSCSVMHEALHNHYTQKSLSLSPGK

Full Length for CD55 Heavy Chain:

(SEQ ID NO: 66)
QVKLQESGGGLVKPGGSLKLSCAASGFTFSGYGMSWIRQTPGKRLEWVAT

INSGGSYTYYSDSVKGRFTISRDNVKNTLYLQMSSLKSEDTAMYYCARRN

GTLYYYLMDYWGRGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPP

VLDSDGSFFLTSKLTVDKSRWQQGNVFSCSVMHEALHNHYTQKSLSLSPG

K

Full Length for CD55 Common Light Chain Version 1:

(SEQ ID NO: 67)
QSALTQPASVSGSPGQSITISCTGTSSDVGGYNYVSWYQQHPGKAPKLMI

YDVSKRPSGVSNRFSGSKSGNTASLTISGLQAEDEADYYCSSYTSASTRI

FGGGTKVTVLRTVAAPSVFIFPPSDEQLKSGTASVVCLLNNFYPREAKVQ

WKVDNALQSGNSQESVTEQDSKDSTYSLSSTLTLSKADYEKHKVYACEVT

HQGLSSPVTKSFNRGEC

Full Length for CD55 Common Light Chain Version 2:

(SEQ ID NO: 68)
QSALTQPASVSGSPGQSITISCTGTSSDVGGYNYVSWYQQHPGKAPKLMI

YDVSNRPSGVSNRFSGSKSGNTASLTISGLQAEDEADYYCSSYTSSSTRI

FGGGTKVTVLRTVAAPSVFIFPPSDEQLKSGTASVVCLLNNFYPREAKVQ

WKVDNALQSGNSQESVTEQDSKDSTYSLSSTLTLSKADYEKHKVYACEVT

HQGLSSPVTKSFNRGEC

Furthermore, the pI for the antibodies described herein have also been determined. This information can be useful to select appropriate pH for elution.

TABLE 15

|  | PI |
| --- | --- |
| PDL1/CD55 BsAb version 1 | 8.64 |
| PDL1 homodimer version 1 | 8.36 |
| CD55 homodimer version 1 | 8.83 |
| PDL1/CD55 BsAb version 2 | 8.57 |
| PDL1 homodimer version 2 | 8.24 |
| CD55 homodimer version 2 | 8.78 |
| PDL1 parental Ab | 8.36 |
| CD55 parental Ab | 8.6 |

Figure 26A:
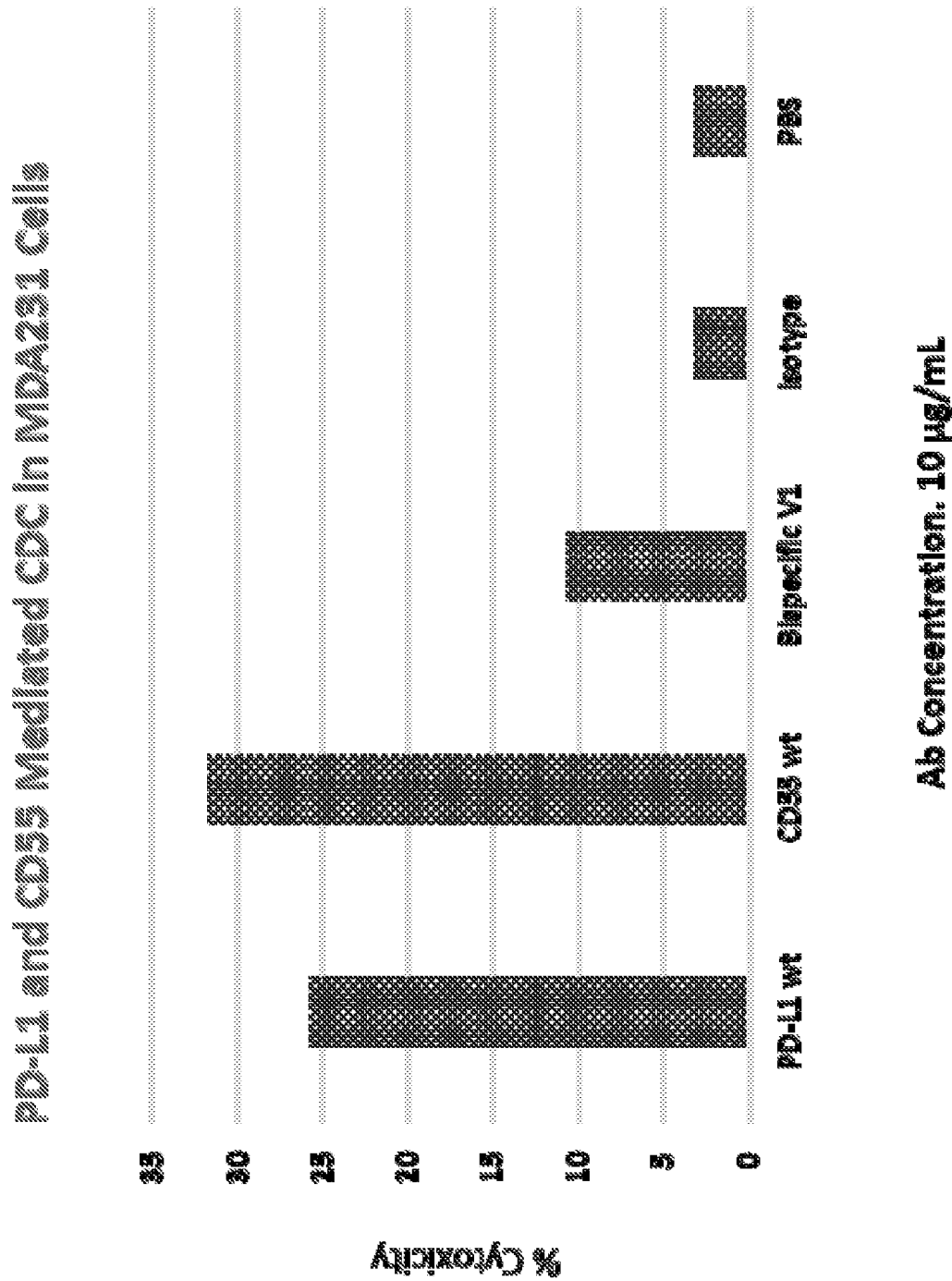
FIGS. 26A-26B. Antibodies mediated CDC in MDA231 cells.
Figure 26B:
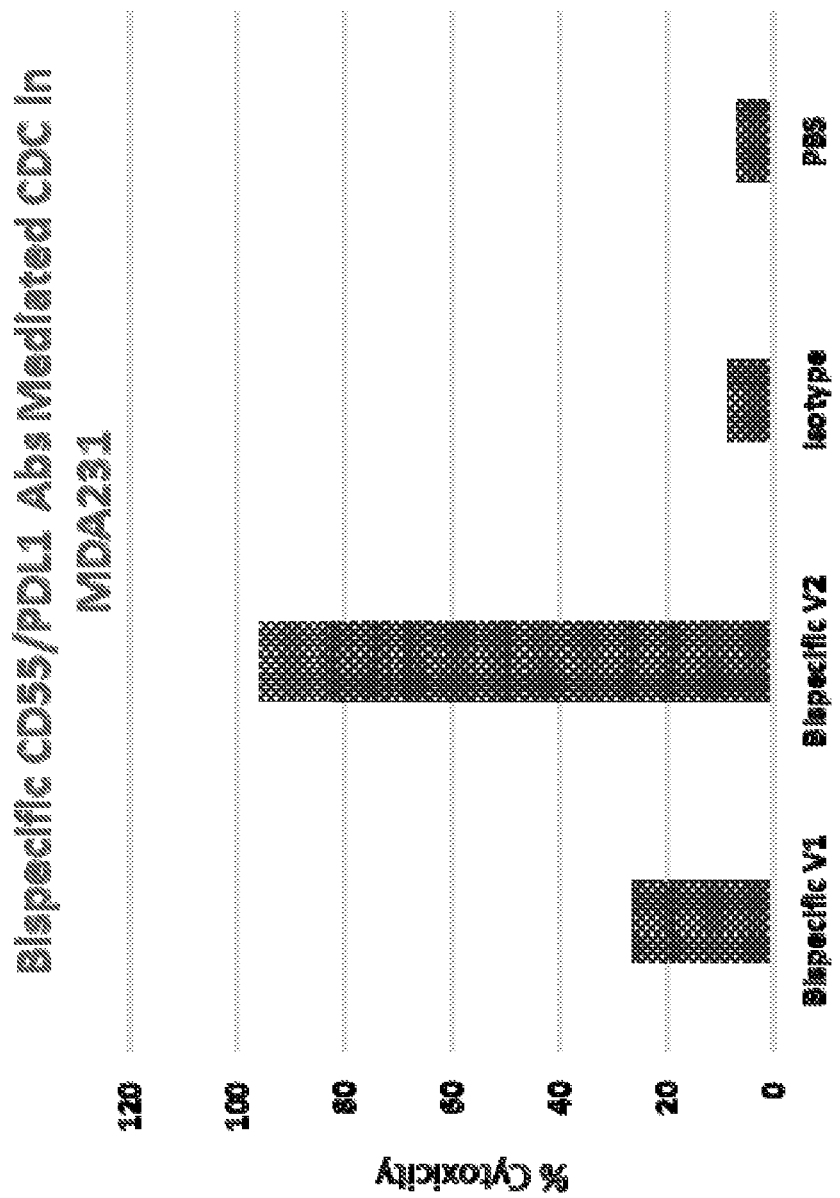

Example 14: Complement Dependent Cytotoxicity (CDC) for PD-L1/CD55 Bispecific Antibodies Experiments were performed to test complement dependent cytotoxicity for the PD-L1/CD55 bispecific antibodies. Their parental antibodies were included for comparison purposes. The assays were performed on MDA231 cells based on the protocol described herein, and the concentration for each antibody was at 10 ug/ml. The results were shown in FIGS. 26A-26B.

As shown in the figures, both anti-PD-L1 (PD-L1 wt) and anti-CD55 (CD55 wt) parental antibodies can induce CDC. PD-L1/CD55 bispecific antibody v1 had much lower CDC as compared to the parental anti-PD-L1 antibody (PD-L1 wt) and the parental anti-CD55 antibody (CD55 wt). In contrast, PD-L1/CD55 bispecific antibody v2 had much higher CDC than the first version, the parental anti-PD-L1 antibody (PD-L1 wt) and the parental anti-CD55 antibody (CD55 wt). The CDC effect of PD-L1/CD55 bispecific antibody v2 was about 4.5 folds higher than the CDC efficacy of the first version of bispecific antibody.

Example 15: Internalization Induced by PD-L1/CD55 Bispecific Antibodies

Experiments were performed to assess internalization induced by PD-L1/CD55 bispecific antibodies.

Figure 27A:
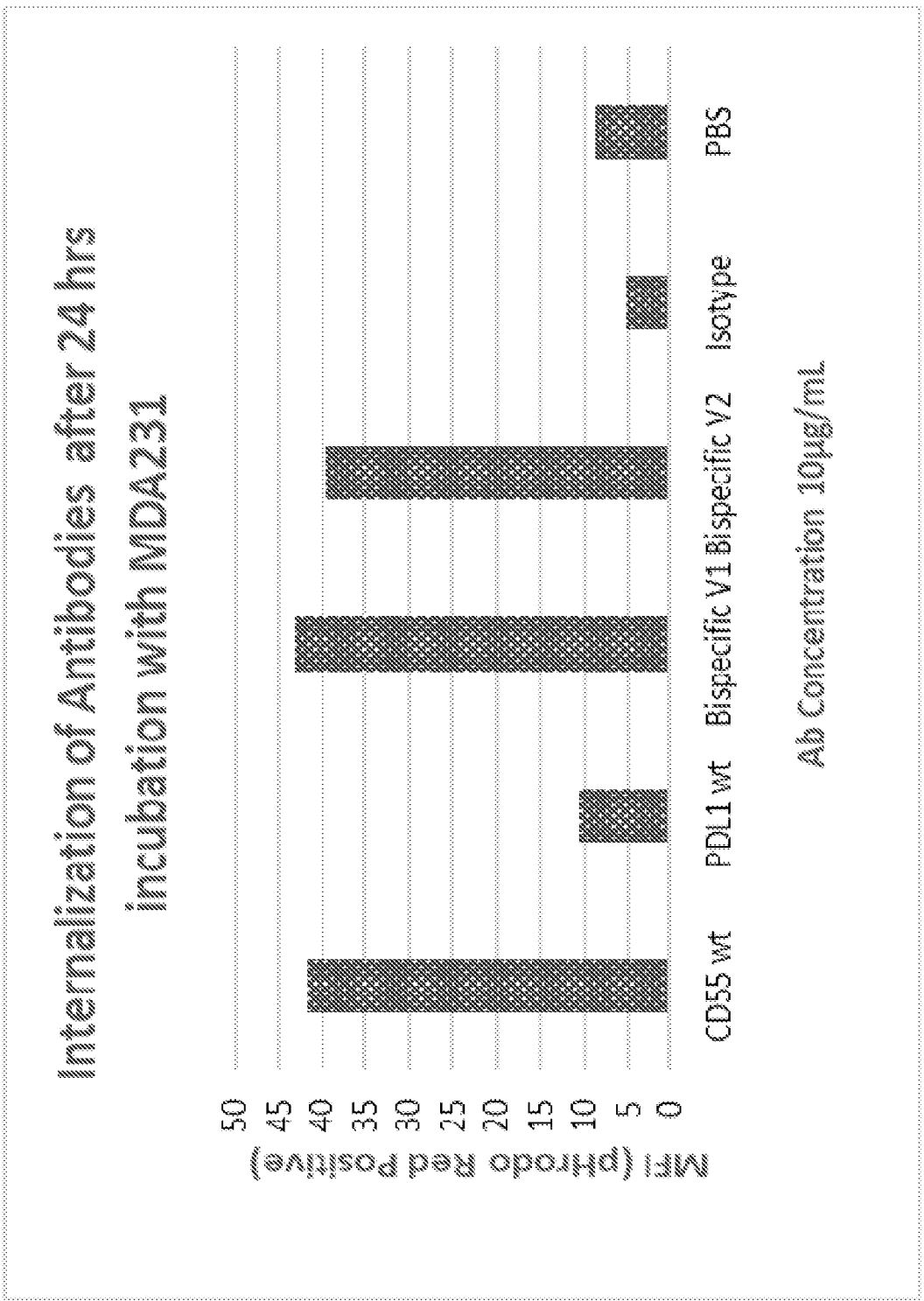
FIG. 27A. Antibody internalization assay results with MDA231 cells.
Figure 27B:
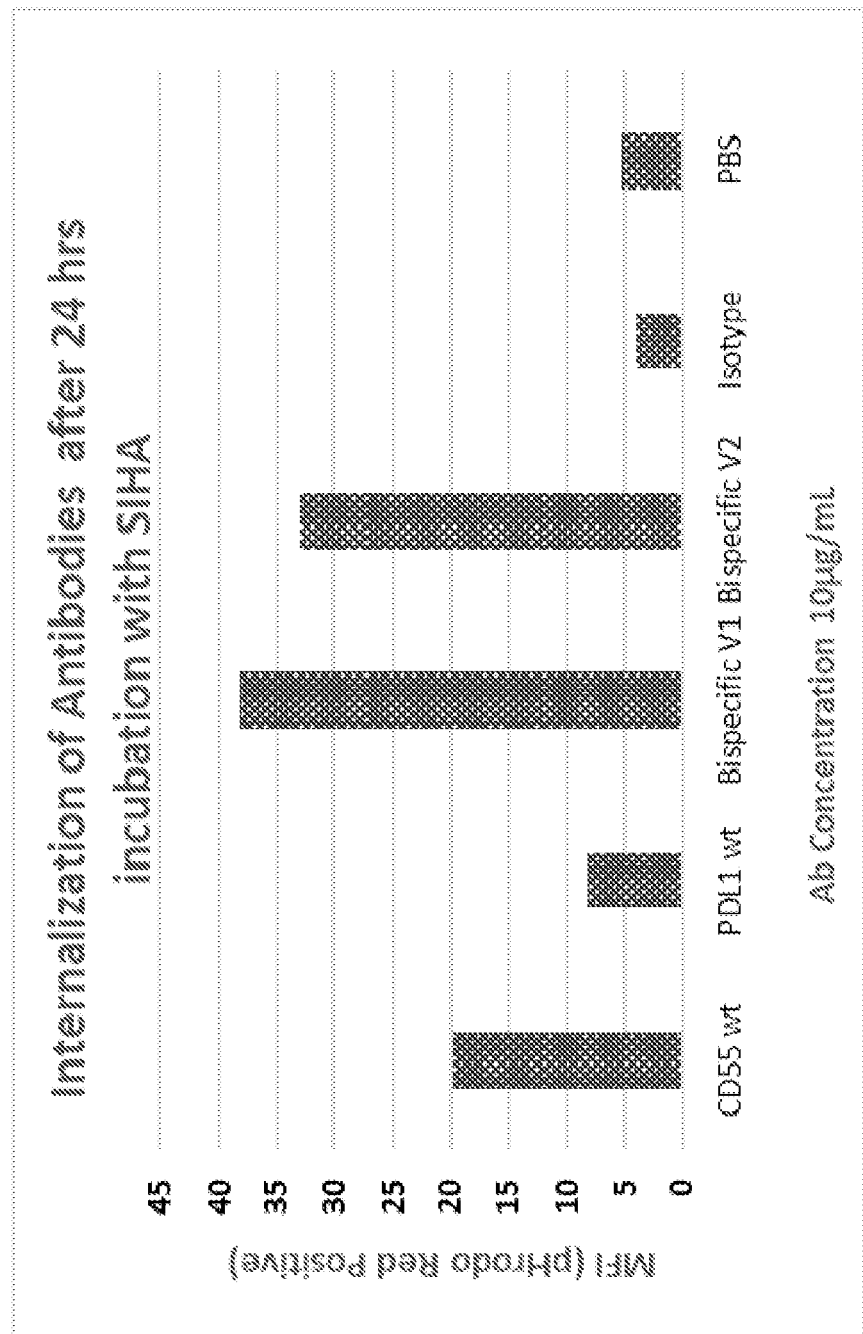
FIG. 27B. Antibody internalization assay results with SIHA cells.

Internalization assays were performed the two versions of PD-L1/CD55 bispecific antibodies and their parental antibodies. MDA231 cells were used in the first internalization experiment (FIG. 27A) and SIHA cells were used in the second internalization experiment (FIG. 27B). Cells were mixed with 20 ug/ml antibodies, and incubated at 37° C. for 30 minutes. Then pHrodo-labeled secondary antibody was added and incubated with the cells at 37° C. for 24 hours. Cells were then harvested and analyzed on FACS.

CD55 is a receptor for Echoviruses and coxsackie B viruses infection, which is known to be a receptor with internalization ability. Therefore, the anti-CD55 parental monoclonal antibody (CD55 wt) can trigger fast internalization of CD55. As shown in FIG. 27A, in MDA231 cells which have similar PD-L1 and CD55 expression level, the internalization triggered by the anti-PD-L1 antibody was much slower than that of CD55. However, both PD-L1/CD55 bispecific antibody v1 and v2 can induce internalization, and the internalization rate was comparable to that of the anti-CD55 parental monoclonal antibody.

In FIG. 27B, the CD55 expression is higher than PD-L1 in SIHA cells. Both PD-L1/CD55 bispecific antibodies v1 and v2 can induce better internalization than the parental anti-PD-L1 antibody and the parental anti-CD55 antibody. Nevertheless, given the reduced binding of PD-L1/CD55 BsMab v2 to CD55 as compared to that of v1, the PD-L1/CD55 BsMab v2 should have better efficacy/safety balance in vivo, and should be safer than PD-L1/CD55 BsMab v1. Thus, it is expected that PD-L1/CD55 BsMab can induce target cancer cell death at three different levels: (1) block PD1/PD-L1 interaction; (2) induce PD-L1 internalization; 3) When conjugated to a drug, the antibody drug conjugate can kill the cancer cell.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A bispecific antibody or antigen-binding fragment thereof comprising a first heavy chain variable region (VH1),
a second heavy chain variable region (VH2),
a first light chain variable region (VL1), and
a second light chain variable region (VL2),
wherein the first heavy chain variable region and the first light chain variable region associate with each other, forming a first antigen binding region that specifically binds to a first antigen, and
the second heavy chain variable region and the second light chain variable region associate with each other, forming a second antigen binding region that specifically binds to a second antigen,
wherein the first antigen is PD-L1, and the second antigen is CD55, and (1) the VH1 comprises complementarity determining regions (CDRs) 1, 2, and 3, wherein VH1 CDR1 comprises the amino acid sequence of SEQ ID NO: 41, the VH1 CDR2 comprises the amino acid sequence of SEQ ID NO: 42, and the VH1 CDR3 comprises the amino acid sequence of SEQ ID NO: 43;
the VH2 comprises CDRs 1, 2, and 3, wherein VH2 CDR1 comprises the amino acid sequence of SEQ ID NO: 47, the VH2 CDR2 comprises the amino acid sequence of SEQ ID NO: 48, and the VH2 CDR3 comprises the amino acid sequence of SEQ ID NO: 49;
the VL1 comprises CDRs 1, 2, and 3, wherein VL1 CDR1 comprises the amino acid sequence of SEQ ID NO: 53, the VL1 CDR2 comprises the amino acid sequence of SEQ ID NO: 54, and the VL1 CDR3 comprises the amino acid sequence of SEO ID NO: 55; and
the VL2 comprises CDRs 1, 2, and 3, wherein VL2 CDR1 comprises the amino acid sequence of SEQ ID NO: 53, the VL2 CDR2 comprises the amino acid sequence of SEQ ID NO: 54, and the VL2 CDR3 comprises the amino acid sequence of SEQ ID NO: 55;

(2) the VH1 comprises CDRs 1, 2, and 3, wherein VH1 CDR1 comprises the amino acid sequence of SEQ ID NO: 41, the VH1 CDR2 comprises the amino acid sequence of SEQ ID NO: 42, and the VH1 CDR3 comprises the amino acid sequence of SEQ ID NO: 43;
the VH2 comprises CDRs 1, 2, and 3, wherein VH2 CDR1 comprises the amino acid sequence of SEQ ID NO: 47, the VH2 CDR2 comprises the amino acid sequence of SEQ ID NO: 48, and the VH2 CDR3 comprises the amino acid sequence of SEQ ID NO: 49;
the VL1 comprises CDRs 1, 2, and 3, wherein VL1 CDR1 comprises the amino acid sequence of SEQ ID NO: 59, the VL1 CDR2 comprises the amino acid sequence of SEQ ID NO: 60, and the VL1 CDR3 comprises the amino acid sequence of SEQ ID NO: 61; and the VL2 comprises CDRs 1, 2, and 3, wherein VL2 CDR1 comprises the amino acid sequence of SEQ ID NO: 59, the VL2 CDR2 comprises the amino acid sequence of SEQ ID NO: 60, and the VL2 CDR3 comprises the amino acid sequence of SEQ ID NO: 61;

(3) the VH1 comprises CDRs 1, 2, and 3, wherein VH1 CDR1 comprises the amino acid sequence of SEQ ID NO: 44, the VH1 CDR2 comprises the amino acid sequence of SEQ ID NO: 45, and the VH1 CDR3 comprises the amino acid sequence of SEQ ID NO: 46;

the VH2 comprises CDRs 1, 2, and 3, wherein VH2 CDR1 comprises the amino acid sequence of SEQ ID NO: 50, the VH2 CDR2 comprises the amino acid sequence of SEQ ID NO: 51, and the VH2 CDR3 comprises the amino acid sequence of SEQ ID NO: 52;

the VL1 comprises CDRs 1, 2, and 3, wherein VL1 CDR1 comprises the amino acid sequence of SEQ ID NO: 56, the VL1 CDR2 comprises the amino acid sequence of SEQ ID NO: 57, and the VL1 CDR3 comprises the amino acid sequence of SEQ ID NO: 58; and the VL2 comprises CDRs 1, 2, and 3, wherein VL2 CDR1 comprises the amino acid sequence of SEQ ID NO: 56, the VL2 CDR2 comprises the amino acid sequence of SEQ ID NO: 57, and the VL2 CDR3 comprises the amino acid sequence of SEQ ID NO: 58; or (4) the VH1 comprises CDRs 1, 2, and 3, wherein VH1 CDR1 comprises the amino acid sequence of SEQ ID NO: 44, the VH1 CDR2 comprises the amino acid sequence of SEQ ID NO: 45, and the VH1 CDR3 comprises the amino acid sequence of SEQ ID NO: 46;

the VH2 comprises CDRs 1, 2, and 3, wherein VH2 CDR1 comprises the amino acid sequence of SEQ ID NO: 50, the VH2 CDR2 comprises the amino acid sequence of SEQ ID NO: 51, and the VH2 CDR3 comprises the amino acid sequence of SEQ ID NO: 52;

the VL1 comprises CDRs 1, 2, and 3, wherein VL1 CDR1 comprises the amino acid sequence of SEQ ID NO: 59, the VL1 CDR2 comprises the amino acid sequence of SEQ ID NO: 60, and the VL1 CDR3 comprises the amino acid sequence of SEQ ID NO: 61; and the VL2 comprises CDRs 1, 2, and 3, wherein VL2 CDR1 comprises the amino acid sequence of SEQ ID NO: 59, the VL2 CDR2 comprises the amino acid sequence of SEQ ID NO: 60, and the VL2 CDR3 comprises the amino acid sequence of SEQ ID NO: 61.

2. The bispecific antibody or the antigen-binding fragment thereof of claim 1, wherein the first antigen binding region specifically binds to the first antigen with a binding affinity greater than $10^8$ $M^{-1}$.

3. The bispecific antibody or the antigen-binding fragment thereof of claim 1, wherein the bispecific antibody or the antigen-binding fragment thereof comprises a first heavy chain comprising the first heavy chain variable region, and a second heavy chain comprising the second heavy chain variable region, wherein the first heavy chain and the second heavy chain associate with each other by the knobs into holes approach.

4. The bispecific antibody or the antigen-binding fragment thereof of claim 1, wherein the second antigen binding region specifically binds to the second antigen with a binding affinity less than $10^6$ $M^{-1}$.

5. The bispecific antibody or the antigen-binding fragment thereof of claim 1, wherein the binding affinity of the first antigen binding region when it binds to the first antigen is at least 100 times greater than the binding affinity of the second antigen binding region when it binds to the second antigen.

6. The bispecific antibody or the antigen-binding fragment thereof of claim 1, wherein the first heavy chain variable region (VH1) comprises an amino acid sequence that is at least 90% identical to SEQ ID NO: 4 or SEQ ID NO: 12;

the second heavy chain variable region (VH2) comprises an amino acid sequence that is at least 90% identical to SEQ ID NO: 5;

the first light chain variable region (VL1) comprises an amino acid sequence that is at least 90% identical to SEQ ID NO: 6; and the second light chain variable region (VL2) comprises an amino acid sequence that is at least 90% identical to SEQ ID NO: 6.

7. The bispecific antibody or the antigen-binding fragment thereof of claim 1, wherein the first heavy chain variable region (VH1) comprises an amino acid sequence that is at least 90% identical to SEQ ID NO: 4 or SEQ ID NO: 12;

the second heavy chain variable region (VH2) comprises an amino acid sequence that is at least 90% identical to SEQ ID NO: 5;

the first light chain variable region (VL1) comprises an amino acid sequence that is at least 90% identical to SEQ ID NO: 7; and the second light chain variable region (VL2) comprises an amino acid sequence that is at least 90% identical to SEQ ID NO: 7.

8. The bispecific antibody or the antigen-binding fragment thereof of claim 1, comprising: a first polypeptide comprising the VH1, a second polypeptide comprising the VH2, a third polypeptide comprising the VL1, and a fourth polypeptide comprising the VL2, wherein the first polypeptide comprises an amino acid sequence that is at least 90% identical to SEQ ID NO: 65;

the second polypeptide comprises an amino acid sequence that is at least 90% identical to SEQ ID NO: 66;

the third polypeptide comprises an amino acid sequence that is at least 90% identical to SEQ ID NO: 67; and the fourth polypeptide comprises an amino acid sequence that is at least 90% identical to SEQ ID NO: 67.

9. An antibody or an antigen-binding fragment thereof that binds to PD-L1 and CD55, comprising a first heavy chain variable region (VH1) comprising CDR1, CDR2, and CDR3, wherein the VH1 CDR1, VH1 CDR2, and VH1 CDR3 are identical to CDR1, CDR2, and CDR3 present in SEQ ID NO: 4 or 12, respectively;

a second heavy chain variable region (VH2) comprising CDR1, CDR2, and CDR3, wherein the VH2 CDR1, VH2 CDR2, and VH2 CDR3 are identical to CDR1, CDR2, and CDR3 present in SEQ ID NO: 5, respectively;

a first light chain variable region (VL1) comprising CDR1, CDR2, and CDR3, wherein the VL1 CDR1, VL1 CDR2, and VL1 CDR3 are identical to CDR1, CDR2, and CDR3 present in SEQ ID NO: 6 or 7, respectively; and a second light chain variable region (VL2) comprising CDR1, CDR2, and CDR3, wherein the VL2 CDR1, VL2 CDR2, and VL2 CDR3 are identical to CDR1, CDR2, and CDR3 present in SEQ ID NO: 6 or 7, respectively.

10. The antibody or the antigen-binding fragment thereof of claim 9, wherein the antibody or the antigen-binding fragment thereof is a bispecific antibody or antigen-binding fragment thereof.

11. The antibody or the antigen-binding fragment thereof of claim 9, wherein
the VH1 comprises the amino acid sequence of SEQ ID NO: 4 or 12;
the VH2 comprise the amino acid sequence of SEQ ID NO: 5;
the VL1 comprise the amino acid sequence of SEQ ID NO: 6; and
the VL2 comprises the amino acid sequence of SEQ ID NO: 6.

12. The bispecific antibody or the antigen-binding fragment thereof of claim 1, comprising: a first polypeptide comprising the VH1, a second polypeptide comprising the VH2, a third polypeptide comprising the VL1, and a fourth polypeptide comprising the VL2, wherein
the first polypeptide comprises an amino acid sequence that is at least 90% identical to SEQ ID NO: 65;
the second polypeptide comprises an amino acid sequence that is at least 90% identical to SEQ ID NO: 66;
the third polypeptide comprises an amino acid sequence that is at least 90% identical to SEQ ID NO: 68; and
the fourth polypeptide comprises an amino acid sequence that is at least 90% identical to SEQ ID NO: 68.

13. The bispecific antibody or the antigen-binding fragment thereof of claim 1, wherein the binding affinity of the first antigen binding region when it binds to the first antigen is at least 1000 times greater than the binding affinity of the second antigen binding region when it binds to the second antigen.

14. The bispecific antibody or the antigen-binding fragment thereof of claim 1, wherein the first light chain variable region and the second light chain variable region are identical.

15. The bispecific antibody or the antigen-binding fragment thereof of claim 1, wherein according to Kabat definition, the VH1 comprises complementarity determining regions (CDRs) 1, 2, and 3, wherein VH1 CDR1 comprises the amino acid sequence of SEQ ID NO: 41, the VH1 CDR2 comprises the amino acid sequence of SEQ ID NO: 42, and the VH1 CDR3 comprises the amino acid sequence of SEQ ID NO: 43;
the VH2 comprises CDRs 1, 2, and 3, wherein VH2 CDR1 comprises the amino acid sequence of SEQ ID NO: 47, the VH2 CDR2 comprises the amino acid sequence of SEQ ID NO: 48, and the VH2 CDR3 comprises the amino acid sequence of SEQ ID NO: 49;
the VL1 comprises CDRs 1, 2, and 3, wherein VL1 CDR1 comprises the amino acid sequence of SEQ ID NO: 53, the VL1 CDR2 comprises the amino acid sequence of SEQ ID NO: 54, and the VL1 CDR3 comprises the amino acid sequence of SEQ ID NO: 55; and
the VL2 comprises CDRs 1, 2, and 3, wherein VL2 CDR1 comprises the amino acid sequence of SEQ ID NO: 53, the VL2 CDR2 comprises the amino acid sequence of SEQ ID NO: 54, and the VL2 CDR3 comprises the amino acid sequence of SEQ ID NO: 55.

16. The bispecific antibody or the antigen-binding fragment thereof of claim 1, wherein according to Kabat definition, the VH1 comprises complementarity determining regions (CDRs) 1, 2, and 3, wherein VH1 CDR1 comprises the amino acid sequence of SEQ ID NO: 41, the VH1 CDR2 comprises the amino acid sequence of SEQ ID NO: 42, and the VH1 CDR3 comprises the amino acid sequence of SEQ ID NO: 43;
the VH2 comprises CDRs 1, 2, and 3, wherein VH2 CDR1 comprises the amino acid sequence of SEQ ID NO: 47, the VH2 CDR2 comprises the amino acid sequence of SEQ ID NO: 48, and the VH2 CDR3 comprises the amino acid sequence of SEQ ID NO: 49;
the VL1 comprises CDRs 1, 2, and 3, wherein VL1 CDR1 comprises the amino acid sequence of SEQ ID NO: 59, the VL1 CDR2 comprises the amino acid sequence of SEQ ID NO: 60, and the VL1 CDR3 comprises the amino acid sequence of SEQ ID NO: 61; and
the VL2 comprises CDRs 1, 2, and 3, wherein VL2 CDR1 comprises the amino acid sequence of SEQ ID NO: 59, the VL2 CDR2 comprises the amino acid sequence of SEQ ID NO: 60, and the VL2 CDR3 comprises the amino acid sequence of SEQ ID NO: 61.

17. The bispecific antibody or the antigen-binding fragment thereof of claim 1, wherein according to Chothia definition, the VH1 comprises complementarity determining regions (CDRs) 1, 2, and 3, wherein VH1 CDR1 comprises the amino acid sequence of SEQ ID NO: 44, the VH1 CDR2 comprises the amino acid sequence of SEQ ID NO: 45, and the VH1 CDR3 comprises the amino acid sequence of SEQ ID NO: 46;
the VH2 comprises CDRs 1, 2, and 3, wherein VH2 CDR1 comprises the amino acid sequence of SEQ ID NO: 50, the VH2 CDR2 comprises the amino acid sequence of SEQ ID NO: 51, and the VH2 CDR3 comprises the amino acid sequence of SEQ ID NO: 52;
the VL1 comprises CDRs 1, 2, and 3, wherein VL1 CDR1 comprises the amino acid sequence of SEQ ID NO: 56, the VL1 CDR2 comprises the amino acid sequence of SEQ ID NO: 57, and the VL1 CDR3 comprises the amino acid sequence of SEQ ID NO: 58; and
the VL2 comprises CDRs 1, 2, and 3, wherein VL2 CDR1 comprises the amino acid sequence of SEQ ID NO: 56, the VL2 CDR2 comprises the amino acid sequence of SEQ ID NO: 57, and the VL2 CDR3 comprises the amino acid sequence of SEQ ID NO: 58.

18. The bispecific antibody or the antigen-binding fragment of claim 1, wherein according to Chothia definition, the VH1 comprises complementarity determining regions (CDRs) 1, 2, and 3, wherein VH1 CDR1 comprises the amino acid sequence of SEQ ID NO: 44, the VH1 CDR2 comprises the amino acid sequence of SEQ ID NO: 45, and the VH1 CDR3 comprises the amino acid sequence of SEQ ID NO: 46;
the VH2 comprises CDRs 1, 2, and 3, wherein VH2 CDR1 comprises the amino acid sequence of SEQ ID NO: 50, the VH2 CDR2 comprises the amino acid sequence of SEQ ID NO: 51, and the VH2 CDR3 comprises the amino acid sequence of SEQ ID NO: 52;
the VL1 comprises CDRs 1, 2, and 3, wherein VL1 CDR1 comprises the amino acid sequence of SEQ ID NO: 59, the VL1 CDR2 comprises the amino acid sequence of SEQ ID NO: 60, and the VL1 CDR3 comprises the amino acid sequence of SEQ ID NO: 61; and
the VL2 comprises CDRs 1, 2, and 3, wherein VL2 CDR1 comprises the amino acid sequence of SEQ ID NO: 59, the VL2 CDR2 comprises the amino acid sequence of SEQ ID NO: 60, and the VL2 CDR3 comprises the amino acid sequence of SEQ ID NO: 61.

19. The antibody or the antigen-binding fragment thereof of claim 9, wherein
- the VH1 comprises the amino acid sequence of SEQ ID NO: 4 or 12;
- the VH2 comprise the amino acid sequence of SEQ ID NO: 5;
- the VL1 comprise the amino acid sequence of SEQ ID NO: 7; and
- the VL2 comprises the amino acid sequence of SEQ ID NO: 7.

\* \* \* \* \*

UNITED STATES PATENT AND TRADEMARK OFFICE
CERTIFICATE OF CORRECTION

PATENT NO. : 12,049,517 B2
APPLICATION NO. : 16/635878
DATED : July 30, 2024
INVENTOR(S) : Yue Liu, Wenyan Cai and Jiadong Shi It is certified that error appears in the above-identified patent and that said Letters Patent is hereby corrected as shown below:

In the Claims

In Column 110, Line 50 (Approx.), in Claim 1, delete "SEO" and insert -- SEQ --.

Signed and Sealed this
Seventeenth Day of September, 2024

Katherine Kelly Vidal
*Director of the United States Patent and Trademark Office*